United States Patent
Franke et al.

(10) Patent No.: US 10,207,108 B2
(45) Date of Patent: Feb. 19, 2019

(54) IMPLANTABLE NASAL STIMULATOR SYSTEMS AND METHODS

(71) Applicant: Oculeve, Inc., South San Francisco, CA (US)

(72) Inventors: Manfred Franke, Redwood City, CA (US); James Donald Loudin, Houston, TX (US); Janusz Kuzma, Bayview (AU); Paul Taehyun Yun, Los Altos, CA (US); Douglas Michael Ackermann, San Francisco, CA (US)

(73) Assignee: Oculeve, Inc., South San Francisco (*) Notice: Subject to any disclaimer, the term of this patent is extended or adjusted under 35 U.S.C. 154(b) by 0 days.

(21) Appl. No.: 14/920,852

(22) Filed: Oct. 22, 2015

(65) Prior Publication Data
US 2016/0114163 A1   Apr. 28, 2016

Related U.S. Application Data

(60) Provisional application No. 62/067,391, filed on Oct. 22, 2014.

(51) Int. Cl.
| | | |
|---|---|---|
| *A61N 1/36* | (2006.01) | |
| *A61N 1/372* | (2006.01) | |
| *A61N 1/375* | (2006.01) | |

(52) U.S. Cl.
CPC ....... *A61N 1/36046* (2013.01); *A61N 1/3606* (2013.01); *A61N 1/3756* (2013.01); *A61N 1/37205* (2013.01); *A61N 2001/37294* (2013.01)

(58) Field of Classification Search
None
See application file for complete search history.

(56) References Cited

U.S. PATENT DOCUMENTS

| | | |
|---|---|---|
| 3,620,219 A | 11/1971 | Barker |
| 3,709,228 A | 1/1973 | Barker et al. |
| 3,885,550 A | 5/1975 | MacLeod |

(Continued)

FOREIGN PATENT DOCUMENTS

| | | |
|---|---|---|
| CN | 101939043 A | 1/2011 |
| CN | 103467652 A | 12/2013 |

(Continued)

OTHER PUBLICATIONS

Amparo (2013). "Topical Interleukin 1 Receptor Antagonist for Treatment of Dry Eye Disease," JAMA Ophth. 131(6):E1-E9.

(Continued)

*Primary Examiner* — Ankit D Tejani
(74) *Attorney, Agent, or Firm* — Mintz Levin Cohn Ferris Glovsky and Popeo, P.C.

(57) ABSTRACT

Described here are systems, devices, and methods for implanting a nasal stimulator into nasal tissue and electrically stimulating nasal tissue. In some variations, a nasal microstimulator implantation system may comprise an implantation tool and an implantable microstimulator. An implantation tool may comprise a shaft and features to releasably attach a microstimulator. A microstimulator may comprise a passive stimulation circuit and one or more electrodes. In other variations, a nasal implantation system may additionally comprise one or more additional devices, such as a controller, an electrical probe, and/or a dissection tool.

23 Claims, 35 Drawing Sheets

(56) References Cited

U.S. PATENT DOCUMENTS

| | | | |
|---|---|---|---|
| D257,495 S | 11/1980 | Bros et al. |
| 4,495,676 A | 1/1985 | Hartmetz |
| 4,520,825 A | 6/1985 | Thompson et al. |
| 4,539,988 A | 9/1985 | Shirley et al. |
| 4,590,942 A | 5/1986 | Brenman et al. |
| 4,628,933 A | 12/1986 | Michelson |
| 4,681,121 A | 7/1987 | Kobal |
| 4,684,362 A | 8/1987 | Holt |
| 4,706,680 A | 11/1987 | Keusch et al. |
| 4,735,207 A | 4/1988 | Nambu et al. |
| 4,777,954 A | 10/1988 | Keusch et al. |
| 4,780,932 A | 11/1988 | Bowman et al. |
| 4,868,154 A | 9/1989 | Gilbard et al. |
| 4,926,880 A | 5/1990 | Claude et al. |
| 4,957,480 A | 9/1990 | Morenings |
| 4,988,358 A | 1/1991 | Eppley et al. |
| 5,025,807 A | 6/1991 | Zabara |
| 5,072,724 A | 12/1991 | Marcus |
| 5,078,733 A | 1/1992 | Eveleigh et al. |
| 5,090,422 A | 2/1992 | Dahl et al. |
| 5,099,829 A | 3/1992 | Wu |
| 5,147,284 A | 9/1992 | Fedorov et al. |
| 5,324,316 A | 6/1994 | Schulman et al. |
| 5,342,410 A | 8/1994 | Braverman |
| 5,345,948 A | 9/1994 | O'Donnell, Jr. |
| 5,360,438 A | 11/1994 | Fisher |
| 5,498,681 A | 3/1996 | Askari et al. |
| 5,514,131 A | 5/1996 | Edwards et al. |
| 5,533,470 A | 7/1996 | Rose |
| 5,545,617 A | 8/1996 | Dartt et al. |
| 5,571,101 A | 11/1996 | Ellman et al. |
| 5,607,461 A | 3/1997 | Lathrop |
| 5,611,970 A | 3/1997 | Apollonio et al. |
| 5,640,978 A | 6/1997 | Wong |
| 5,683,436 A | 11/1997 | Mendes et al. |
| 5,697,957 A | 12/1997 | Noren et al. |
| 5,707,400 A | 1/1998 | Terry et al. |
| 5,713,833 A | 2/1998 | Milligan |
| 5,720,773 A | 2/1998 | Lopez-Claros |
| 5,733,282 A | 3/1998 | Ellman et al. |
| 5,735,817 A | 4/1998 | Shantha |
| 5,792,100 A | 8/1998 | Shantha |
| 5,794,614 A | 8/1998 | Gruenke et al. |
| 5,800,685 A | 9/1998 | Perrault |
| 5,843,140 A | 12/1998 | Strojnik |
| 5,900,407 A | 5/1999 | Yerxa et al. |
| 5,904,658 A | 5/1999 | Niederauer et al. |
| 5,948,006 A | 9/1999 | Mann |
| 6,001,088 A | 12/1999 | Roberts et al. |
| 6,020,445 A | 2/2000 | Vanderlaan et al. |
| 6,035,236 A | 3/2000 | Jarding et al. |
| 6,050,999 A | 4/2000 | Paraschac et al. |
| 6,051,017 A | 4/2000 | Loeb et al. |
| 6,083,251 A | 7/2000 | Shindo |
| 6,102,847 A | 8/2000 | Stielau |
| 6,152,916 A | 11/2000 | Bige |
| 6,205,359 B1 | 3/2001 | Boveja |
| 6,208,902 B1 | 3/2001 | Boveja |
| 6,240,316 B1 | 5/2001 | Richmond et al. |
| 6,246,911 B1 | 6/2001 | Seligman |
| 6,270,796 B1 | 8/2001 | Weinstein |
| 6,272,382 B1 | 8/2001 | Faltys et al. |
| 6,275,737 B1 | 8/2001 | Mann |
| 6,277,855 B1 | 8/2001 | Yerxa |
| 6,284,765 B1 | 9/2001 | Caffrey |
| 6,324,429 B1 | 11/2001 | Shire et al. |
| 6,327,504 B1 | 12/2001 | Dolgin et al. |
| 6,366,814 B1 | 4/2002 | Boveja et al. |
| 6,405,079 B1 | 6/2002 | Ansarinia et al. |
| 6,438,398 B1 * | 8/2002 | Pflugfelder ............ A61B 3/101 600/321 |
| 6,458,157 B1 | 10/2002 | Suaning |
| 6,505,077 B1 | 1/2003 | Kast et al. |
| 6,526,318 B1 | 2/2003 | Ansarinia et al. |
| 6,535,766 B1 | 3/2003 | Thompson et al. |
| 6,537,265 B2 | 3/2003 | Thanavala et al. |
| 6,539,253 B2 | 3/2003 | Thompson et al. |
| 6,562,036 B1 | 5/2003 | Ellman et al. |
| 6,564,102 B1 | 5/2003 | Boveja |
| 6,578,579 B2 | 6/2003 | Burnside et al. |
| 6,604,528 B1 | 8/2003 | Duncan |
| 6,641,799 B2 | 11/2003 | Goldberg |
| 6,658,301 B2 | 12/2003 | Loeb et al. |
| 6,662,052 B1 | 12/2003 | Sarwal et al. |
| 6,684,879 B1 | 2/2004 | Coffee et al. |
| 6,701,189 B2 | 3/2004 | Fang et al. |
| 6,748,951 B1 | 6/2004 | Schmidt |
| 6,792,314 B2 | 9/2004 | Byers et al. |
| 6,829,508 B2 | 12/2004 | Schulman et al. |
| 6,853,858 B2 | 2/2005 | Shalev |
| 6,871,099 B1 | 3/2005 | Whitehurst et al. |
| 6,879,859 B1 | 4/2005 | Boveja |
| 6,885,888 B2 | 4/2005 | Rezai |
| 6,895,279 B2 | 5/2005 | Loeb et al. |
| 7,024,241 B1 | 4/2006 | Bornzin et al. |
| 7,054,692 B1 | 5/2006 | Whitehurst et al. |
| 7,067,307 B2 | 6/2006 | Hochleitner et al. |
| 7,069,084 B2 | 6/2006 | Yee |
| 7,117,033 B2 | 10/2006 | Shalev et al. |
| 7,142,909 B2 | 11/2006 | Greenberg et al. |
| 7,146,209 B2 | 12/2006 | Gross et al. |
| 7,169,163 B2 | 1/2007 | Becker |
| 7,190,998 B2 | 3/2007 | Shalev et al. |
| 7,225,032 B2 | 5/2007 | Schmeling et al. |
| 7,228,184 B2 | 6/2007 | Heath |
| 7,247,692 B2 | 7/2007 | Laredo |
| 7,317,947 B2 | 1/2008 | Wahlstrand et al. |
| 7,330,762 B2 | 2/2008 | Boveja et al. |
| 7,346,398 B2 | 3/2008 | Gross et al. |
| 7,369,897 B2 | 5/2008 | Boveja et al. |
| 7,442,191 B2 | 10/2008 | Hovda et al. |
| 7,460,911 B2 | 12/2008 | Cosendai et al. |
| 7,477,947 B2 | 1/2009 | Pines et al. |
| 7,502,652 B2 | 3/2009 | Gaunt et al. |
| 7,547,447 B2 | 6/2009 | Yiu et al. |
| 7,565,204 B2 | 7/2009 | Matei et al. |
| 7,599,737 B2 | 10/2009 | Yomtov et al. |
| 7,636,597 B2 | 12/2009 | Gross et al. |
| 7,650,186 B2 | 1/2010 | Hastings et al. |
| D613,408 S | 4/2010 | Gausmann et al. |
| D614,303 S | 4/2010 | Gausmann et al. |
| D614,774 S | 4/2010 | Gausmann et al. |
| 7,725,176 B2 | 5/2010 | Schuler et al. |
| 7,725,195 B2 | 5/2010 | Lima et al. |
| D617,443 S | 6/2010 | Grenon et al. |
| 7,758,190 B2 | 7/2010 | Korb et al. |
| 7,778,703 B2 | 8/2010 | Gross et al. |
| 7,778,711 B2 | 8/2010 | Ben-David et al. |
| 7,792,591 B2 | 9/2010 | Rooney et al. |
| 7,805,200 B2 | 9/2010 | Kast et al. |
| 7,805,202 B2 | 9/2010 | Kuzma et al. |
| 7,805,203 B2 | 9/2010 | Ben-David et al. |
| 7,809,442 B2 | 10/2010 | Bolea et al. |
| 7,835,794 B2 | 11/2010 | Greenberg et al. |
| 7,846,124 B2 | 12/2010 | Becker |
| 7,860,570 B2 | 12/2010 | Whitehurst et al. |
| 7,873,421 B2 | 1/2011 | Karell |
| 7,879,079 B2 | 2/2011 | Tu et al. |
| D638,128 S | 5/2011 | Prokop et al. |
| 7,981,095 B2 | 7/2011 | Grenon et al. |
| 7,993,381 B2 | 8/2011 | Mac et al. |
| 7,998,202 B2 | 8/2011 | Lesh |
| 8,002,783 B2 | 8/2011 | Vercellotti et al. |
| 8,019,419 B1 | 9/2011 | Panescu et al. |
| 8,019,441 B2 | 9/2011 | Wallace et al. |
| 8,080,047 B2 | 12/2011 | Yu |
| 8,145,322 B1 | 3/2012 | Yao et al. |
| 8,155,746 B2 | 4/2012 | Maltan et al. |
| 8,165,680 B2 | 4/2012 | Greenberg et al. |
| 8,204,591 B2 | 6/2012 | Ben-David et al. |
| 8,231,218 B2 | 7/2012 | Hong et al. |
| 8,251,983 B2 | 8/2012 | Larson et al. |
| 8,295,529 B2 | 10/2012 | Petersen et al. |
| 8,318,070 B2 | 11/2012 | Shiah et al. |

(56) References Cited

U.S. PATENT DOCUMENTS

| | | | |
|---|---|---|---|
| D681,839 S | 5/2013 | Nathanson | |
| 8,489,189 B2 | 7/2013 | Tronnes | |
| 8,494,641 B2 | 7/2013 | Boling et al. | |
| 8,626,298 B2 | 1/2014 | Simon | |
| 8,676,324 B2 | 3/2014 | Simon et al. | |
| 8,728,136 B2 | 5/2014 | Feldman | |
| 8,918,181 B2 | 12/2014 | Ackermann et al. | |
| 8,936,594 B2 | 1/2015 | Wolf et al. | |
| 8,986,301 B2 | 3/2015 | Wolf et al. | |
| 8,996,137 B2 | 3/2015 | Ackermann et al. | |
| 9,079,042 B2 | 7/2015 | Tiedtke et al. | |
| 9,095,723 B2 | 8/2015 | Ackermann et al. | |
| 9,265,956 B2 | 2/2016 | Ackermann et al. | |
| 9,440,065 B2 | 9/2016 | Ackermann et al. | |
| 9,687,652 B2 | 6/2017 | Franke et al. | |
| 9,717,627 B2 | 8/2017 | Kuzma et al. | |
| 9,737,702 B2 | 8/2017 | Ackermann et al. | |
| 9,737,712 B2 | 8/2017 | Franke et al. | |
| 9,764,150 B2 | 9/2017 | Loudin et al. | |
| 9,770,583 B2 | 9/2017 | Gupta et al. | |
| 9,821,159 B2 | 11/2017 | Ackermann et al. | |
| 2001/0018918 A1 | 9/2001 | Burnside et al. | |
| 2001/0020177 A1 | 9/2001 | Gruzdowich et al. | |
| 2002/0013594 A1* | 1/2002 | Dinger | A61B 17/1657 606/167 |
| 2002/0035358 A1 | 3/2002 | Wang | |
| 2002/0049290 A1 | 4/2002 | Vanderbilt | |
| 2002/0188331 A1 | 12/2002 | Fang et al. | |
| 2003/0045909 A1 | 3/2003 | Gross et al. | |
| 2003/0114899 A1 | 6/2003 | Woods et al. | |
| 2003/0120323 A1 | 6/2003 | Meadows et al. | |
| 2003/0130809 A1 | 7/2003 | Cohen et al. | |
| 2003/0176898 A1 | 9/2003 | Gross et al. | |
| 2003/0192784 A1 | 10/2003 | Zhou et al. | |
| 2003/0233134 A1 | 12/2003 | Greenberg et al. | |
| 2003/0233135 A1 | 12/2003 | Yee | |
| 2004/0050392 A1 | 3/2004 | Tu et al. | |
| 2004/0059466 A1 | 3/2004 | Block et al. | |
| 2004/0098036 A1 | 5/2004 | Bergersen | |
| 2004/0098067 A1 | 5/2004 | Ohta et al. | |
| 2004/0127942 A1 | 7/2004 | Yomtov et al. | |
| 2004/0138646 A1 | 7/2004 | Walla | |
| 2004/0147973 A1 | 7/2004 | Hauser et al. | |
| 2004/0151930 A1 | 8/2004 | Rouns et al. | |
| 2004/0220644 A1 | 11/2004 | Shalev et al. | |
| 2005/0004621 A1 | 1/2005 | Boveja et al. | |
| 2005/0010250 A1 | 1/2005 | Schuler et al. | |
| 2005/0010266 A1 | 1/2005 | Bogdanowicz | |
| 2005/0101967 A1 | 5/2005 | Weber et al. | |
| 2005/0101994 A1 | 5/2005 | Yamazaki et al. | |
| 2005/0105046 A1 | 5/2005 | Tung | |
| 2005/0137276 A1 | 6/2005 | Yahiaoui et al. | |
| 2005/0159790 A1 | 7/2005 | Shalev et al. | |
| 2005/0197675 A1 | 9/2005 | David et al. | |
| 2005/0251061 A1 | 11/2005 | Schuler et al. | |
| 2005/0267542 A1 | 12/2005 | David et al. | |
| 2005/0268472 A1 | 12/2005 | Bourilkov et al. | |
| 2006/0004423 A1 | 1/2006 | Boveja et al. | |
| 2006/0018872 A1 | 1/2006 | Tew et al. | |
| 2006/0074450 A1 | 4/2006 | Boveja et al. | |
| 2006/0089673 A1 | 4/2006 | Schultheiss et al. | |
| 2006/0095077 A1 | 5/2006 | Tronnes et al. | |
| 2006/0095108 A1 | 5/2006 | Chowdhury et al. | |
| 2006/0100668 A1 | 5/2006 | Ben-David et al. | |
| 2006/0107958 A1 | 5/2006 | Sleeper | |
| 2006/0142822 A1 | 6/2006 | Tulgar | |
| 2006/0161225 A1 | 7/2006 | Sormann et al. | |
| 2006/0195169 A1 | 8/2006 | Gross et al. | |
| 2006/0206155 A1 | 9/2006 | Ben-David et al. | |
| 2006/0216317 A1 | 9/2006 | Reinhard et al. | |
| 2006/0235430 A1 | 10/2006 | Le et al. | |
| 2006/0239482 A1 | 10/2006 | Hatoum et al. | |
| 2006/0259098 A1 | 11/2006 | Erickson | |
| 2006/0271024 A1 | 11/2006 | Gertner et al. | |
| 2006/0271108 A1 | 11/2006 | Libbus et al. | |
| 2007/0038267 A1 | 2/2007 | Shodo et al. | |
| 2007/0060815 A1 | 3/2007 | Martin et al. | |
| 2007/0060954 A1 | 3/2007 | Cameron et al. | |
| 2007/0083245 A1 | 4/2007 | Lamensdorf et al. | |
| 2007/0123938 A1 | 5/2007 | Haller | |
| 2007/0135868 A1 | 6/2007 | Shi et al. | |
| 2007/0150034 A1 | 6/2007 | Rooney et al. | |
| 2007/0219600 A1 | 9/2007 | Gertner et al. | |
| 2007/0237797 A1 | 10/2007 | Peyman | |
| 2007/0237825 A1 | 10/2007 | Levy et al. | |
| 2007/0248930 A1 | 10/2007 | Brawn | |
| 2007/0250119 A1 | 10/2007 | Tyler et al. | |
| 2007/0250135 A1 | 10/2007 | Bartz-Schmidt et al. | |
| 2007/0276314 A1 | 11/2007 | Becker | |
| 2007/0276451 A1 | 11/2007 | Rigaux | |
| 2007/0295327 A1 | 12/2007 | Bottomley | |
| 2007/0299462 A1 | 12/2007 | Becker | |
| 2008/0009897 A1 | 1/2008 | Duran Von Arx | |
| 2008/0021515 A1 | 1/2008 | Horsager et al. | |
| 2008/0082057 A1 | 4/2008 | Korb et al. | |
| 2008/0082131 A1 | 4/2008 | Llanos | |
| 2008/0109054 A1 | 5/2008 | Hastings et al. | |
| 2008/0132933 A1 | 6/2008 | Gerber | |
| 2008/0140141 A1 | 6/2008 | Ben-David et al. | |
| 2008/0183242 A1 | 7/2008 | Tano et al. | |
| 2008/0183243 A1 | 7/2008 | Shodo et al. | |
| 2008/0208335 A1 | 8/2008 | Blum et al. | |
| 2008/0221642 A1 | 9/2008 | Humayun et al. | |
| 2008/0269648 A1 | 10/2008 | Bock | |
| 2008/0294066 A1 | 11/2008 | Hetling et al. | |
| 2009/0005835 A1 | 1/2009 | Greenberg et al. | |
| 2009/0012573 A1 | 1/2009 | Karell et al. | |
| 2009/0018582 A1 | 1/2009 | Ishikawa et al. | |
| 2009/0024187 A1 | 1/2009 | Erickson et al. | |
| 2009/0024189 A1 | 1/2009 | Lee et al. | |
| 2009/0043185 A1 | 2/2009 | McAdams et al. | |
| 2009/0056709 A1 | 3/2009 | Worsoff | |
| 2009/0099600 A1 | 4/2009 | Moore et al. | |
| 2009/0099623 A1 | 4/2009 | Bentwich et al. | |
| 2009/0099626 A1 | 4/2009 | de Juan, Jr. et al. | |
| 2009/0101139 A1 | 4/2009 | Karell | |
| 2009/0124965 A1 | 5/2009 | Greenberg et al. | |
| 2009/0138061 A1 | 5/2009 | Stephens et al. | |
| 2009/0156581 A1 | 6/2009 | Dillon et al. | |
| 2009/0157142 A1 | 6/2009 | Cauller et al. | |
| 2009/0157145 A1 | 6/2009 | Cauller | |
| 2009/0157147 A1 | 6/2009 | Cauller et al. | |
| 2009/0192571 A1 | 7/2009 | Stett et al. | |
| 2009/0204142 A1 | 8/2009 | Becker | |
| 2009/0241840 A1 | 10/2009 | Mills | |
| 2009/0264966 A1 | 10/2009 | Blum et al. | |
| 2009/0281594 A1 | 11/2009 | King et al. | |
| 2009/0281596 A1 | 11/2009 | King et al. | |
| 2009/0299418 A1 | 12/2009 | Shalev et al. | |
| 2009/0306738 A1 | 12/2009 | Weiss et al. | |
| 2010/0030150 A1 | 2/2010 | Paques et al. | |
| 2010/0076423 A1 | 3/2010 | Muller | |
| 2010/0087896 A1 | 4/2010 | McCreery | |
| 2010/0094280 A1 | 4/2010 | Muller | |
| 2010/0139002 A1 | 6/2010 | Walker et al. | |
| 2010/0152708 A1 | 6/2010 | Li et al. | |
| 2010/0161004 A1 | 6/2010 | Najafi et al. | |
| 2010/0168513 A1 | 7/2010 | Pless et al. | |
| 2010/0179468 A1 | 7/2010 | Becker | |
| 2010/0211132 A1 | 8/2010 | Nimmagadda et al. | |
| 2010/0241195 A1 | 9/2010 | Meadows et al. | |
| 2010/0274164 A1 | 10/2010 | Juto | |
| 2010/0274224 A1 | 10/2010 | Jain et al. | |
| 2010/0274313 A1 | 10/2010 | Boling et al. | |
| 2010/0280509 A1 | 11/2010 | Muller et al. | |
| 2010/0288275 A1 | 11/2010 | Djupesland et al. | |
| 2010/0318159 A1 | 12/2010 | Aghassian et al. | |
| 2011/0021975 A1 | 1/2011 | Covello | |
| 2011/0028807 A1 | 2/2011 | Abreu | |
| 2011/0028883 A1 | 2/2011 | Juan, Jr. et al. | |
| 2011/0077551 A1 | 3/2011 | Videbaek | |
| 2011/0077698 A1 | 3/2011 | Tsampazis et al. | |
| 2011/0093043 A1 | 4/2011 | Torgerson et al. | |
| 2011/0151393 A1 | 6/2011 | Frey, II et al. | |

(56) References Cited

U.S. PATENT DOCUMENTS

| | | |
|---|---|---|
| 2011/0152969 A1 | 6/2011 | Zehnder et al. |
| 2011/0202121 A1 | 8/2011 | Wen |
| 2011/0218590 A1 | 9/2011 | DeGiorgio et al. |
| 2011/0234971 A1 | 9/2011 | Yeh |
| 2011/0275734 A1 | 11/2011 | Scales et al. |
| 2011/0276107 A1 | 11/2011 | Simon et al. |
| 2011/0282251 A1 | 11/2011 | Baker et al. |
| 2011/0295336 A1 | 12/2011 | Sharma et al. |
| 2011/0313330 A1 | 12/2011 | Loushin et al. |
| 2011/0313480 A1 | 12/2011 | De Vos |
| 2011/0313481 A1 | 12/2011 | De Vos |
| 2012/0053648 A1 | 3/2012 | Neher et al. |
| 2012/0112903 A1 | 5/2012 | Kaib et al. |
| 2012/0130398 A1* | 5/2012 | Ackermann ....... A61N 1/36046 606/129 |
| 2012/0133887 A1 | 5/2012 | Huang |
| 2012/0197338 A1* | 8/2012 | Su ..................... A61N 1/36167 607/41 |
| 2012/0232615 A1 | 9/2012 | Barolat et al. |
| 2012/0232618 A1 | 9/2012 | Feldman |
| 2012/0234332 A1 | 9/2012 | Shantha |
| 2012/0253249 A1 | 10/2012 | Wilson et al. |
| 2012/0298105 A1 | 11/2012 | Osorio et al. |
| 2012/0315329 A1 | 12/2012 | Ahn et al. |
| 2012/0316557 A1 | 12/2012 | Sartor et al. |
| 2012/0323214 A1 | 12/2012 | Shantha |
| 2012/0323227 A1 | 12/2012 | Wolf et al. |
| 2012/0323232 A1 | 12/2012 | Wolf et al. |
| 2012/0330376 A1 | 12/2012 | Flynn et al. |
| 2013/0006095 A1* | 1/2013 | Jenkins ................ G01R 33/286 600/411 |
| 2013/0006326 A1 | 1/2013 | Ackermann et al. |
| 2013/0053733 A1 | 2/2013 | Korb et al. |
| 2013/0053737 A1 | 2/2013 | Scerbo |
| 2013/0065765 A1 | 3/2013 | Selifonov et al. |
| 2013/0158451 A1 | 6/2013 | Juto et al. |
| 2013/0158626 A1 | 6/2013 | DeGiorgio et al. |
| 2013/0172790 A1 | 7/2013 | Badawi |
| 2013/0178937 A1* | 7/2013 | Vassallo ................ A61B 17/24 623/10 |
| 2013/0253387 A1 | 9/2013 | Bonutti et al. |
| 2013/0261706 A1 | 10/2013 | Mirro et al. |
| 2013/0270491 A1 | 10/2013 | Park et al. |
| 2013/0274824 A1 | 10/2013 | Otto et al. |
| 2013/0274831 A1* | 10/2013 | Otto ..................... A61N 1/3606 607/62 |
| 2013/0304154 A1* | 11/2013 | Goodman .......... A61N 1/36046 607/53 |
| 2013/0310887 A1* | 11/2013 | Curtis ................... A61N 1/371 607/5 |
| 2013/0336557 A1 | 12/2013 | Cruzat et al. |
| 2014/0012182 A1 | 1/2014 | Shantha et al. |
| 2014/0056815 A1 | 2/2014 | Peyman |
| 2014/0081353 A1 | 3/2014 | Cook et al. |
| 2014/0088463 A1 | 3/2014 | Wolf et al. |
| 2014/0163580 A1* | 6/2014 | Tischendorf ....... A61N 1/36139 606/129 |
| 2014/0214120 A1* | 7/2014 | Simon ................ A61N 1/36075 607/46 |
| 2014/0257205 A1 | 9/2014 | Schaller |
| 2014/0257433 A1 | 9/2014 | Ackermann et al. |
| 2014/0277429 A1 | 9/2014 | Kuzma et al. |
| 2014/0316310 A1 | 10/2014 | Ackermann et al. |
| 2014/0316396 A1 | 10/2014 | Wolf et al. |
| 2014/0316485 A1 | 10/2014 | Ackermann et al. |
| 2014/0362339 A1 | 12/2014 | Imafuku |
| 2014/0371565 A1 | 12/2014 | Glasser |
| 2014/0371812 A1 | 12/2014 | Ackermann et al. |
| 2015/0088156 A1 | 3/2015 | Ackermann et al. |
| 2015/0238754 A1 | 8/2015 | Loudin et al. |
| 2015/0335900 A1 | 11/2015 | Ackermann et al. |
| 2015/0362755 A1 | 12/2015 | Lee et al. |
| 2016/0022992 A1 | 1/2016 | Franke et al. |
| 2016/0114172 A1 | 4/2016 | Loudin et al. |
| 2016/0121118 A1 | 5/2016 | Franke et al. |
| 2016/0158548 A1 | 6/2016 | Ackermann et al. |
| 2016/0270656 A1 | 9/2016 | Samec et al. |
| 2016/0367795 A1 | 12/2016 | Ackermann et al. |
| 2016/0367806 A1 | 12/2016 | Kahook |
| 2017/0049619 A1 | 2/2017 | Kahook |
| 2017/0157401 A1 | 6/2017 | Loudin et al. |
| 2017/0239459 A1 | 8/2017 | Loudin et al. |
| 2017/0252563 A1 | 9/2017 | Franke et al. |
| 2017/0312521 A1 | 11/2017 | Franke et al. |
| 2017/0340884 A1 | 11/2017 | Franke et al. |
| 2017/0354536 A1 | 12/2017 | Kuzma et al. |
| 2017/0368332 A1 | 12/2017 | Ackermann et al. |
| 2017/0368359 A1 | 12/2017 | Loudin et al. |
| 2018/0064940 A1 | 3/2018 | Ackermann et al. |
| 2018/0064941 A1 | 3/2018 | Ackermann et al. |
| 2018/0064942 A1 | 3/2018 | Ackermann et al. |

FOREIGN PATENT DOCUMENTS

| | | |
|---|---|---|
| EP | 0 109 935 A1 | 5/1984 |
| EP | 1497483 | 1/2005 |
| EP | 1651307 | 5/2006 |
| EP | 1919553 | 5/2008 |
| EP | 1958661 A1 | 8/2008 |
| EP | 2205193 | 7/2010 |
| EP | 2205314 | 7/2010 |
| EP | 2102681-0001 | 10/2012 |
| EP | 2199000-0001 | 3/2013 |
| GB | 2 129 690 B | 3/1987 |
| GB | 2 456 002 A | 7/2009 |
| JP | S60500241 A | 2/1985 |
| JP | 2002-325851 A | 11/2002 |
| JP | 2002-539859 A | 11/2002 |
| JP | 2005-052461 A | 3/2005 |
| JP | 2005-144178 A | 6/2005 |
| JP | 2006-515900 A | 6/2006 |
| JP | 2006-311917 A | 11/2006 |
| JP | 2007-044323 A | 2/2007 |
| JP | 2007-528751 A | 10/2007 |
| JP | 2008-183248 A | 8/2008 |
| JP | 2008-541850 A | 11/2008 |
| JP | 2009-523503 A | 6/2009 |
| JP | 2010-505563 A | 2/2010 |
| JP | 2010-051562 A | 3/2010 |
| JP | 2010-537777 A | 12/2010 |
| JP | 2011-030734 A | 2/2011 |
| JP | 2011-524780 A | 9/2011 |
| WO | WO-00/56393 A1 | 9/2000 |
| WO | WO-00/62672 A1 | 10/2000 |
| WO | WO-2003/087433 A1 | 10/2003 |
| WO | WO-2004/026106 A2 | 4/2004 |
| WO | WO-2004/026106 A3 | 4/2004 |
| WO | WO-2004/043217 A2 | 5/2004 |
| WO | WO-2004/043217 A3 | 5/2004 |
| WO | WO-2004/091453 A1 | 10/2004 |
| WO | WO-2004/112893 A2 | 12/2004 |
| WO | WO-2004/112893 A3 | 12/2004 |
| WO | WO-2005/007234 A2 | 1/2005 |
| WO | WO-2005/007234 A3 | 1/2005 |
| WO | WO-2005/030025 A2 | 4/2005 |
| WO | WO-2005/030025 A3 | 4/2005 |
| WO | WO-2005/060984 A1 | 7/2005 |
| WO | WO-2006/127366 A1 | 11/2006 |
| WO | WO-2007/079543 A1 | 7/2007 |
| WO | WO-2008/156501 A2 | 12/2008 |
| WO | WO-2008-156501 A3 | 12/2008 |
| WO | WO-2009/035571 A2 | 3/2009 |
| WO | WO-2009/035571 A3 | 3/2009 |
| WO | WO-2009/048580 A1 | 4/2009 |
| WO | WO-2009/070709 A1 | 6/2009 |
| WO | WO-2009/154457 A2 | 12/2009 |
| WO | WO-2010/003011 A1 | 1/2010 |
| WO | WO-2010/027743 A1 | 3/2010 |
| WO | WO-2010/099818 A1 | 9/2010 |
| WO | WO-2011/011373 A1 | 1/2011 |
| WO | WO-2012/068247 A1 | 5/2012 |
| WO | WO-2012/139063 A2 | 10/2012 |
| WO | WO-2012-139063 A3 | 10/2012 |

(56) References Cited

FOREIGN PATENT DOCUMENTS

| WO | WO-2012/155188 A1 | 11/2012 |
|---|---|---|
| WO | WO-2013/055940 A2 | 4/2013 |
| WO | WO-2013/055940 A3 | 4/2013 |
| WO | WO-2013/157320 A1 | 10/2013 |
| WO | WO-2013/165697 A1 | 11/2013 |
| WO | WO-2013/166353 A1 | 11/2013 |
| WO | WO-2014/138709 A1 | 9/2014 |
| WO | WO-2014/165124 A1 | 10/2014 |
| WO | WO-2014/172693 A2 | 10/2014 |
| WO | WO-2014/172693 A3 | 10/2014 |
| WO | WO-2015/130707 A2 | 9/2015 |
| WO | WO-2015/130707 A3 | 9/2015 |
| WO | WO-2016/015025 A1 | 1/2016 |
| WO | WO-2016/025323 A1 | 2/2016 |
| WO | WO-2016/065211 A1 | 4/2016 |
| WO | WO-2016/065213 A1 | 4/2016 |
| WO | WO-2016/065215 A1 | 4/2016 |

OTHER PUBLICATIONS

Boberg-Ans J. (1955). "Experience in clinical examination of corneal sensitivity: corneal sensitivity and the naso-lacrimal reflex after retrobulbar anaesthesia," Br. J. Ophthalmol. 39(12):705-726.
Bajpai et al. (2012). "Preparation, Characterization and Water Uptake Behavior of Polysaccharide Based Nanoparticles," Prog. Nanotech. Nanomat. 1(1):9-17.
Baraniuk et al. (2007). "Nasonasal Reflexes, the Nasal Cycle, and Sneeze," Curr. Allergy and Asthma Reports 7:105-111.
Baroody FM, Foster KA, Markaryan A, et al. Nasal ocular reflexes and eye symptoms in patients with allergic rhinitis. Ann Allergy Asthma Immunol 2008;100:194-199.
Baroody FM, Shenaq D, DeTineo M, et al. Fluticasone furoate nasal spray reduces the nasal-ocular reflex: a mechanism for the efficacy of topical steroids in controlling allergic eye symptoms. J Allergy Clin Immunol 2009;123:1342-1348.
Calonge (2001). "The Treatment of Dry Eye," Survey Ophth. 45(2)S227-S239.
Cipriano et al. (2014). "Superabsorbent Hydrogels That are Robust and Highly Stretchable," Am. Chem Soc. 47(13):4445-4452.
Dart et al. (2002). "Effects of 25% Propylene Glycol Hydrogel (Solugel) on Second Intention Wound Healing in Horses," Vet. Surg. 31(4):309-313.
Drummond PD. Lacrimation and cutaneous vasodilatation in the face induced by painful stimulation of the nasal ala and upper lip. J Auton Nery Syst 1995;51:109-16.
Elsby et al. (1967). "Lacrimal Secretion in the Cat," Br. J. Pharm. Chemother. 29(1):1-7.
Extended European Search Report (includes Supplementary European Search Report and Search Opinion) received for European Patent Application No. 11842076.9, dated Oct. 10, 2014.
Extended European Search Report received for European Patent Application No. 12768458.7, dated Aug. 28, 2014, 7 pages.
Extended European Search Report dated Oct. 21, 2016, for EP Application No. 14 778 719.6, filed on Mar. 12, 2014, 8 pages.
Final Office Action received for U.S. Appl. No. 13/441,806, dated Mar. 12, 2015.
Final Office Action received for U.S. Appl. No. 13/441,806, dated May 20, 2016.
Final Office Action received for U.S. Appl. No. 14/816,846, dated May 11, 2016, 12 pages.
Final Office Action received for U.S. Appl. No. 14/207,072, dated Jun. 22, 2016.
Final Office Action dated Sep. 23, 2016, for U.S. Appl. No. 14/809,109, filed Jul. 24, 2015, 10 pages.
Final Office Action received for U.S. Appl. No. 14/256,916, dated Apr. 8, 2015.
Final Office Action received for U.S. Appl. No. 14/313,937 dated Apr. 29, 2015.
Final Office Action received for U.S. Appl. No. 14/630,471, dated Sep. 26, 2016, 22 pages.
Final Office Action received for U.S. Appl. No. 14/256,916, dated Aug. 19, 2016, 19 pages.
Fujisawa et al. (2002). "The Effect of Nasal Mucosal Stimulation on Schirmer Tests in Sjogren's Syndrome and Dry Eye Patients," Lac. Gland Tear Film Dry Eye Syndrome 3 506:1221-1226.
Gupta et al. (1997). "Nasolacrimal Stimulation of Aqueous Tear Production," Cornea 16(6):645-648.
Heigle TJ, Pflugfelder SC. Aqueous tear production in patients with neurotrophic keratitis. Cornea 1996;15:135-8.
Holzer P. Capsaicin: cellular targets, mechanisms of action, and selectivity for thin sensory neurons. Pharmacol Rev 1991;43:143-201.
Ikemura et al. (2008). "UV-VIS Spectra and Photoinitiation Behaviors of Acylphosphine Oxide and Bisacylphosphine Oxide Derivatives in unfilled, Light-Cured Dental Resins," Dental Mat. J. 27(6):765-774.
International Preliminary Report on Patentability received for PCT Application No. PCT/US2014/022158, dated Sep. 17, 2015.
International Preliminary Report on Patentability received for PCT Patent Application No. PCT/US2011/060989, dated May 30, 2013.
International Preliminary Report on Patentability received for PCT Application No. PCT/US2014/024496, dated Sep. 15, 2015.
International Preliminary Report on Patentability received for PCT Patent Application No. PCT/US2012/032629, dated Oct. 17, 2013.
International Preliminary Report on Patentability received for PCT Patent Application No. PCT/US2014/034733, dated Oct. 29, 2015.
International Search Report & Written Opinion received for PCT Patent Application No. PCT/US2011/060989, dated Feb. 23, 2012.
International Search Report & Written Opinion received for PCT Patent Application No. PCT/US2014/022158, dated Jul. 30, 2014.
International Search Report and Written Opinion received for PCT Application No. PCT/US2015/042130, dated Oct. 28, 2015.
International Search Report and Written Opinion received for PCT Patent Application No. PCT/US2014/034733, dated Dec. 5, 2014.
International Search Report and Written Opinion received for PCT Patent Application No. PCT/US2015/017379, dated Jul. 24, 2015.
International Search Report and Written Opinion received for PCT Patent Application No. PCT/US2015/057023, dated Mar. 4, 2016.
International Search Report and Written Opinion received for PCT Patent Application No. PCT/US2014/024496, dated Aug. 22, 2014, 11 pages.
International Search Report received for PCT Patent Application No. PCT/US2012/32629, dated Oct. 26, 2012.
International Search Report received for PCT Patent Application No. PCT/US2015/57021, dated Feb. 10, 2016.
International Search Report received for PCT Patent Application No. PCT/US2015/57019, dated Feb. 11, 2016, 4 pages.
Krupin T, Cross DA, Becker B. Decreased basal tear production associated with general anesthesia. Arch Ophthalmol 1977;95:107-108.
Lora et al. (2009). "Lacrimal Nerve Stimulation by a Neurostimulator for Tear Production," Invest. Ophth. Vis. Science 50(13):172.
Loth S, Bende M. Effect of nasal anaesthesia on lacrimal function after nasal allergen challenge. Clin Exp Allergy 1994;24:375-376.
Meng, I.D. et al. (2013). "The role of corneal afferent neurons in regulating tears under normal and dry eye conditions," Exp. Eye Res. 117:79-87.
Mallepally et al. (2013). "Superabsorbent Alginate Aerogels," J. Supercritical Fluids 79:1-5.
Non-Final Office Action received for U.S. Appl. No. 13/441,806, dated Sep. 17, 2015.
Non-Final Office Action received for U.S. Appl. No. 13/298,042, dated Oct. 2, 2013.
Non-Final Office Action received for U.S. Appl. No. 13/441,806, dated Dec. 18, 2013.
Non-Final Office Action received for U.S. Appl. No. 14/201,753, dated Apr. 2, 2015.
Non-Final Office Action received for U. S. Appl. No. 14/256,915, dated Aug. 13, 2014, 11 pages.
Non-Final Office Action received for U.S. Appl. No. 14/256,916, dated Sep. 12, 2014, 24 pages.

(56) References Cited

OTHER PUBLICATIONS

Non-Final Office Action received for U.S. Appl. No. 14/809,109, dated Apr. 8, 2016.
Non-Final Office Action for U.S. Appl. No. 14/816,846, dated Sep. 11, 2015.
Non-Final Office Action received for U.S. Appl. No. 14/920,860, dated Aug. 17, 2016.
Non-Final Office Action received for U.S. Appl. No. 14/256,916, dated Nov. 19, 2015, 20 pages.
Non-Final Office Action received for U.S Appl. No. 14/313,937, dated Oct. 6, 2015, 7 pages.
Non-Final Office Action dated Sep. 30, 2016, for U.S. Appl. No. 15/256,392, filed Sep. 2, 2016, 14 pages.
Non-Final Office Action received for U.S. Appl. No. 14/207,072, dated Dec. 9, 2015.
Non-Final Office Action dated Sep. 27, 2016, for U.S. Appl. No. 14/920,847, filed Oct. 22, 2015, 13 pages.
Non-Final Office Action dated Nov. 2, 2016, for U.S. Appl. No. 13/441,806, filed Apr. 6, 2012, 11 pages.
Non-Final Office Action received for U.S. Appl. No. 14/313,937, dated Nov. 19, 2014, 12 pages.
Non-Final Office Action received for U.S. Appl. No. 14/630,471, dated Jun. 14, 2016.
Notice of Allowance received for U.S. Appl. No. 14/201,753, dated Dec. 15, 2015.
Notice of Allowance received for U.S. Appl. No. 14/201,753, dated Oct. 15, 2015.
Notice of Allowance received for U.S. Appl. No. 13/298,042, dated Apr. 29, 2014.
Notice of Allowance received for U.S. Appl. No. 13/298,042, dated Aug. 11, 2014.
Notice of Allowance received for U.S. Appl. No. 13/298,042, dated Nov. 13, 2014.
Notice of Allowance received for U.S. Appl. No. 14/561,107, dated Mar. 31, 2015.
Notice of Allowance received for U.S. Appl. No. 14/313,937, dated May 2, 2016, 7 pages.
Notice of Allowance received for U.S. Appl. No. 14/256,915, dated Nov. 26, 2014, 7 pages.
Notice of Allowance received for U.S. Appl. No. 14/313,937, dated Feb. 19, 2016, 8 pages.
Pasqui et al. (2012). "Polysaccharide-Based Hydrogels: The Key Role of Water in Affecting Mechanical Properties," Polymers 4(3):1517-1534.
Philip G, Baroody FM, Proud D, et al. The human nasal response to capsaicin. J Allergy Clin Immunol 1994;94:1035-1045.
Restriction Requirement dated Jul. 2, 2013, for U.S. Appl. No. 13/298,042, filed Nov. 16, 2011, 7 pages.
Roessler et al. (2009). "Implantation and Explantation of a Wireless Epiretinal Retina Implant Device: Observations During the EPIRET3 Prospective Clinical Trial," Invest. Ophthal. Visual Science.
Ruskell (2004). "Distribution of Pterygopalatine Ganglion Efferents to the Lacrimal Gland in Man," Exp. Eye Res. 78(3):329-335.
Sall et al. (2000). "Two Multicenter, Randomized Studies of the Efficacy and Safety of Cyclosporine Ophthalmic Emulsion in Moderate to Severe Dry Eye Disease," Ophth. 107(4):631-639.
Shaari et al. (1995). "Rhinorrhea is decreased in dogs after nasal application of botulinum toxin," Oto. Head Neck Surg. 112(4):566-571.
Stjernschantz et al. (1979). "Electrical Stimulation of the Fifth Cranial Nerve in Rabbits: Effects on Ocular Blood Flow, Extravascular Albumin Content and Intraocular Pressure," Exp. Eye Res. 28(2):229-238.
Stjernschantz et al. (1980). "Vasomotor effects of Facial Nerve Stimulation: Noncholinergic Vasodilation in the eye," Acta Phys. Scand. 109(1):45-50.
Tsubota (1991). "The Importance of the Schirmer Test with Nasal Stimulation," Am. J. Ophth. 111:106-108.
Velikay-Parel et al. (2011). "Perceptual Threshold and Neuronal Excitability as Long-Term Safety Evaluation in Retinal Implants," Invest. Opht. Visual Science E-Abstract 2590, 2 pages.
Written Opinion received for PCT Patent Application No. PCT/US2012/032629, dated Oct. 26, 2012, 8 pages.
Written Opinion received for PCT Patent Application No. PCT/US2015/57021, dated Feb. 10, 2016.
Written Opinion received for PCT Patent Application No. PCT/US2015/57019, dated Feb. 11, 2016, 6 pages.
Zilstorff-Pedersen (1965). "Quantitative Measurements of The Nasolacrimal Reflex," Arch. Oto. 81:457-462.
US. Appl. No. 15/256,392, filed Sep. 2, 2016, by Ackermann et al.
Acar, M. et al. (2013). "Ocular surface assessment in patients with obstructive sleep apnea-hypopnea syndrome," Sleep Breath 17(2):583-588.
Anonymous (2007). "The epidemiology of dry eye disease: report of the Epidemiology Subcommittee of the International Dry Eye WorkShop (2007)," Ocul. Surf. 5(2):93-107.
Corrected Notice of Allowance dated Feb. 23, 2015, for U.S. Appl. No. 14/256,915, filed Apr. 18, 2014, 2 pages.
Corrected Notice of Allowance dated Jun. 9, 2017, for U.S. Appl. No. 14/920,860, filed Oct. 22, 2015, 2 pages.
Extended European Search Report dated Nov. 18, 2016, for EP Application No. 14 785 631.4, filed on Apr. 18, 2014, 7 pages.
Final Office Action dated Mar. 10, 2017, for U.S. Appl. No. 14/920,847, filed Oct. 22, 2015, 12 pages.
Final Office Action dated May 17, 2017, for U.S. Appl. No. 13/441,806, filed Apr. 6, 2012, 5 pages.
Non-Final Office Action dated Feb. 14, 2017, for U.S. Appl. No. 14/630,471, filed Feb. 24, 2015, 23 pages.
Non-Final Office Action dated Apr. 19, 2017, for U.S. Appl. No. 14/256,916, filed Apr. 18, 2014, 19 pages.
Non-Final Office Action dated Dec. 6, 2016, for U.S. Appl. No. 14/816,846, filed Aug. 3, 2015, 13 pages.
Notice of Allowance dated Dec. 19, 2016, for U.S. Appl. No. 14/809,109, filed Jul. 24, 2015, 8 pages.
Notice of Allowance dated Jan. 19, 2017, for U.S. Appl. No. 14/920,860, filed Oct. 22, 2015, 5 pages.
Notice of Allowance dated Mar. 21, 2017, for U.S. Appl. No. 14/809,109, filed Jul. 24, 2015, 8 pages.
Notice of Allowance dated Mar. 28, 2017, for U.S. Appl. No. 14/207,072, filed Mar. 12, 2014, 8 pages.
Notice of Allowance dated Apr. 17, 2017, for U.S. Appl. No. 15/256,392, filed Sep. 2, 2016, 10 pages.
Notice of Allowance dated Apr. 20, 2017, for U.S. Appl. No. 14/920,860, filed Oct. 22, 2015, 5 pages.
Notice of Allowance dated May 26, 2017, for U.S. Appl. No. 14/630,471, filed Feb. 24, 2015, 5 pages.
Notice of Allowance dated May 30, 2017, for U.S. Appl. No. 14/920,847, filed Oct. 22, 2015, 5 pages.
Corrected Notice of Allowance dated Jul. 17, 2017, for U.S. Appl. No. 15/256,392, filed Sep. 2, 2016, 2 pages.
Extended European Search Report dated Sep. 19, 2017, for EP Application No. 15 754 827.2, filed Feb. 24, 2015, 9 pages.
Final Office Action dated Sep. 1, 2017, for U.S. Appl. No. 14/816,846, filed Aug. 3, 2015, 12 pages.
Final Office Action dated Nov. 8, 2017, for U.S. Appl. No. 14/256,916, filed Apr. 18, 2014, 21 pages.
Friedman et al. (2016). "A nonrandomized, open-label study to evaluate the effect of nasal stimulation on tear production in subjects with dry eye disease," Clin. Ophthal. 10:795-804.
International Search Report dated Aug. 7, 2017, for PCT Patent Application No. PCT/US2017/30617, filed on May 2, 2017, 2 pages.
Non-Final Office Action dated Jul. 17, 2017, for U.S. Appl. No. 15/598,063, filed May 17, 2017, 9 pages.
Notice of Allowance dated Aug. 2, 2017, for U.S. Appl. No. 13/441,806, filed Apr. 6, 2012, 5 pages.
Written Opinion of the International Search Authority dated Aug. 7, 2017, for PCT Patent Application No. PCT/US2017/30617, filed on May 2, 2017, 4 pages.
Extended European Search Report dated Nov. 27, 2017, for EP Application No. 17 167 504.4, filed on Apr. 6, 2012, 9 pages.
Extended European Search Report dated Jan. 8, 2018, for EP Application No. 15 824 539.9, filed on Jul. 24, 2015, 6 pages.
Eye Health (2014). "Watery eyes in cold weather," Oregon Eye Specialists, PC, located at http://www.oregoneyes.net/watery-eyes-in-cold-weather/, 4 total pages.
Final Office Action dated Feb. 22, 2018, for U.S. Appl. No. 14/256,916, filed Apr. 18, 2014, 24 pages.

(56) References Cited

OTHER PUBLICATIONS

Galor, A. et al. (2014). "Environmental factors affect the risk of dry eye syndrome in a United States veteran population," Opth. 121:972-973.
Harvard Health Publishing (2010). "Dry eyes and what you can try," Harvard Medical School, 2 total pages.
International Search Report dated Feb. 12, 2018, for PCT Patent Application No. PCT/US2017/63916, filed on Nov. 30, 2017, 3 pages.
Non-Final Office Action dated Dec. 28, 2017, for U.S. Appl. No. 15/676,910, filed Aug. 14, 2017, 10 pages.
Notice of Allowance dated Jan. 29, 2018, for U.S. Appl. No. 15/700,935, filed Sep. 11, 2017, 7 pages.
Notice of Allowance dated Feb. 13, 2018, for U.S. Appl. No. 15/700,935, filed Sep. 11, 2017, 2 pages.
Petrov, A. et al. (2016). "SkQ1 Ophthalmic Solution for Dry Eye Treatment: Results of a Phase 2 Safety and Efficacy Clinical Study in the Environment and During Challenge in the Controlled Adverse Environment Model," Adv. Ther. 33:96-115.
Vapor Pressure Data for H2O (2012). Handbook of Chemistry and Physics, 73rd edition, 1 total page.
van Setten, G. et al. (2016). "Evidence of seasonality and effects of psychrometry in dry eye disease," Acta Opth. 94:499-506.
Written Opinion of the International Searching Authority dated Feb. 12, 2018, for PCT Patent Application No. PCT/US2017/63916, filed on Nov. 30, 2017, 6 pages.

* cited by examiner

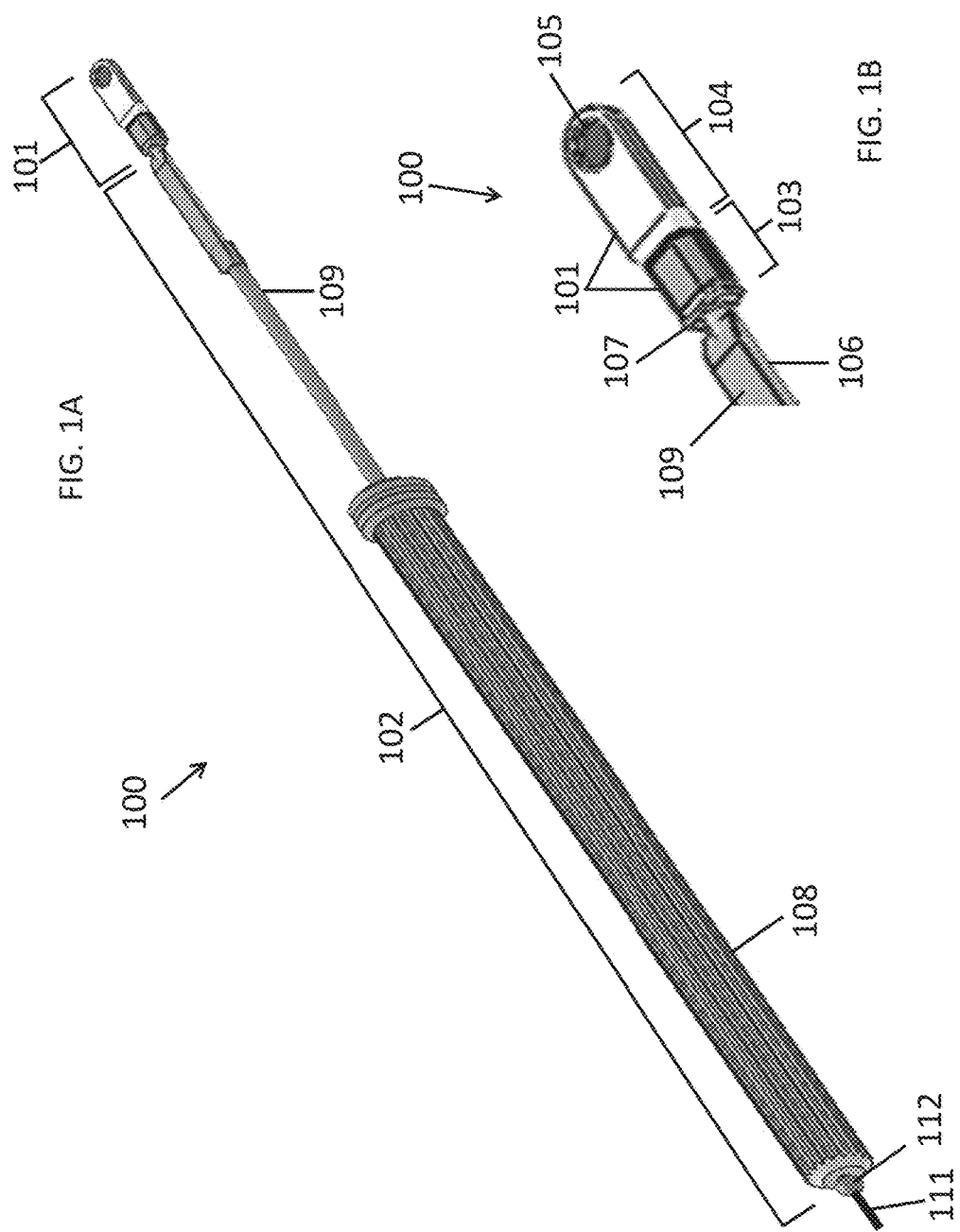

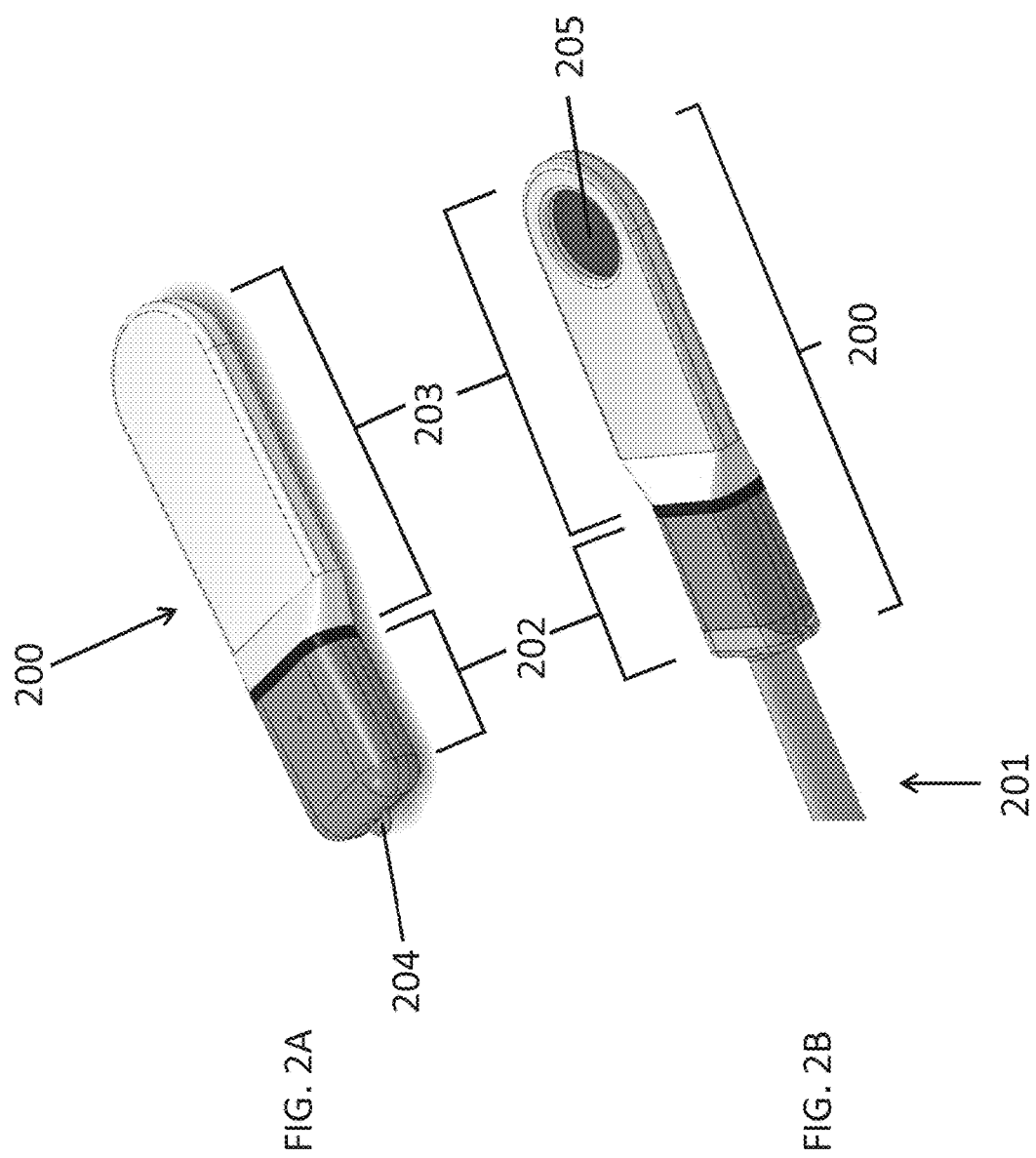

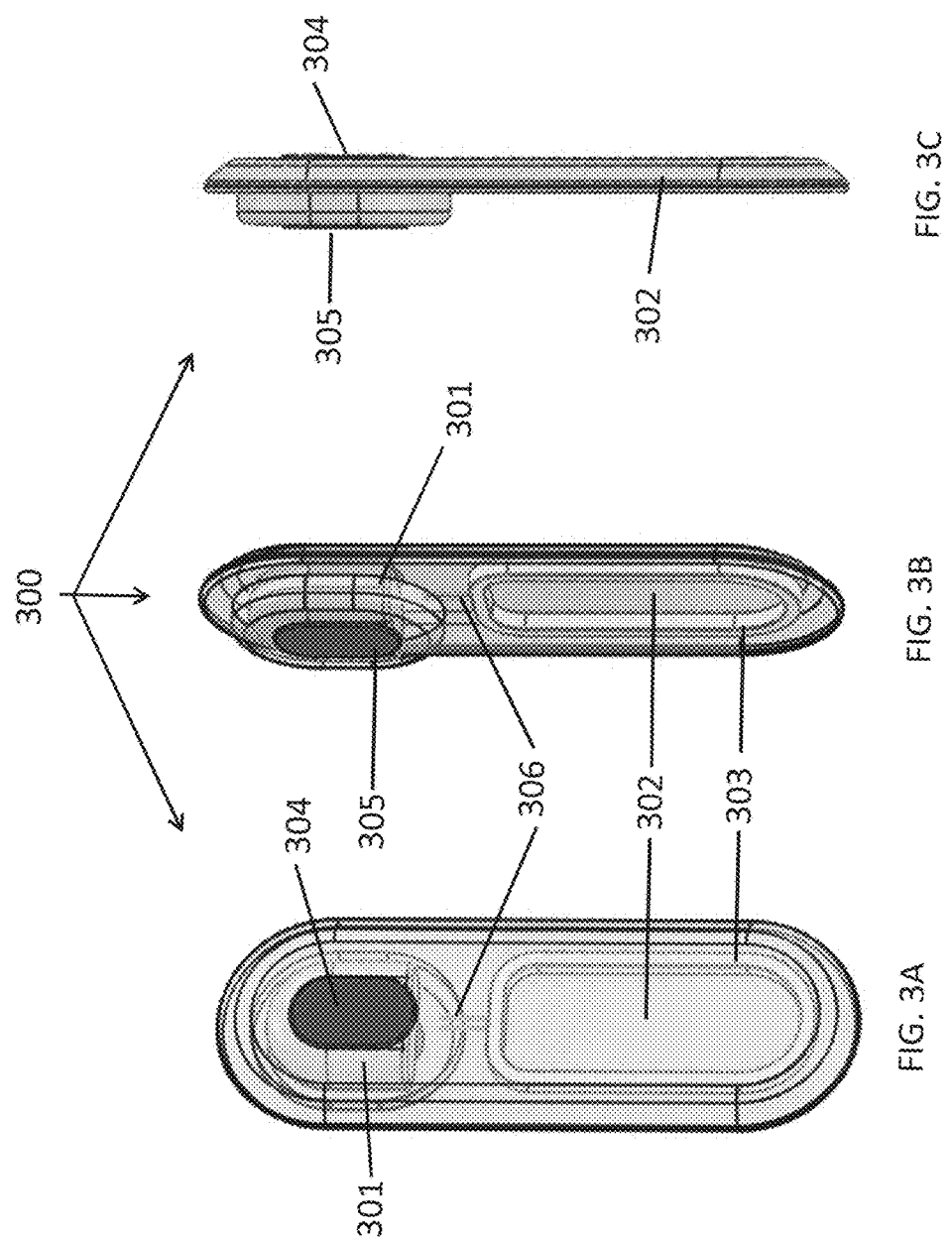

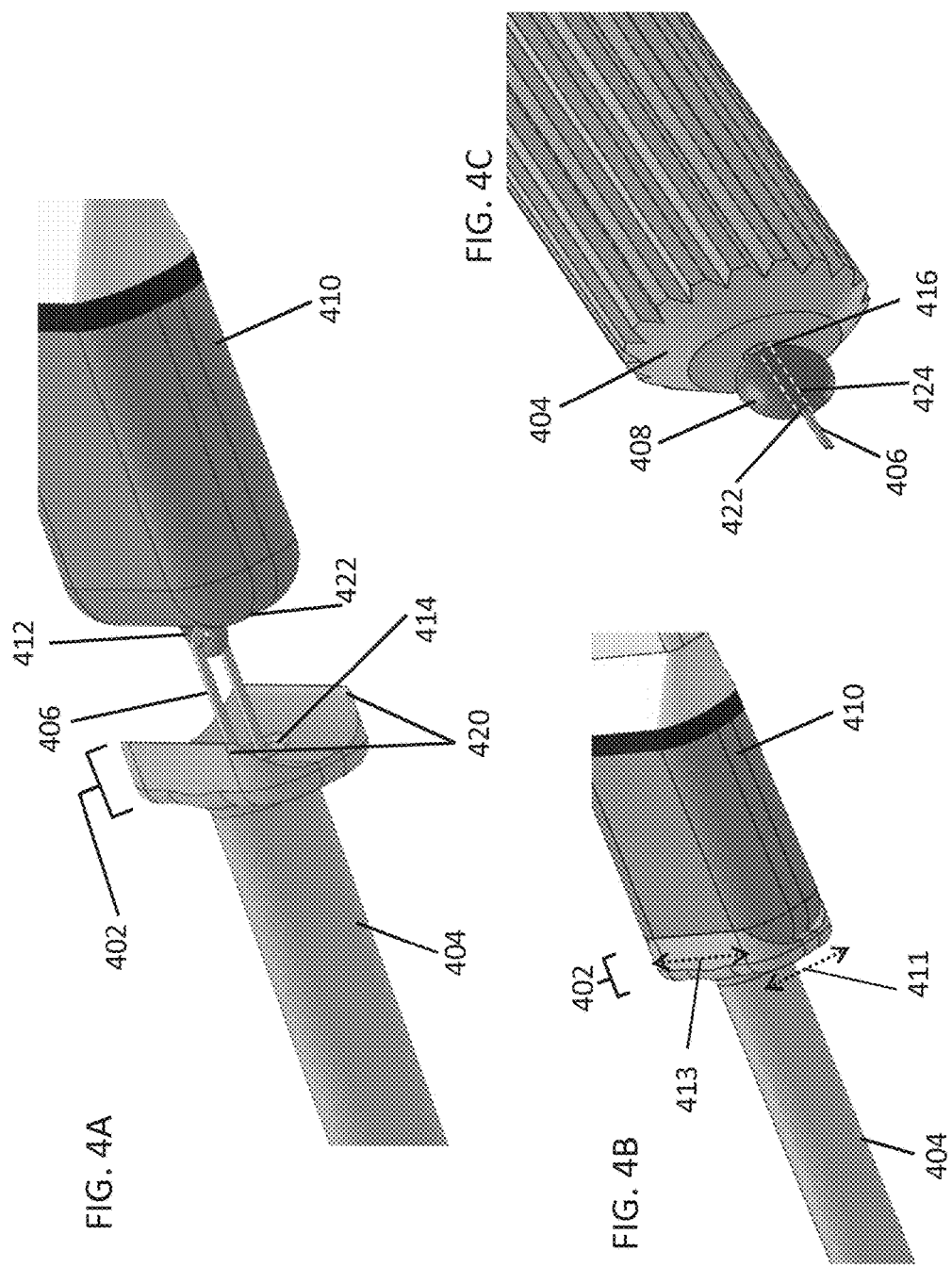

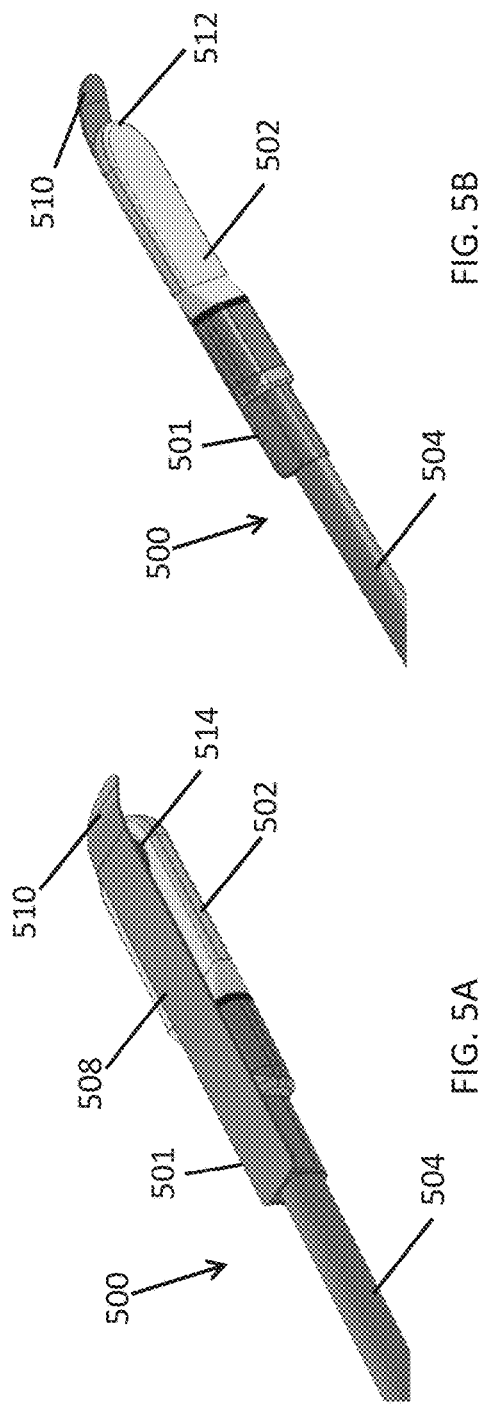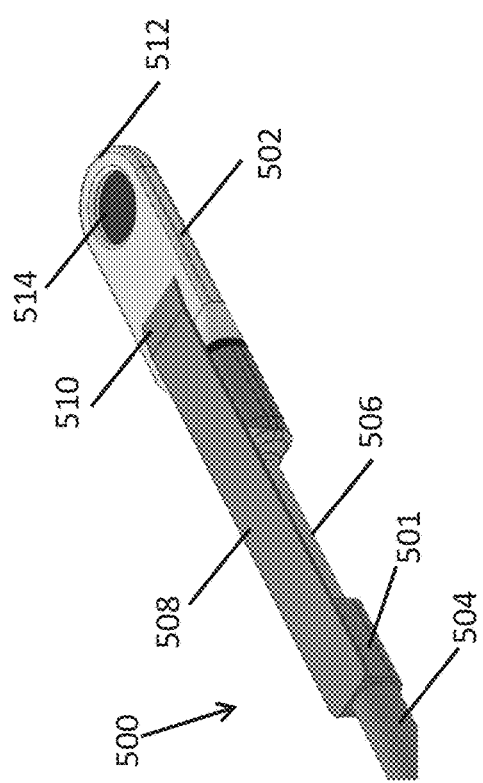

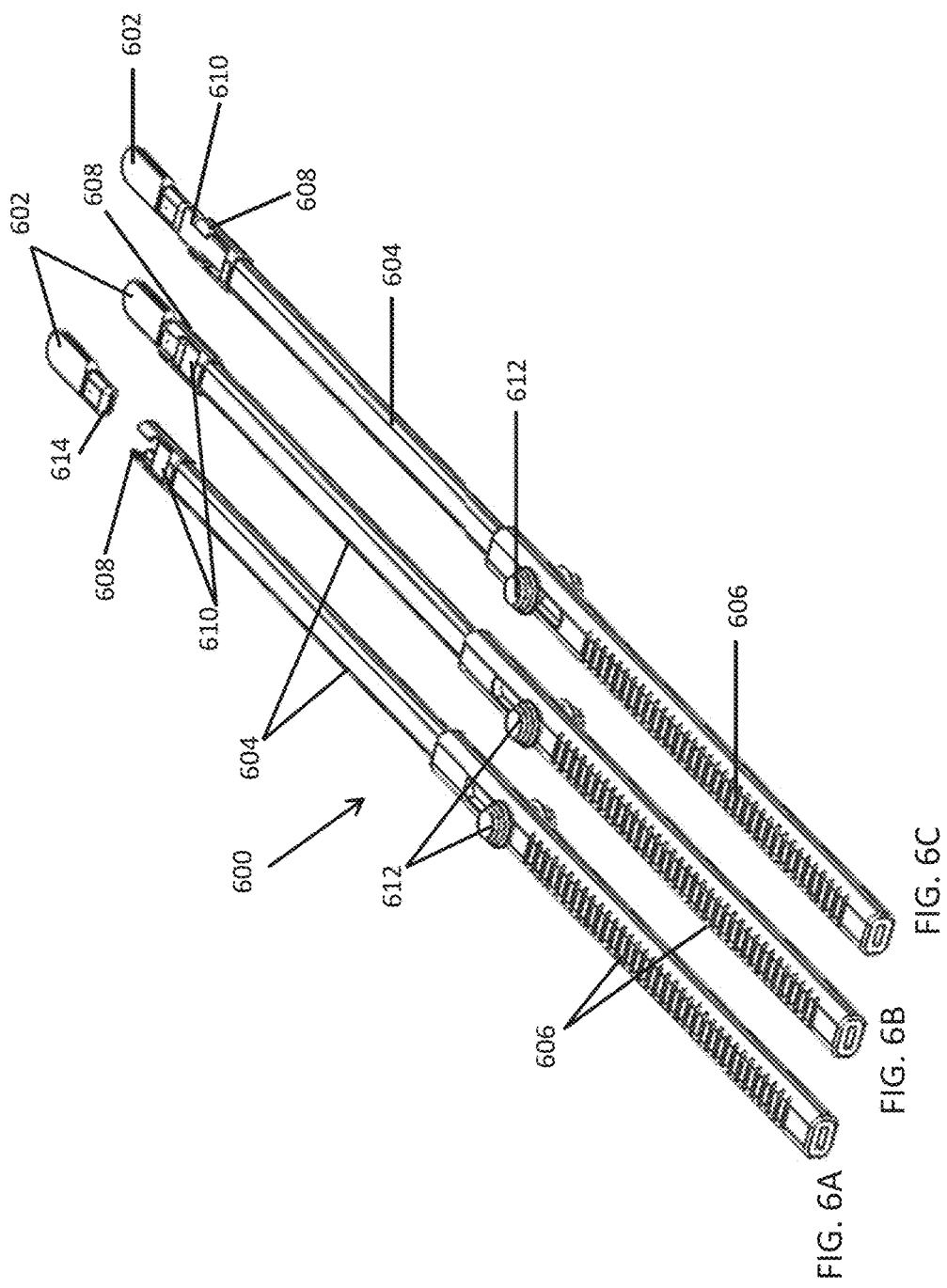

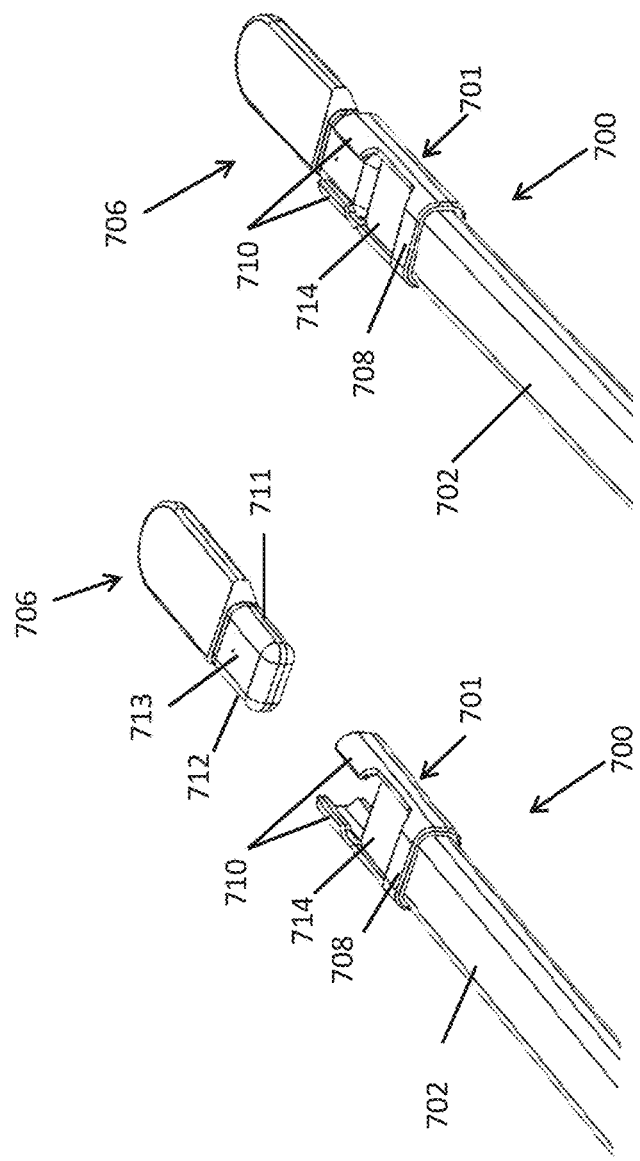

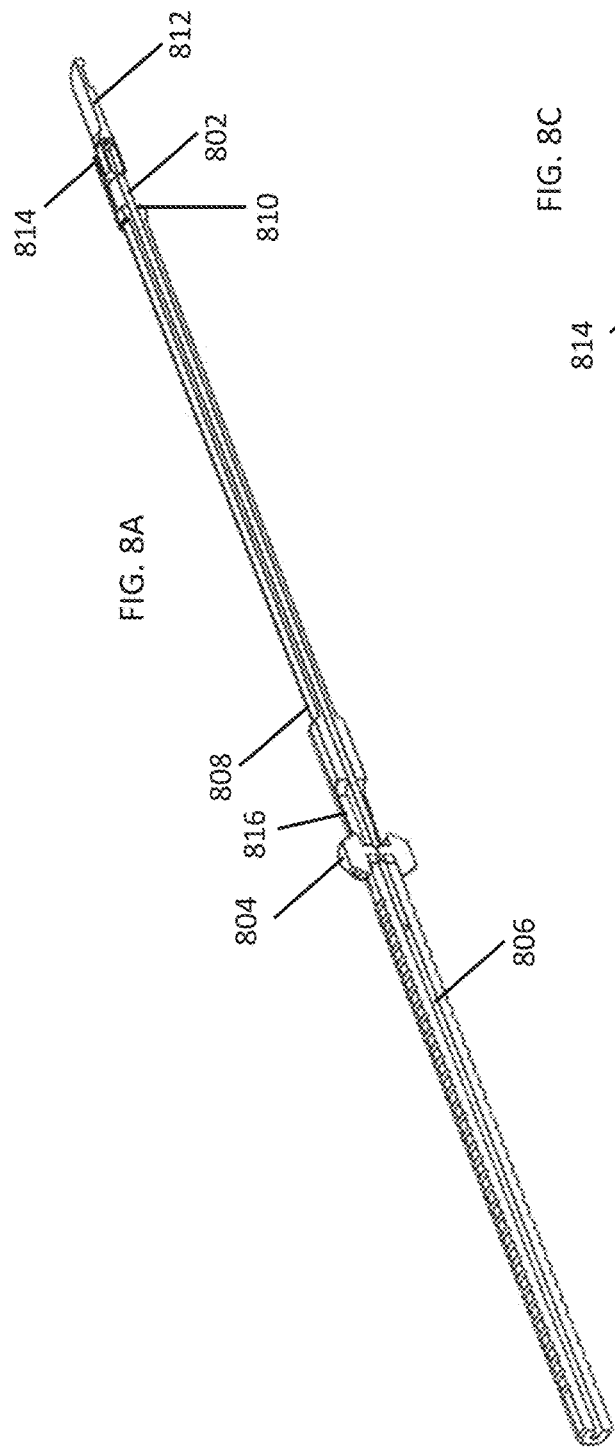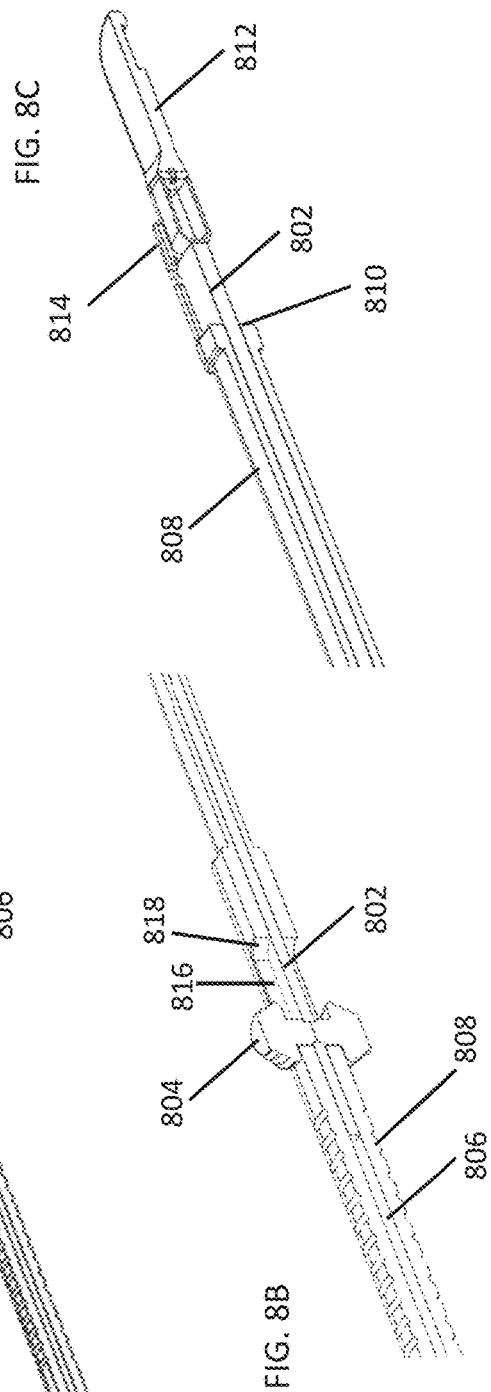

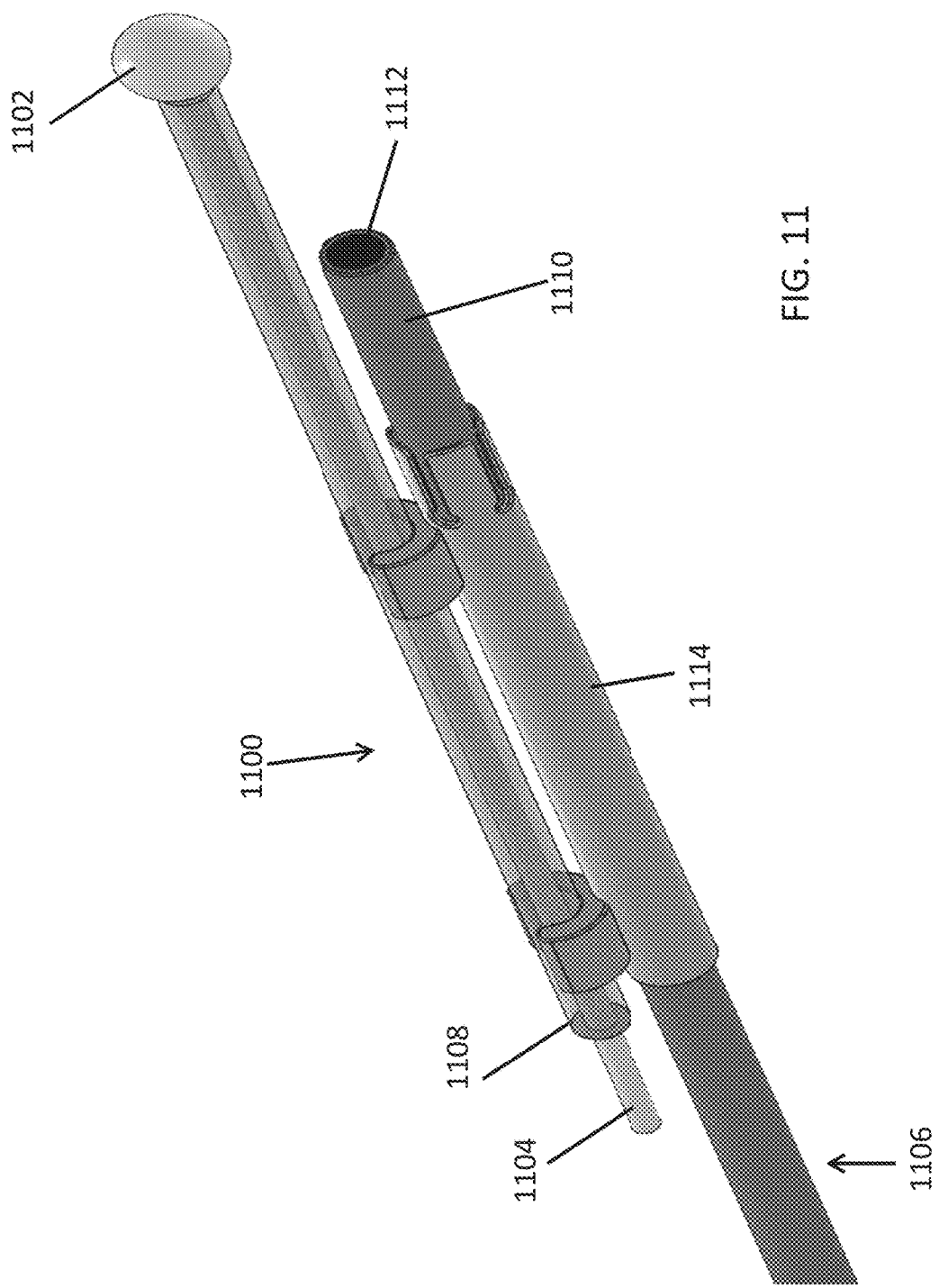

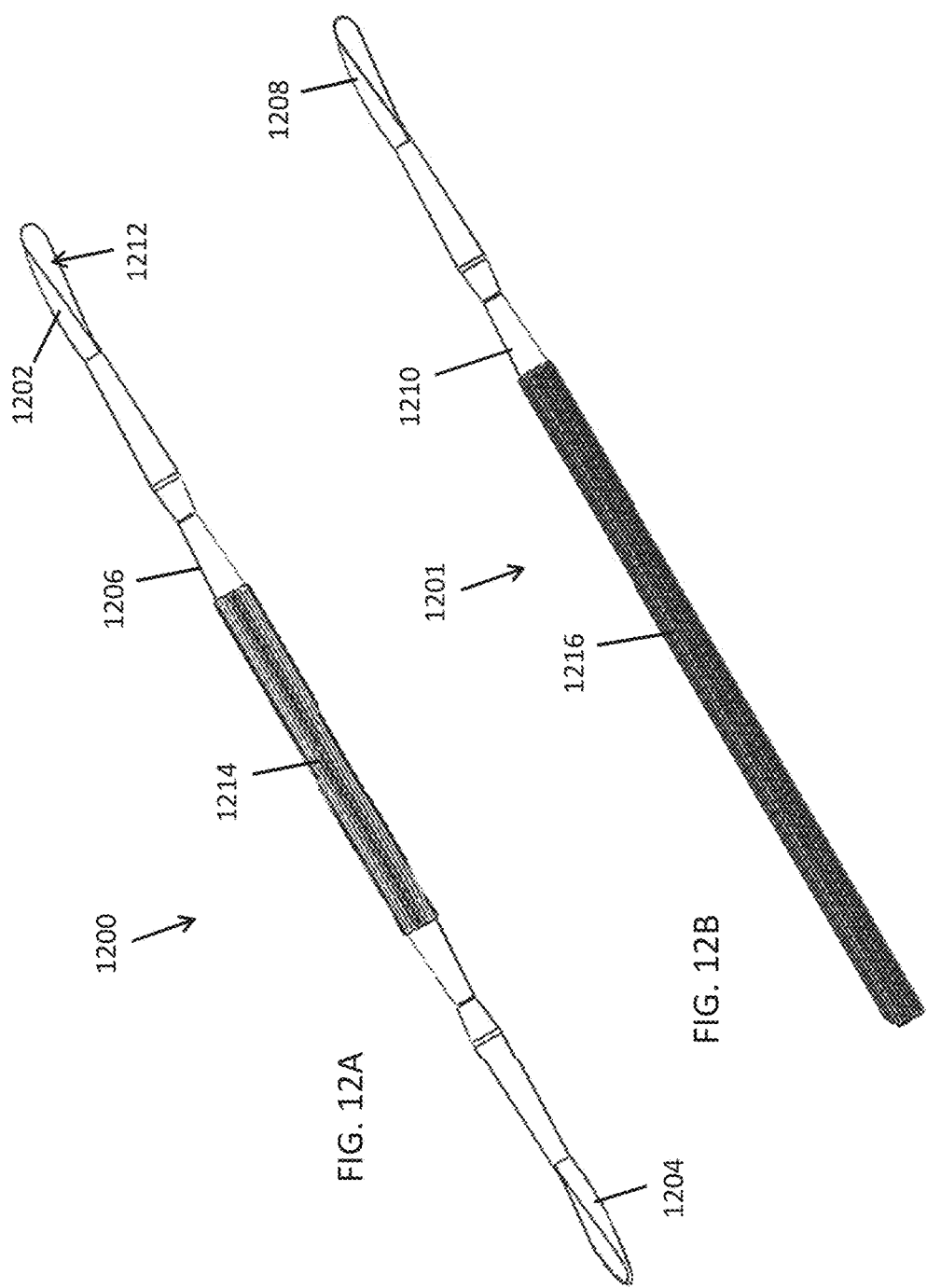

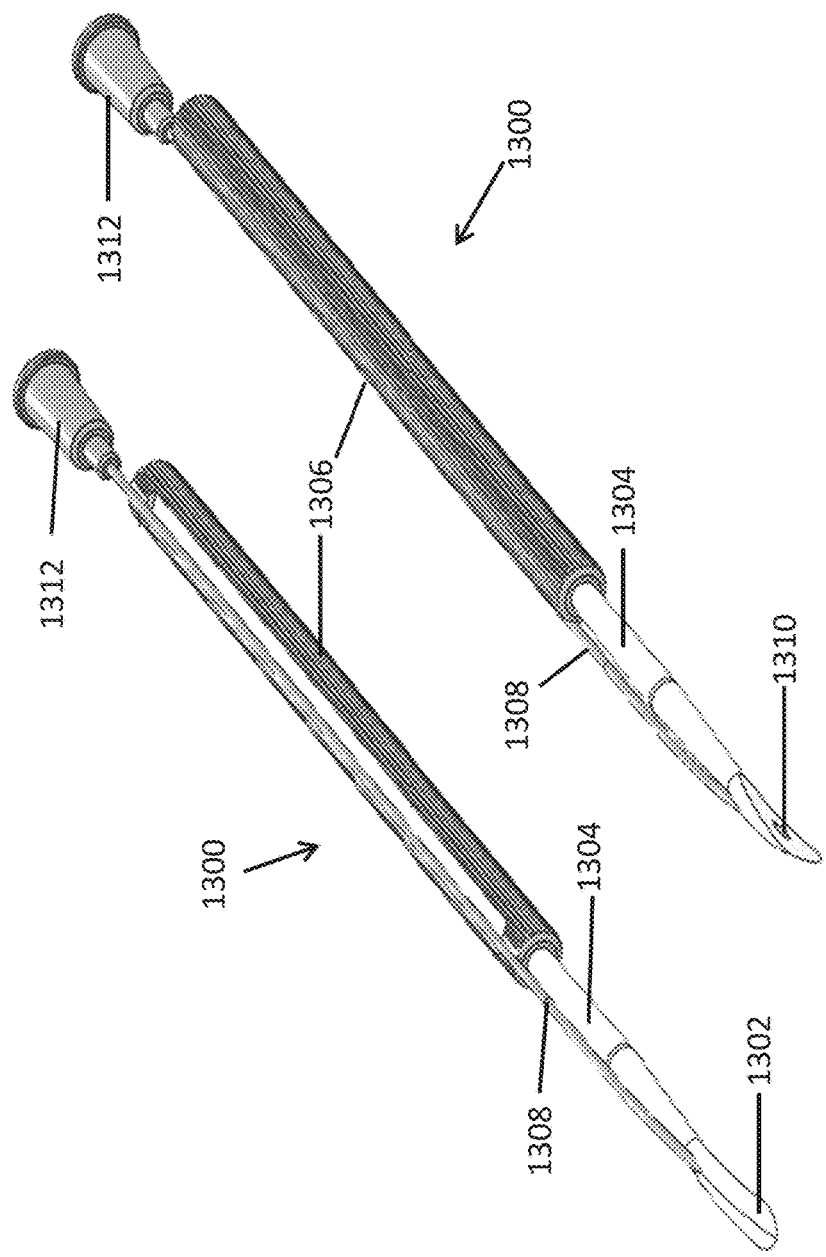

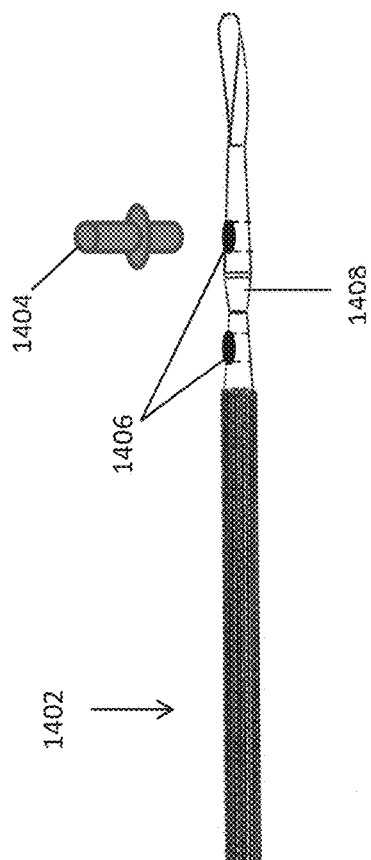
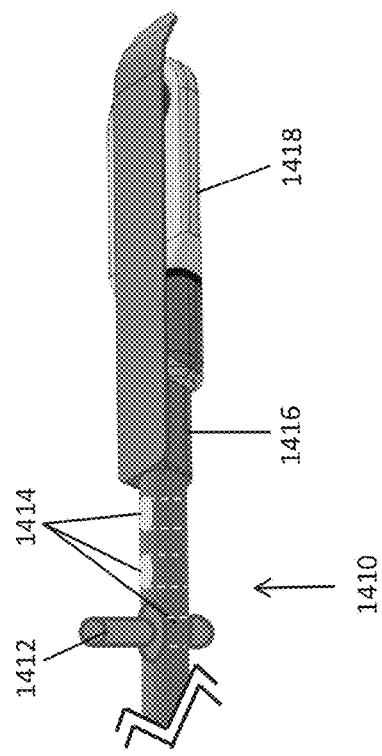
FIG. 14A
FIG. 14B

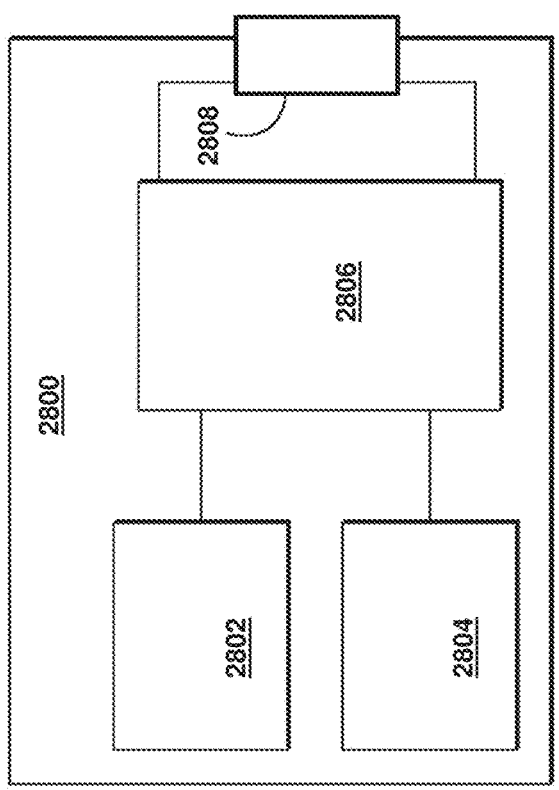
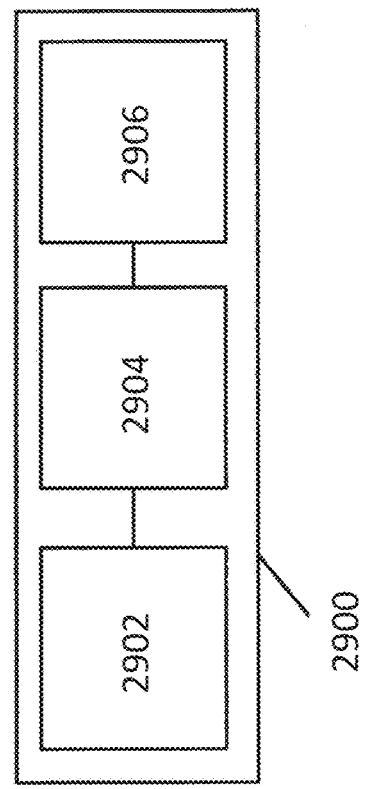

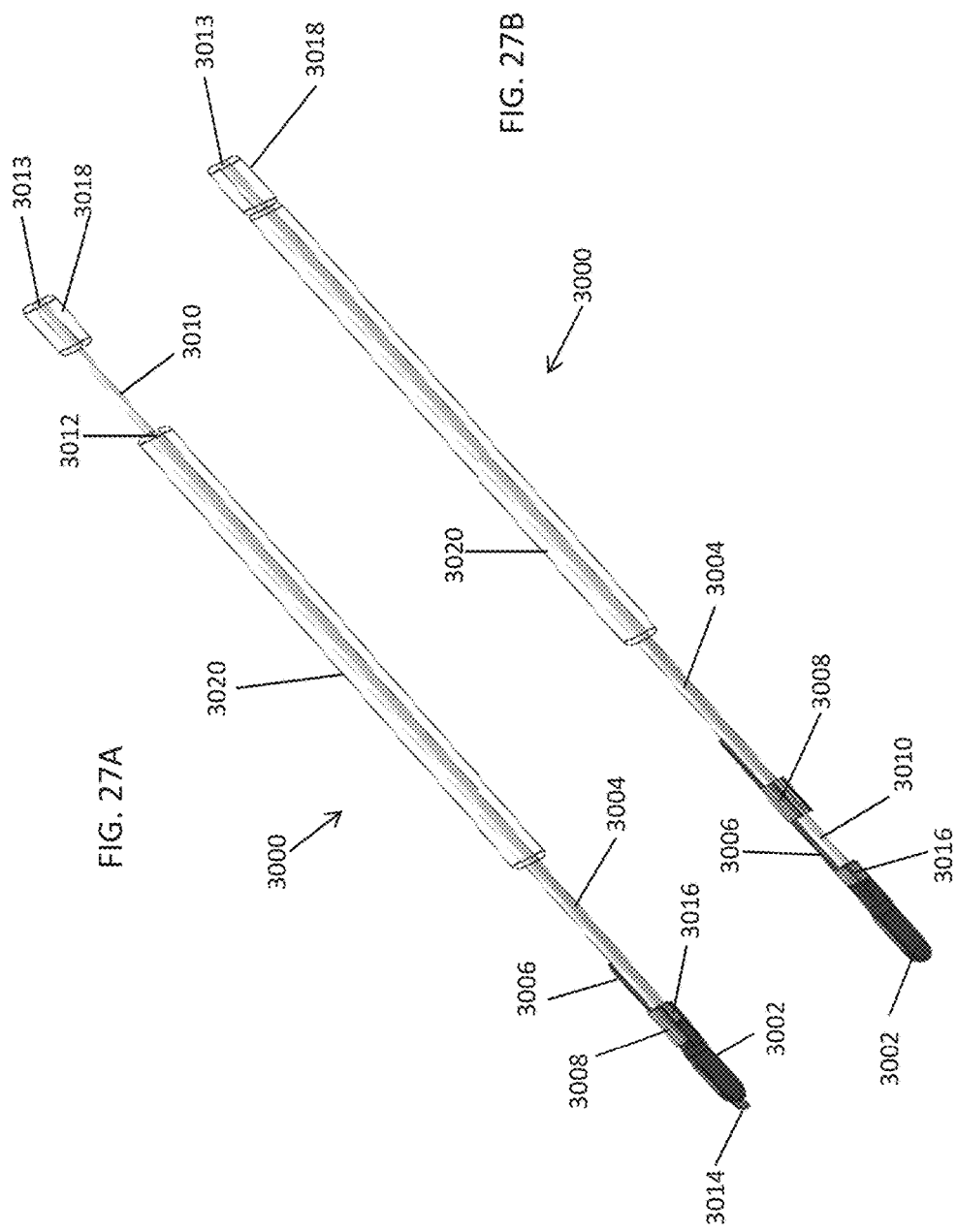

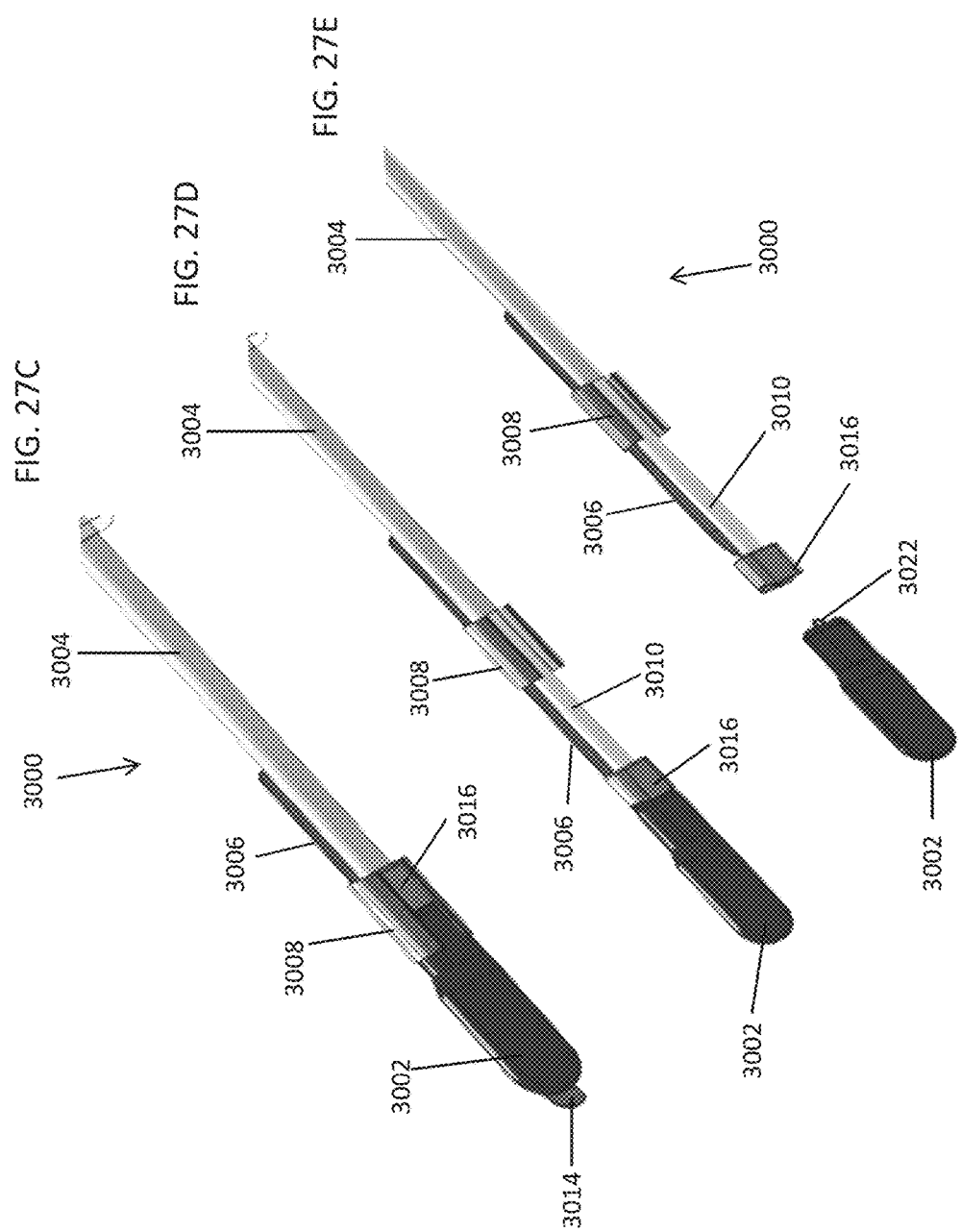

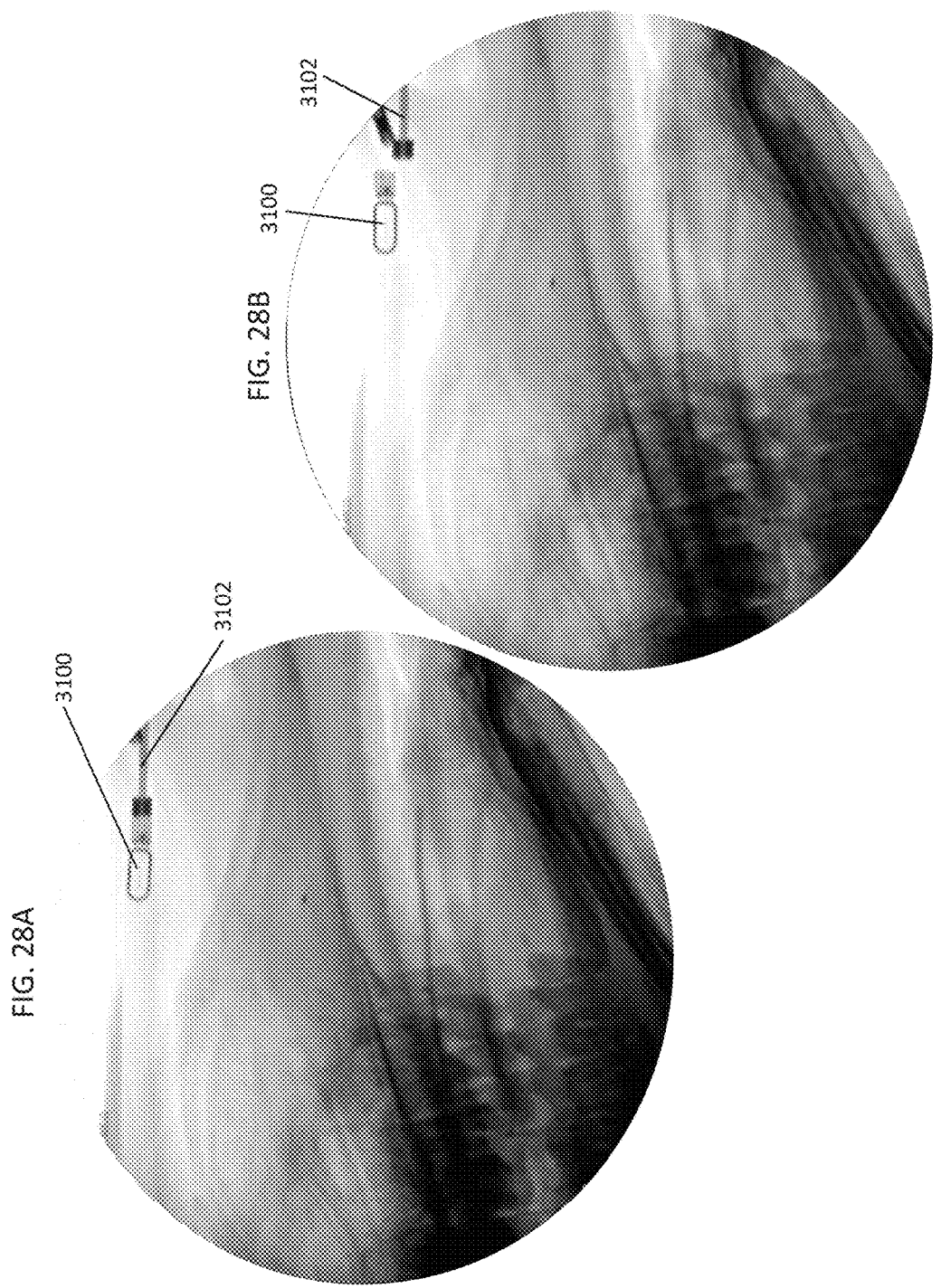

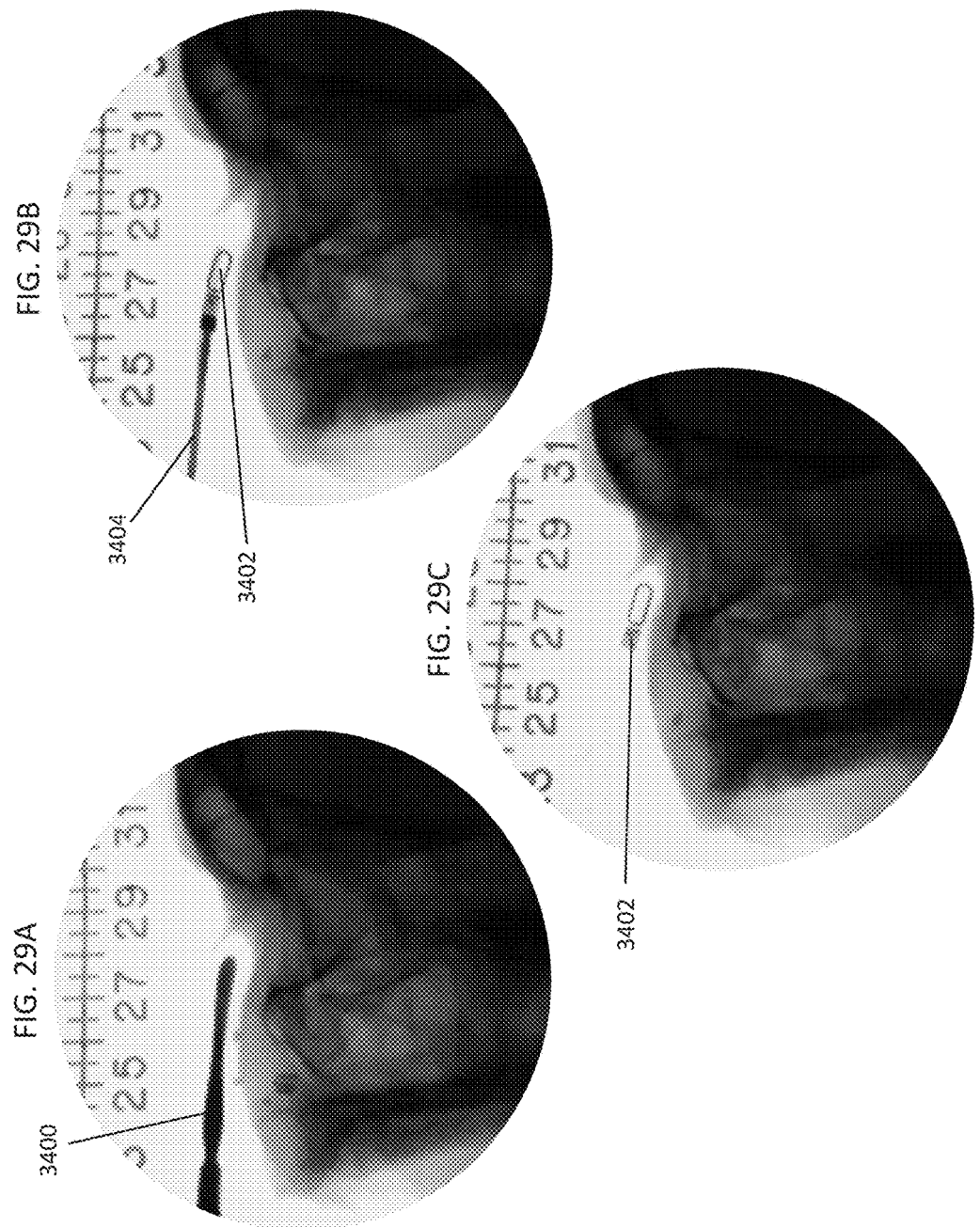

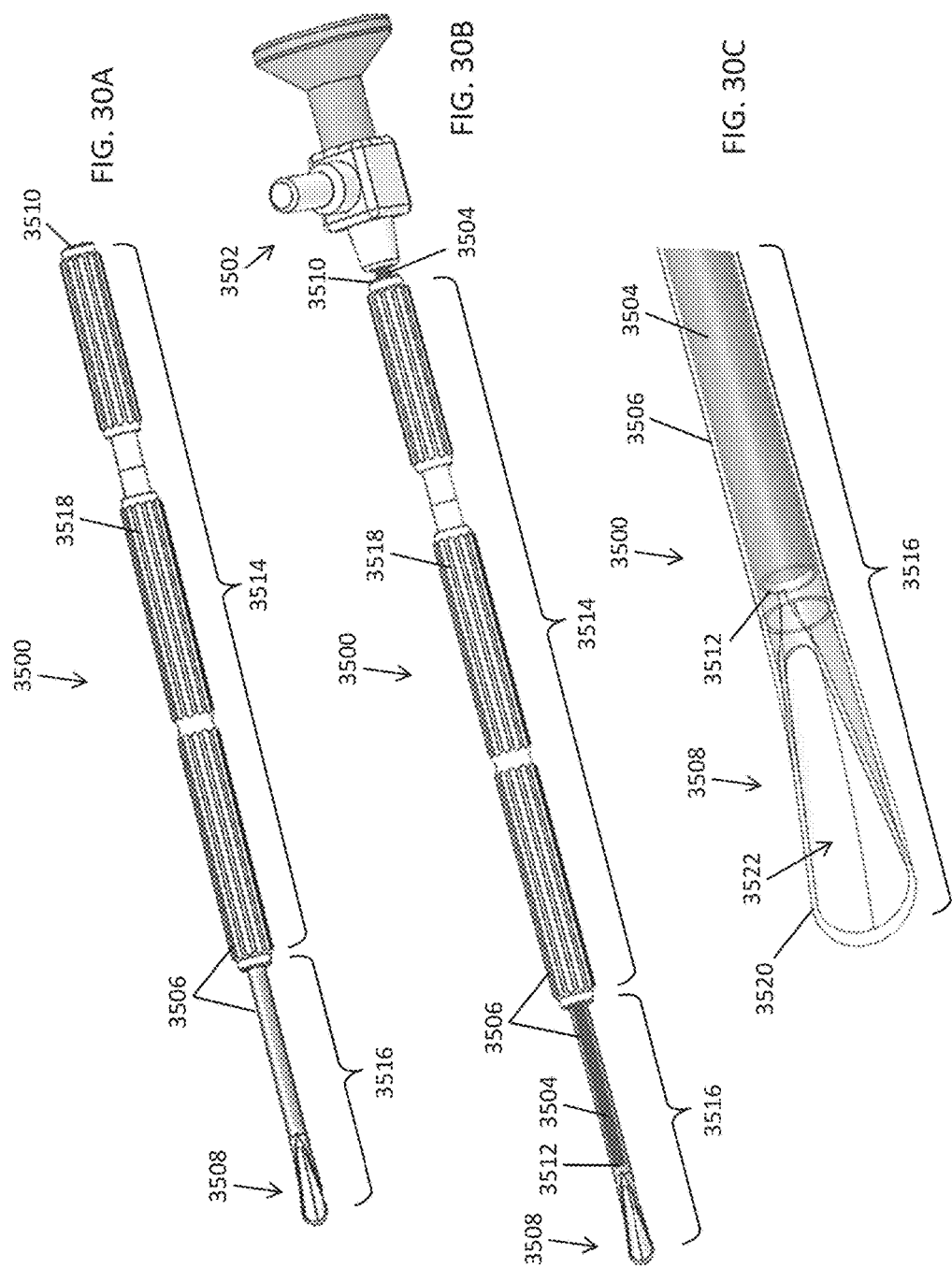

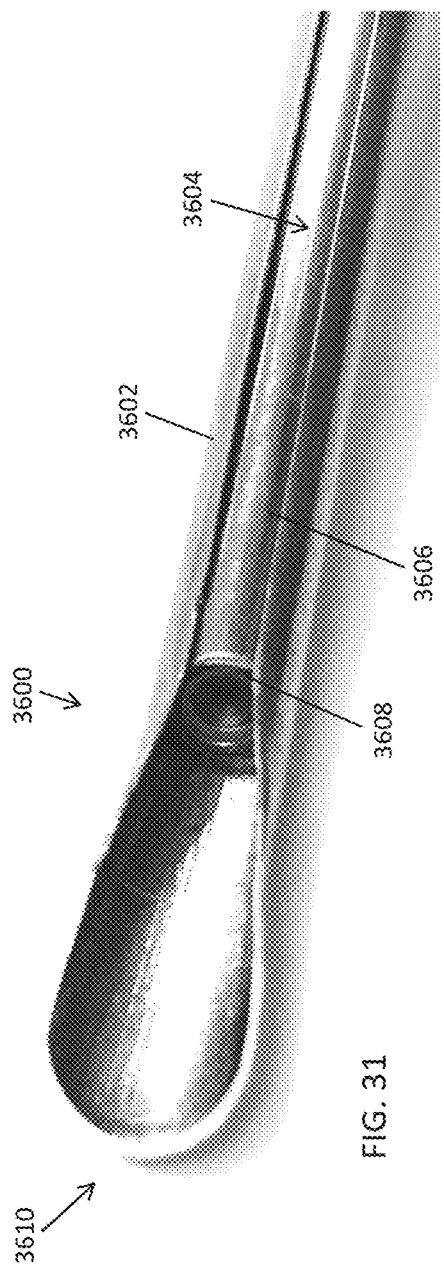
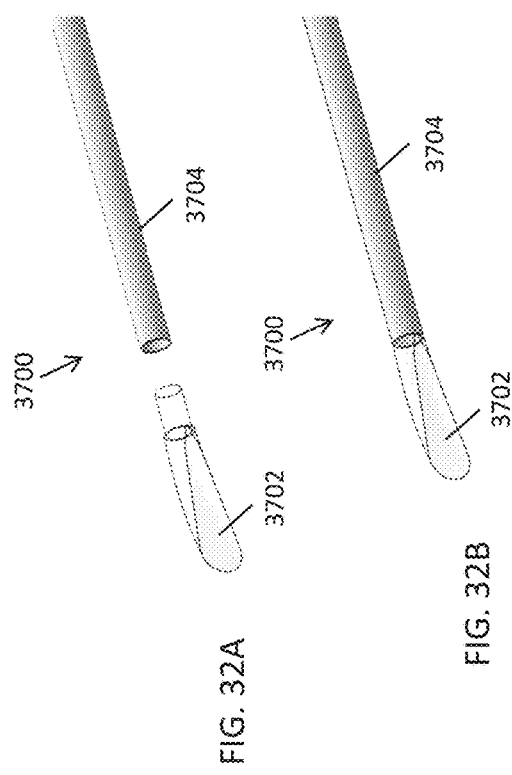
FIG. 31
FIG. 32A
FIG. 32B

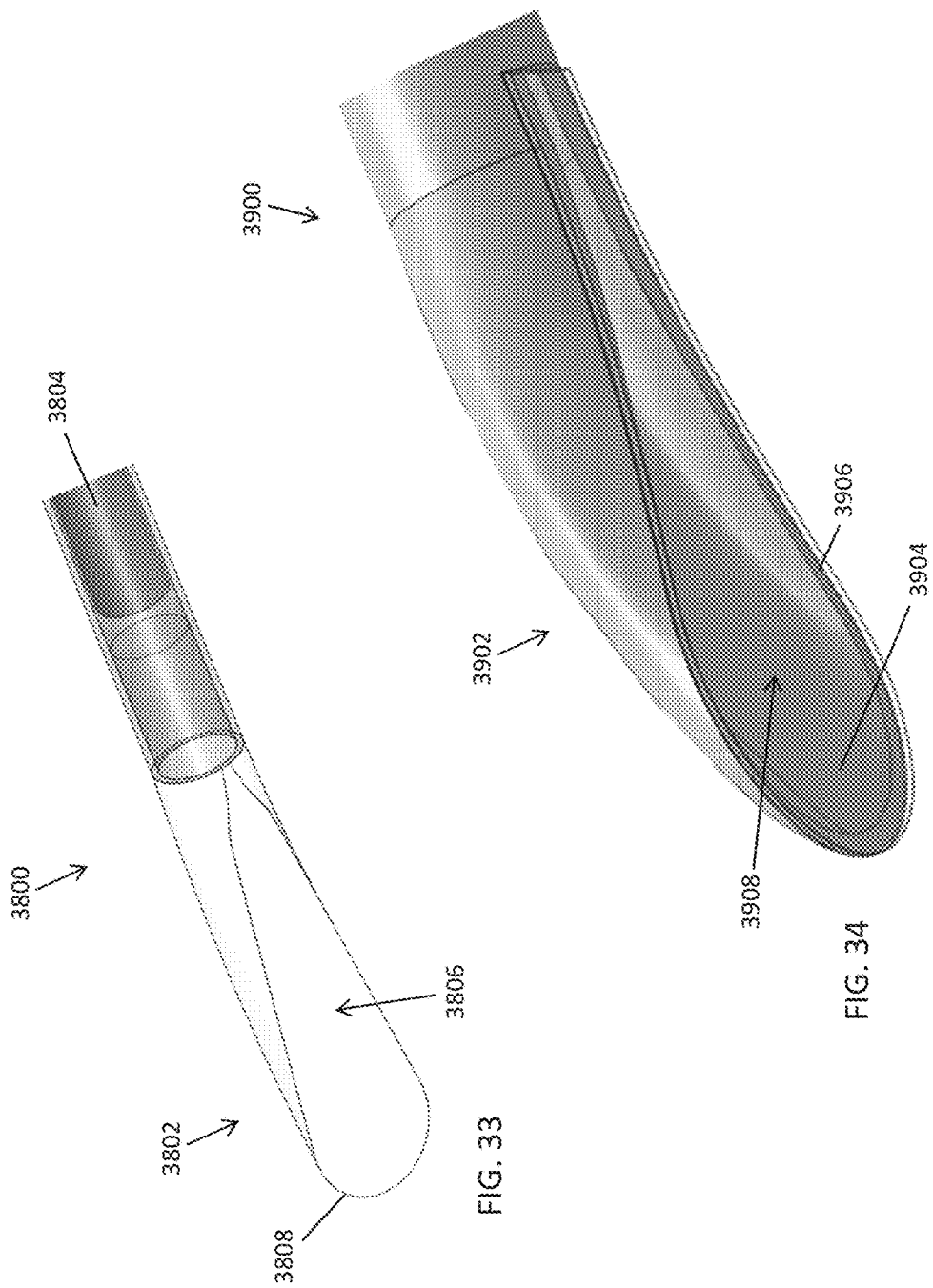

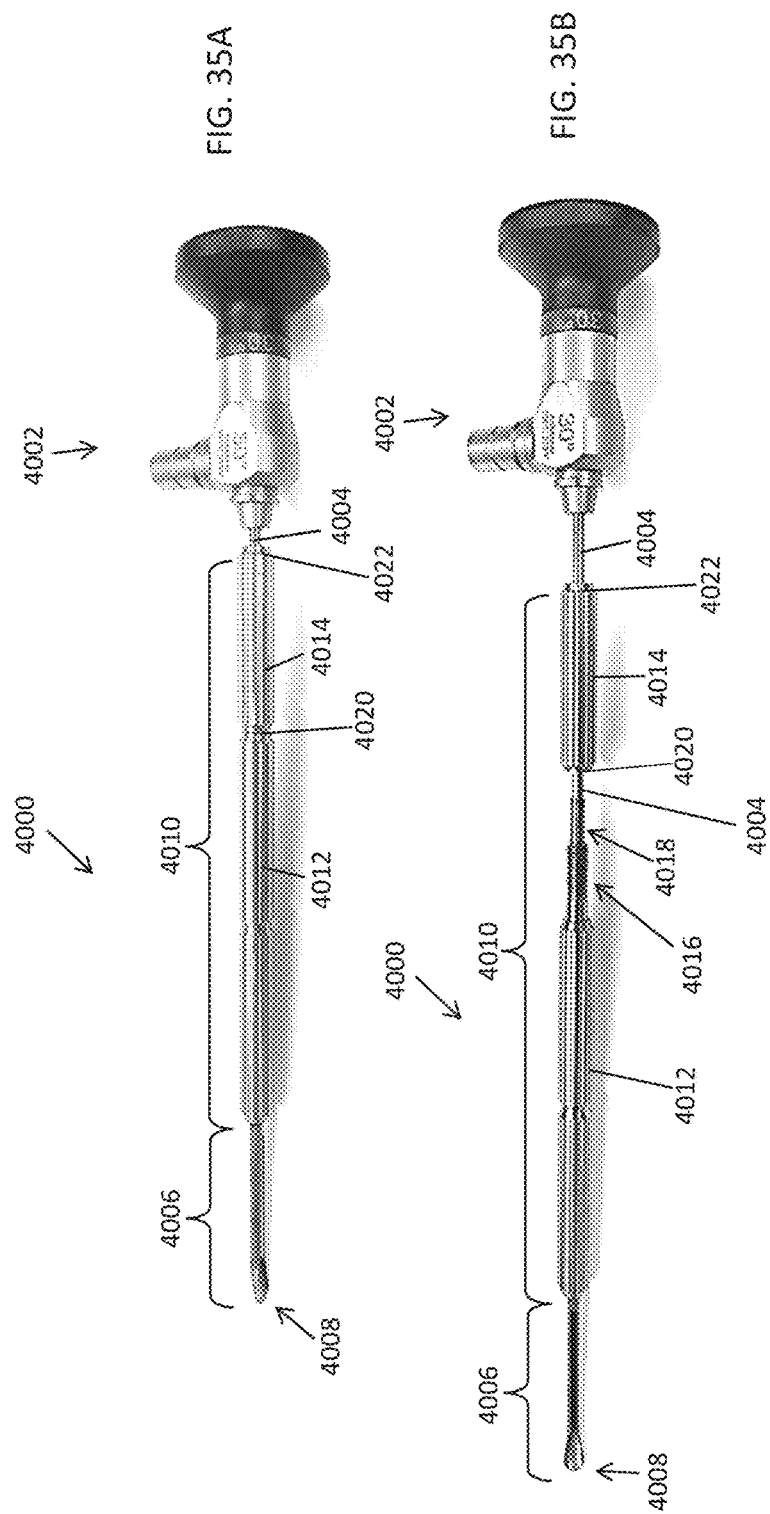

IMPLANTABLE NASAL STIMULATOR SYSTEMS AND METHODS

CROSS-REFERENCE TO RELATED APPLICATIONS

This application claims priority to U.S. Provisional Application No. 62/067,391, filed on Oct. 22, 2014, and titled "IMPLANTABLE NASAL STIMULATOR SYSTEMS AND METHODS," which is hereby incorporated by reference in its entirety.

FIELD

The present invention relates generally to systems, devices, and methods for implanting a nasal stimulator into nasal tissue and electrically stimulating nasal tissue for the treatment of indications such as dry eye.

BACKGROUND

Dry Eye Disease ("DED") is a condition that affects millions of people worldwide. More than 40 million people in North America have some form of dry eye, and many millions more suffer worldwide. DED results from the disruption of the natural tear film on the surface of the eye, and can result in ocular discomfort, visual disturbance and a reduction in vision-related quality of life. Activities of daily living such as driving, computer use, housework and reading have also been shown to be negatively impacted by DED. Patients with severe cases of DED are at risk for serious ocular health deficiencies such as corneal ulceration, and can experience a quality of life deficiency comparable to that of moderate-severe angina.

DED is progressive in nature, and fundamentally results from insufficient tear coverage on the surface of the eye. This poor tear coverage prevents healthy gas exchange and nutrient transport for the ocular surface, promotes cellular desiccation and creates a poor refractive surface for vision. Poor tear coverage typically results from: 1) insufficient aqueous tear production from the lacrimal glands (e.g. secondary to post-menopausal hormonal deficiency, autoimmune disease, LASIK surgery, etc.), and/or 2) excessive evaporation of aqueous tear resulting from dysfunction of the meibomian glands. Low tear volume causes a hyperosmolar environment that induces an inflamed state of the ocular surface. This inflammatory response induces apoptosis of the surface cells which in turn prevents proper distribution of the tear film on the ocular surface so that any given tear volume is rendered less effective. This initiates a vicious cycle where more inflammation can ensue causing more surface cell damage, etc. Additionally, the neural control loop, which controls reflex tear activation, is disrupted because the sensory neurons in the surface of the eye are damaged. As a result, fewer tears are secreted and a second vicious cycle develops that results in further progression of the disease (fewer tears cause nerve cell loss, which results in fewer tears, etc.).

There is a wide spectrum of treatments for DED, although without substantial efficacy for treatment of the condition. Treatment options include: artificial tear substitutes, ointments, gels, warm compresses, environmental modification, topical cyclosporine, omega-3 fatty acid supplements, punctal plugs and moisture chamber goggles. Patients with severe disease may further be treated with punctal cautery, systemic cholinergic agonists, systemic anti-inflammatory agents, mucolytic agents, autologous serum tears, PROSE scleral contact lenses and tarsorrhaphy. Despite these treatment options, DED continues to be considered one of the most poorly treated diseases in ophthalmology. Accordingly, it would be desirable to have a more effective treatment for dry eye.

Strategies described herein for treatment of DED take advantage of the nasolacrimal reflex. The nasolacrimal reflex is a well-established pathway by which nasal stimuli promote tear production. Electrical stimulation applied to sensory neurons in the nasal cavity may activate the nasolacrimal reflex and thereby increase tear production. Devices and methods to deliver electrical stimuli to areas of the nasal cavity are therefore promising alternatives to the current treatment options for DED.

BRIEF SUMMARY

Described here are systems, devices, and methods for implanting a nasal stimulator into nasal tissue and electrically stimulating nasal tissue. In some variations, the methods described here comprise methods of tear production in a patient. In some variations, the methods comprise implanting a microstimulator into nasal tissue and delivering an electrical stimulus via the microstimulator to produce tears. In some variations, the electrical stimulus is pulsed. In some variations, the electrical stimulus comprises a biphasic symmetric pulse waveform. In some variations, the frequency of the biphasic pulse waveform is between 20 Hz and 80 Hz. In some variations, the electrical stimulus has a waveform with a varying pulse width. In some variations, the electrical stimulus has a waveform with a varying frequency. In some variations, the electrical stimulus has a waveform with a varying amplitude.

In some variations, the methods described here comprise methods for delivering a microstimulator into nasal tissue of a patient. In some variations, the methods comprise identifying an implantation site in the nasal tissue, forming a pocket in the nasal tissue at the implantation site, and inserting a microstimulator into the pocket. In some variations, at least a portion of the pocket is located adjacent to the anterior ethmoidal nerve. In some variations, identifying the implantation site comprises electrically stimulating the nasal tissue at at least one location, and observing or recording a response to electrically stimulating the nasal tissue at the at least one location. In some variations, an electrical probe is used to electrically stimulate the nasal tissue. In some variations, the electrical probe comprises an endoscope and an electrode coupled to the endoscope. In some variations, the response comprises one or more of tearing, sneezing, and paresthesia. In some variations, the pocket is substantially between the mucosal layer and the nasal septum. In some variations, forming the pocket comprises incising the nasal tissue to create a pocket opening and extending the pocket from the pocket opening. In some of these variations, the pocket is extended using a dissection tool comprising a shaft, a blade at a first end of the shaft, and a suction opening extending through a portion of the blade. In some variations, the pocket is extended using a dissection tool comprising a shaft with a distal end and a proximal end, a blade positioned at the distal end of the shaft, and a lumen, where the lumen extends distally from an opening at the proximal end of the shaft, and where the lumen is configured to receive an endoscope shaft therewithin. In some of these variations, the dissection tool further comprises a compressible section configured to change a diameter of the lumen in order to releasably attach the dissection tool to the endoscope shaft. In some variations, an implantation tool is used to insert the microstimulator into the pocket. In some variations the implantation tool comprises a retractable cover, and the retractable cover enters the pocket before the microstimulator. In some variations, a device used to perform the method comprises a depth stop to indicate a distance relative to a distal end of the device. In some variations, the microstimulator is tested before it is inserted into the pocket. In some variations, the methods further comprise repositioning or removing the microstimulator after it has been inserted into the pocket. In some variations the implantation site is marked with a dye before the pocket is formed.

In some variations, the methods described here comprise methods of improving ocular surface health in a patient. In some variations, the methods comprise implanting a microstimulator into nasal tissue and delivering an electrical stimulus via the microstimulator to produce tears.

In some variations, the systems described here comprise systems for implanting a microstimulator into nasal tissue. In some variations, the systems comprise a microstimulator configured to be implanted into nasal tissue and an implantation tool. In some variations, the microstimulator is releasably attached to the implantation tool. In some variations, the microstimulator is releasably attached to the implantation tool with static friction, and the microstimulator is released from the implantation tool by overcoming the static friction. In some variations, the microstimulator is releasably attached to the implantation tool via tension, and the microstimulator is released from the implantation tool by releasing the tension. In some variations, the implantation tool comprises a retractable cover. In some variations, the retractable cover is movable relative the microstimulator between a first position and a second position, where at least a portion of the retractable cover covers a portion of the microstimulator in the first position. In some variations, the systems further comprise an electrical probe, and the electrical probe comprises an endoscope coupled to at least one electrode. In some variations, the systems further comprise a dissection tool, and the dissection tool comprises a curved blade, a suction lumen, and an opening in the curved blade in fluid communication with the suction lumen. In some variations, the implantation tool comprises a depth stop to mechanically prevent advancement of the implantation tool into a nasal cavity past the depth stop. In some variations, the dissection tool comprises a depth stop to mechanically prevent advancement of the dissection tool into a nasal cavity past the depth stop. In some variations, the implantation tool comprises a depth marking to visually indicate a distance the implantation tool has been advanced into a tissue pocket or a nasal cavity. In some variations, the dissection tool comprises a depth marking to visually indicate a distance the dissection tool has been advanced into a tissue pocket or a nasal cavity.

In some variations, the devices described here comprise devices for atraumatically electrically stimulating nerve tissue in a cavity. In some variations, devices comprise at least one electrode and a visualization tool, where the at least one electrode is coupled to the visualization tool. In some variations, the visualization tool is an endoscope. In some variations, the device further comprises a conductive shaft that is attached to the at least one electrode, and the visualization tool is coupled to the conductive shaft.

In some variations, the devices described here comprise devices for dissecting tissue. In some variations, the devices comprise a shaft, a blade at a first end of the shaft, a suction opening extending through a portion of the blade, and a tube extending from the suction opening to a port. In some variations, the tube is coupled to an exterior surface of the shaft. In some variations, the shaft comprises a lumen and the tube is at least partially disposed in the shaft lumen. In some variations, the blade comprises a curve.

In some variations, the devices described here comprise devices for dissecting tissue. Some of these devices comprise a shaft comprising a distal end and a proximal end, a blade positioned at the distal end of the shaft, and a lumen, where the lumen extends distally from an opening at the proximal end of the shaft, and the lumen is configured to receive an endoscope shaft therewithin. In some variations, at least a portion of the blade is transparent. In some variations, the blade comprises an edge and a face, and the face is an area at least partially enclosed by the edge. In some variations, the face of the blade is an opening, and in some of these variations, the blade further comprises a window that at least partially covers the face. In some variations where the face is an opening, the device further comprises a barrier positioned at least partially within a distal portion of the lumen, and the barrier is configured to prevent obstruction of a view from the endoscope shaft. In some of these variations, the barrier comprises a liquid polymer configured to solidify after delivery into the device. In some variations, the face is a solid surface that is integral with the edge, and the blade does not comprise any external openings. In some variations, the device comprises a sleeve configured to cover at least a portion of the blade. In some variations, the device comprises a least one tube configured to provide irrigation or suction. In some variations, the device comprises an attachment mechanism configured to releasably attach the device to the endoscope shaft. In some of these variations, the attachment mechanism comprises a compressible section configured to change a diameter of the lumen. In some of these variations, the attachment mechanism comprises a screw portion and a nut portion, and the screw portion and the nut portion comprise mating threads. In some of these variations, the attachment mechanism is configured to compress the compressible section and decrease the diameter of the lumen when the screw portion and the nut portion are screwed together. In some variations, the compressible section comprises deflectable wings. In some variations, the screw portion comprises the compressible section. In some of these variations, a proximal section of the shaft comprises the screw portion and the nut portion.

BRIEF DESCRIPTION OF THE DRAWINGS

FIG. 1A shows a perspective view of a variation of an implantation tool and a microstimulator described here. FIG. 1B shows a magnified view of a distal portion of the implantation tool and microstimulator of FIG. 1A.

FIG. 2A shows a perspective view of a first side of a variation of a microstimulator described here. FIG. 2B shows a perspective view of a distal portion of a variation of an implantation tool described here and a second side of the microstimulator of FIG. 2A.

FIGS. 3A-3C show perspective views of a variation of a microstimulator described here.

FIGS. 4A and 4B show perspective views of portions of a variation of an implantation tool and a microstimulator described here. FIG. 4C shows a perspective view of a proximal portion of a variation of an implantation tool described here.

FIGS. 5A-5C show perspective views of a distal portion of a variation of an implantation tool and a microstimulator described here.

FIGS. 6A-6C show perspective views of a variation of an implantation tool and a microstimulator described here.

FIGS. 7A and 7B show perspective views of a distal portion of the implantation tool and microstimulator of FIGS. 6A-6C.

FIGS. 8A-8C show perspective views of a cross-section of the implantation tool and microstimulator of FIGS. 6A-6C.

FIG. 11 shows a perspective view of a variation of an electrical probe described here.

FIGS. 12A and 12B show perspective views of variations of dissection tools described here.

FIGS. 13A and 13B show perspective views of a variation of a dissection tool described here.

FIGS. 14A and 14B show perspective views of variations of a dissection tool and a distal portion of an implantation tool, respectively, comprising depth stops described here.

FIG. 25 shows a block diagram of a variation of a controller circuit suitable for a controller described here.

FIG. 26 shows a block diagram of another variation of a controller circuit suitable for a controller described here.

FIGS. 27A-27E show perspective views of a variation of an implantation tool and microstimulator described here.

FIGS. 28A and 28B show fluoroscopic images of a portion of a goat skull with a variation of a microstimulator and an implantation tool described here, releasably attached and detached, respectively.

FIGS. 29A-29C show fluoroscopic images of a procedure to implant a variation of a microstimulator described here into a human cadaver.

FIGS. 30A-30C show a variation of a dissection tool described here configured for use with an endoscope.

FIG. 31 shows a distal portion of a variation of a dissection tool described here configured for use with an endoscope.

FIGS. 32A and 32B show a distal portion of a variation of a dissection tool described here with an attachable blade.

FIG. 33 shows a distal portion of a variation of a dissection tool described here configured for use with an endoscope.

FIG. 34 shows a distal portion of a variation of a dissection tool described here configured for use with an endoscope.

FIGS. 35A and 35B show a variation of a dissection tool described here configured for use with an endoscope.

DETAILED DESCRIPTION

Figure 2C:
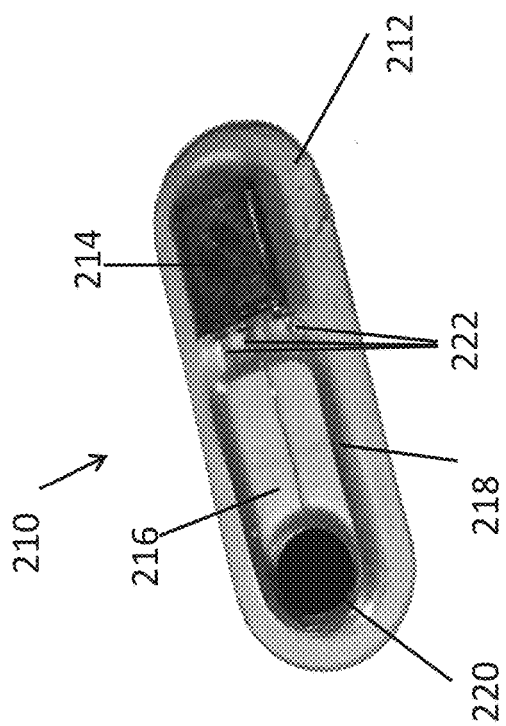
FIG. 2C shows a perspective view of a variation of a microstimulator described here.

The devices, systems, and methods described herein may be used to increase tear production by electrically stimulating nasal tissue with a microstimulator that is surgically implanted into a nasal cavity. The microstimulator may comprise a passive stimulation circuit configured to receive power wirelessly, such as from an external controller, and one or more electrodes to deliver an electrical stimulus to surrounding tissue. Devices and methods are described for implanting the microstimulator in a desired location in the nasal cavity, which in some variations is within a surgically-created tissue pocket adjacent to the nasal septum. For example, an electrical probe for identifying the desired implantation site and dissection tools for creating the nasal tissue pocket are described. Also described are implantation tools configured to deliver the microstimulator through a nostril and into the tissue pocket. In addition, devices and methods are described for increasing tear production after the microstimulator is implanted, which in some variations may be used to treat Dry Eye Disease (DED).

Devices and Systems

FIGS. 1A and 1B show perspective views of one variation of a nasal implant stimulation system (100) described here comprising a microstimulator (101) and an implantation tool (102). FIG. 1A depicts the microstimulator (101) releasably attached to a distal end of the implantation tool (102), and FIG. 1B shows a magnified view of the microstimulator (101) and a distal portion of the implantation tool (102). The microstimulator may be configured to be implanted into nasal tissue, where it may generate and deliver an electrical stimulus. As shown in FIG. 1B, the microstimulator (101) may comprise a housing (103) and an extension (104). The housing may comprise a stimulation circuit (not pictured), and the extension may comprise one or more electrodes (105).

The implantation tool (102) may be configured to position the microstimulator (101) in a nasal cavity and release the microstimulator into a tissue pocket. The implantation tool may comprise a shaft (106), a handle (108), and one or more features for releasably attaching the microstimulator (101). For example, the implantation tool (102) shown in FIGS. 1A and 1B comprises a tension system to releasably attach the microstimulator. The tension system may comprise a tensioning element (111) (e.g., a string, suture, wire, or the like) that may attach to the microstimulator and hold it against a contact surface (107) at a distal end of the implantation tool shaft (106). The tensioning element may extend through a lumen of the implantation tool shaft to its proximal end, where the tensioning element may be secured by a connector, such as a knob (112). This may allow tension to be maintained in the tensioning element to hold the microstimulator in place. In order to detach the microstimulator from the implantation tool, tension in the tensioning element may be released, such as by cutting the tensioning element.

The implantation tool (102) may comprise one or more features to protect the microstimulator (101) during implantation and/or facilitate the formation of a pocket in tissue for the implant. For example, the implantation tool (102) may comprise a retractable cover (109) that may be slidable relative to the shaft (106). The retractable cover may be slidable between a retracted, proximal position, which is shown in FIGS. 1A and 1B, and an advanced, distal position (not shown). When the retractable cover is in the retracted position, an electrode (105) of the microstimulator may be exposed, and the microstimulator may be detached from the implantation tool. When the retractable cover is in the advanced position, the electrode may be covered and protected, and the microstimulator may be advanced into a nostril and positioned at an implantation site. In some variations, when the retractable cover is in the advanced position, a portion of the retractable cover may extend distal to the microstimulator. This may, for example, protect the microstimulator and/or allow the retractable cover to be used for creating and/or opening a tissue pocket.

A nasal microstimulator implantation system may additionally or alternatively comprise other tools, which are described in more detail herein. For example, tools are described that may help to select an implantation site for a microstimulator, such as an electrical probe. The electrical probe may comprise a conductive shaft to electrically stimulate areas of the nasal cavity in order to locate a specific site that produces tearing when stimulated. The electrical probe may also comprise an endoscope to visualize the areas that are stimulated. In some variations, the system may comprise one or more devices to dissect (incise, separate, elevate, and/or the like) nasal tissue in order to form a tissue pocket to receive the microstimulator. For example, a dissection tool may comprise a sharp blade for incising tissue to make an opening for the tissue pocket and/or a blunt blade for extending the tissue pocket. The dissection tool may be configured to provide suction and/or configured to be used with an endoscope to improve visualization around the blade.

Micro Stimulator

FIG. 2A and FIG. 2B show perspective views of opposite first and second sides of a microstimulator (200), respectively. In FIG. 2A, the microstimulator is depicted alone, and in FIG. 2B, it is depicted attached to an implantation tool (201). As shown, the microstimulator (200) may comprise a housing (202) and an extension (204) connected to the housing, although in other variations the housing may be partially or completely contained within the extension.

The shape and size of the microstimulator may aid in atraumatic insertion of the device into nasal tissue. Generally, the shape of a microstimulator may be flat and thin. As will be discussed in more detail herein, during implantation, the microstimulator may be inserted into a tissue pocket within the nasal submucosal layer. A flat, thin shape may decrease the risk of catching, stretching, or otherwise traumatizing nasal tissue (e.g., nasal septum, submucosa) during implantation. As seen in FIGS. 2A, 2B, and 3A-3C, the microstimulator may comprise one or more rounded edges which may also reduce the risk of tissue damage as the microstimulator is advanced into or past tissue. One or more portions of the microstimulator (e.g., an extension) may be formed from a flexible material such as silicone and/or may be a molded component, such as a molded silicone. The materials may allow the microstimulator to conform to one or more portions of the anatomy (e.g., the nasal septum) and/or prevent trauma during implantation.

The microstimulator may be small enough to be inserted through a nostril and implanted within a layer of submucosa adjacent to the nasal septum or a turbinate without significantly interfering with the passage of air or fluid through the nasal cavity. In some variations the dimensions may be less than about 30 mm by about 10 mm by about 5 mm (L×W×H). In some of these variations, the dimensions may be about 15 mm-25 mm by about 3 mm-7 mm by about 1 mm-3 mm (L×W×H). In some of these variations, the dimensions may be about 17 mm by about 5 mm by about 2 mm (L×W×H). In variations of the microstimulator comprising a housing adjacent to an extension, such as shown in FIGS. 2A-2C, the thickness of the extension (203) may be less than that of the housing (202) and may gradually increase to the thickness of the housing. The width of the extension may be greater than the width of the housing and may taper to the width of the housing, as seen in FIGS. 2A and 2B. In some variations, the housing may have the same width as the extension, or the housing may be wider than the extension. In some variations, the microstimulator may be encapsulated in a coating. A coating, such as silicone, provides electrical insulation, waterproofing, biocompatibility, and/or safety (e.g., rounded edges, lubricious surface that slides easily over the nasal septum). FIG. 2C shows a variation of a microstimulator (210) encapsulated in a coating (212).

The microstimulator may comprise one or more connectors, which may facilitate attachment of the microstimulator to another device. For example, one or more connectors may attach the microstimulator to an implantation tool and/or a tool for minimally-invasive retrieval or repositioning. As shown in FIG. 2A, one variation of the connector comprises an eyelet (204) at the proximal end of the housing. This eyelet may attach to an implantation tool and/or a tool for retrieval or repositioning. In some variations, an eyelet may be recessed into a portion of the housing or extension such that the eyelet does not extend beyond the dimensions of the microstimulator. It should be appreciated that in some variations, the connector or connectors may be located in other positions on the microstimulator (e.g., other positions on the housing or on the extension) or have other forms (e.g., hook, slot, or magnet). In some variations, different connectors may be used to attach the microstimulator to different devices, whereas in other variations, the same one or more connectors may be used with different devices.

The housing (202) of the microstimulator (200) may comprise a housing case containing some or all of a stimulation circuit, described in more detail herein. The housing case may be hermetically sealed and may be formed from one or more metals (e.g., titanium) or other biocompatible materials.

In some variations, the stimulation circuit may comprise one or more passive stimulation circuits in which the device does not include any internal logic or intelligence (e.g., ASICs, microcontrollers or the like). In some of these variations, the microstimulator does not have an internal battery. In these variations, the microstimulator may include only a dissipation circuit that receives an output signal from a controller, generates a current based on the received signal, and delivers the generated current. The dissipation circuit may contain one or more signal conditioning units which may shape or otherwise modify the signal received from a controller. In some variations, the circuit may be configured to receive energy from an external source, rectify the energy into a stimulation pulse, and allow for passive charge balancing. In some variations the stimulation circuit may comprise one or more current rectifiers, one or more amplitude limiting units, and one or more ramping control units, combinations thereof, or the like. In some variations, the dissipation circuit may comprise one or more adjustable/tunable components.

In other variations, a microstimulator may include internal logic which may be used to shape or modify a signal received from a controller. In some of these variations, the microstimulator may not include an internal battery, such that operating power is received by the output signal of a controller. In still other variations, the microstimulator may comprise an implantable pulse generator, which may include all of the circuitry necessary to generate and deliver electrical pulses to tissue. The stimulation circuits described here may contain elements which allow a controller to detect one or more operating parameters of the stimulation circuit.

Figure 23:
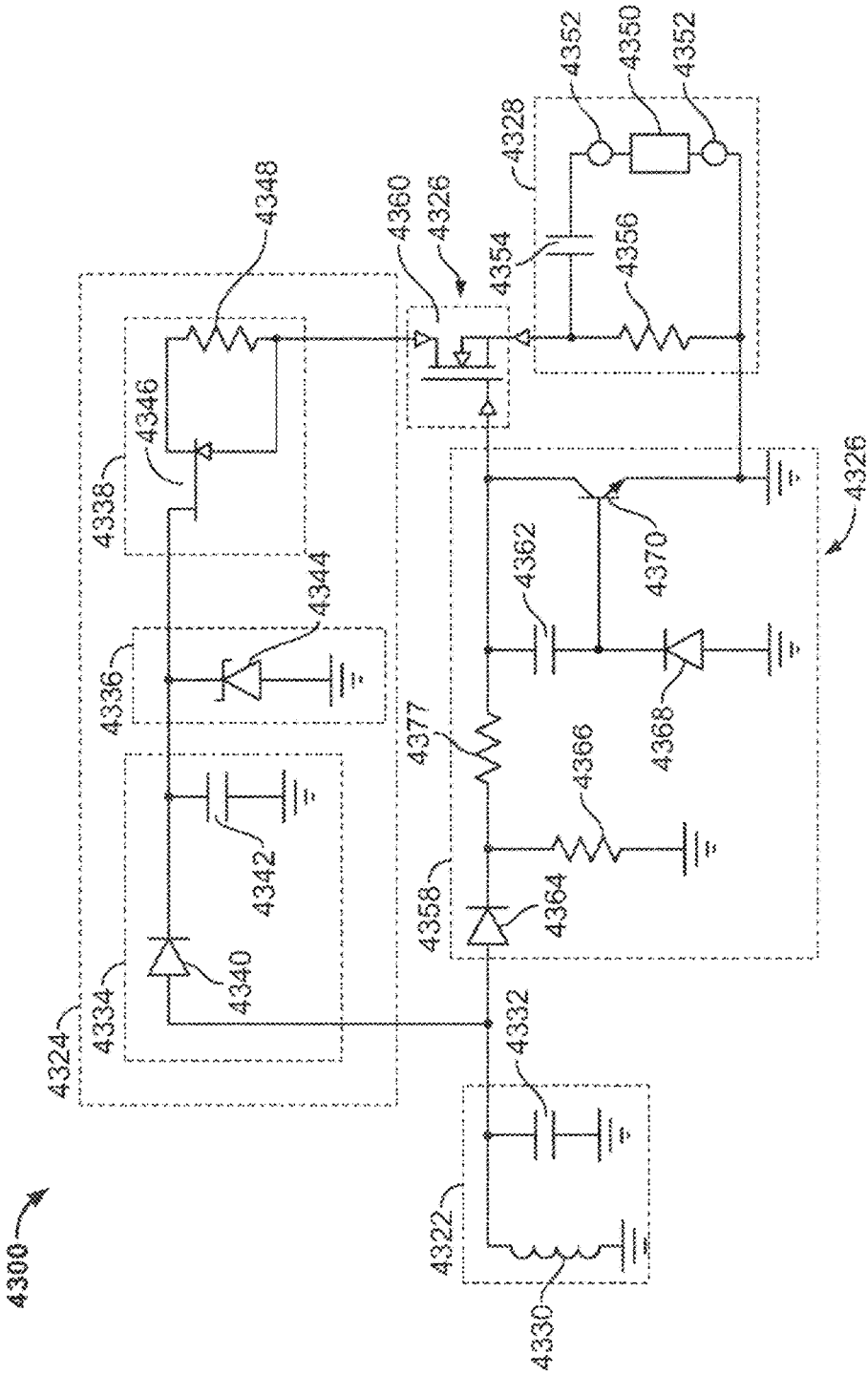
FIG. 23 shows a variation of a passive stimulation circuit suitable for a microstimulator described here.

FIG. 23 depicts a variation of a stimulator circuit (4320) which may be configured to passively ramp a stimulation signal provided by the stimulation circuit. As shown there, stimulator circuit (4320) may comprise a receiving unit (4322), a signal conditioning unit (4324), a ramping control unit (4326), and an output unit (4328). The receiving unit (4322) may be configured to receive an output signal from a controller (not shown), and may transmit the received signal to the signal conditioning unit (4324) and the ramping control unit (4326). In the variation shown in FIG. 23, the receiving unit (4322) may comprise a resonant circuit comprising a coil (4330) connected in parallel with a tuning capacitor (4332). This resonant circuit may be tuned or otherwise configured to receive an output signal that is transmitted at a certain frequency or range of frequencies. It should be appreciated, however, that the receiving unit (4322) may comprise any suitable components that receive an output signal (e.g., a magnetic field, RF signal, optical signal, ultrasound signal, or the like) and generate a current or voltage therefrom.

The signal received by the receiving unit (4322) may be passed to the signal conditioning unit (4324) and the ramping control unit (4326). In the variation shown in FIG. 23, the signal conditioning unit (4324) may comprise a rectification unit (4334), an amplitude control unit (4336), and a current source unit (4338). It should be appreciated that the signal conditioning unit (4324) may include only some of these individual components and/or may contain additional components as desired. In variations that include a rectification unit (4334), the rectification unit (4334) may be configured to convert any alternating current signals to direct current signals. The rectifying unit may be a half-wave rectifier or a full-wave rectifier, and in some instances may be configured to smooth the rectified signal. For example, the variation of rectification unit (4334) shown in FIG. 23 may comprise a half-wave rectifier comprising a diode (4340) and a smoothing capacitor (4342) placed at the output of the half-wave rectifier.

In variations that include an amplitude control unit (4336), the amplitude control unit (4336) may be configured to limit the maximum amplitude of the signal delivered by the output stage (4328). For example, the amplitude control unit (4336) shown in FIG. 23 may comprise a zener diode (4344), which may shunt current away from the signal conditioning unit (4324) when the voltage across the zener diode (4344) exceeds a threshold voltage. It should be appreciated that the amplitude control unit (4336) may comprise any suitable current or voltage limiting elements, which may be positioned in any suitable portion of the stimulator circuit (4300) (e.g., as part of the receiving unit (4322), the signal conditioning unit (4324), the ramping control unit (4326), the output unit (4328), combinations thereof, and the like). In some variations, a stimulation circuit may comprise a plurality of amplitude control units, each of which may limit a different aspect of the generated stimulation signal, or may limit aspects of the generated control signal at different locations.

In variations where the signal conditioning unit (4324) comprises a current source unit (4338), the current source unit (4338) may be configured to act as a voltage-controlled current source which may output a current based on a voltage input received by the current source unit (4338). For example, in some variations (such as that shown in FIG. 23), the current source unit (4338) may comprise a transistor (4346) (e.g., a JFET, MOSFET, BJT) where the gate and the source of the transistor (4340) are connected (e.g., via a resistor (4348) or the like). In some variations, the current source unit (4338) may act as a constant-current source that may provide a constant current when any voltage above a certain threshold is applied to an input of the current source unit (4338). In some variations, a current source unit may comprise one or more current-limiting diodes or the like. In some variations the current source unit (4338) may comprise a current mirror circuit. The current mirror circuit may be symmetric or asymmetric.

Once the received output signal has been conditioned by the signal conditioning unit (4324), the signal may be passed to the output unit (4328). The output unit (4328) may thus deliver the processed signal as an output signal to tissue (4350) via electrodes (4352). In some variations, the output unit (4328) may be configured to allow for passive charge balancing. For example, output unit (4328) may comprise a capacitor (4354) and resistor (4356). The capacitor (4354) may charge when the signal conditioning unit (4324) is delivering current to the output unit (4328) and tissue (4350), and may discharge when the signal conditioning unit (4324) is not delivering current to the output unit (4328), which may allow the output unit (4328) to provide a biphasic, charge-balanced, stimulation signal to tissue (4350). In some variations, the output unit (4328) may comprise a current-limiting device (not shown) or the like, which may limit the magnitude of the balancing current produced by the capacitor (4354).

As mentioned above, the ramping control unit (4326) may be configured to ramp the signal provided from the signal processing unit (4324) to the output unit (4326). As shown in FIG. 23, the ramping control unit (4326) may comprise a charging unit (4358) and a field-effect transistor (4360). The field-effect transistor (4360) may be any suitable transistor (e.g., a MOSFET, BJT, or the like). The signal conditioning unit (4324) and the output unit (4328) may be connected to the source and drain terminals of the field-effect transistor (4360), and the charging unit (4326) may be connected to the gate terminal of the field-effect transistor (4360). As mentioned above, the current that passes between the signal conditioning unit (4324) and the output unit (4328) through the field-effect transistor (4360) may be dependent on a voltage provided by the charging unit (4326) to the gate terminal of the field-effect transistor (4360). As such, the ramping control unit (4326) may be configured to increase the amplitude of the stimulation signal as the charging unit (4326) charges.

The charging unit (4326) may be configured to increase the voltage provided to the field-effect transistor (4360) as the receiving unit (4322) receives an output signal generated by a controller. For example, as shown in FIG. 23, the charging unit (4326) may comprise a capacitor (4362) which may be charged as receiving unit (4322) receives the output signal. As the capacitor (4362) charges, the voltage applied to the field-effect transistor (4360) may increase, which may thereby increase the current that may pass from the signal conditioning unit (4324) to the output unit (4328). This may result in a ramped stimulation signal produced by the microstimulator. In some instances, the charging unit (4326) may comprise a rectifying diode (4364) or other rectification circuit which may rectify the signal received from the receiving unit (4322). Additionally, the charging unit (4326) may comprise one or more additional components (e.g., resistors (4366) and (4377), diode (4368) and transistor (4370), which may control the rate at which the capacitor (4362) charges and discharges. While the stimulator circuits described above with respect to FIG. 23 is a passive circuit that passively ramp a stimulation signal without the use of internal logic or intelligence, it should be appreciated that in some variations a stimulation circuit as described here may comprise a microcontroller or other internal logic that may control the ramping of a stimulation signal.

Other variations of circuits that may be suitable for use in a nasal microstimulator are described in U.S. patent application Ser. No. 13/441,806, filed Apr. 6, 2012, and titled "Stimulation Devices and Methods," which is hereby incorporated by reference in its entirety.

In a microstimulator that comprises a passive stimulation circuit without an internal power source, the microstimulator may comprise one or more elements to receive power from an external source. For example, a controller may generate and transmit power wirelessly via an output signal (e.g., magnetic field). The microstimulator may comprise one or more energy-receiving units that receive the output signal from the controller to power the microstimulator. In some variations, the energy-receiving unit may be located in the extension of the microstimulator. The energy-receiving unit may be a coil, which may be formed from a wire having a length turned into a plurality of windings. In variations where the extension comprises more than one coil (e.g., two, three), each coil may be configured to receive the same signal or different signals. It may be advantageous for more than one coil to receive different signals, as this may allow more than one component (e.g., more than one electrode) of the microstimulator to be controlled separately.

Figure 2D:
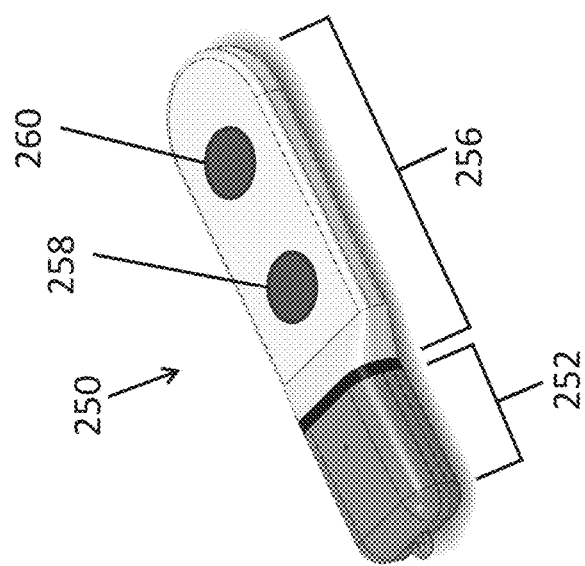
FIG. 2D shows a perspective view of another variation of a microstimulator described here.

The extension of the microstimulator may comprise one or more electrodes, which may deliver an electrical stimulus to tissue. In FIG. 2B, the extension (203) comprises one electrode (205). However, it should be appreciated that the extension may comprise any suitable number of electrodes (e.g., one, two, three, or four or more electrodes) positioned on any suitable portion or portions of the extension. In some variations, it may be advantageous for a microstimulator to comprise more than one electrode, as this may allow more than one area of tissue to be stimulated separately or simultaneously. That is, current may be directed via two or more different pathways between active and return electrodes at the same time, and/or current may be directed via two or more different pathways over time. This may be desirable, for example, to reduce accommodation to a stimulus. For example, FIG. 2D shows another variation of a microstimulator (250) comprising a first electrode (258) and a second electrode (260), each located on a first side of an extension (256). In some instances, the housing (252) may also comprise a conductive material (e.g., titanium), such that all or a portion of the housing may function as a return. In variations of the microstimulator that comprise more than one electrode, the electrodes may be positioned on one or more sides of the extension, and/or may be positioned near the housing. For example, FIGS. 3A-3C depict a microstimulator (300) comprising an extension (302) and a housing (301), where a first electrode (304) is located adjacent to a first side of the housing a second electrode (305) is located adjacent to a second side of the housing. One or more of the electrodes may be recessed, which may provide for more uniform charge density on the electrode surface, but need not be. The composition of the electrode may include, but is not limited to, platinum, iridium, platinum iridium, iridium oxide, sputtered iridium oxide, titanium nitride, tantalum, and combinations thereof.

As shown in FIGS. 3A and 3B, the microstimulator may comprise one or more feedthroughs (306) that extend between and electrically connect the housing (301) and the extension (302). One or more elements, such as an electrode (304, 305) or a coil (303), may be electrically connected to hermetically-sealed stimulation circuitry within the housing case by the feedthroughs. Additionally, one or more of the feedthroughs may comprise an insulating member which may electrically isolate the feedthrough from the housing. FIG. 2C also illustrates another variations of feedthroughs (222), which extend between the housing case (214) and the extension (216), which may electrically connect the circuitry within the housing to the coil (218) and/or electrode (220) on the extension (216).

The microstimulator may comprise other components or materials that may affect functionality. For example, to help keep the microstimulator in an implanted position, the microstimulator may comprise one or more fixation elements (e.g., one or more hooks, barbs, or anchors) or one or more materials (e.g., a Dacron covering) or structures that may promote tissue ingrowth. The microstimulator may have one or more coatings which may be adhesive and/or bioabsorbable. In some variations, the microstimulator may comprise one or more coatings that have electrically conductive and/or electrically insulative properties (e.g., silicone).

In some variations, the microstimulator described here may be configured to be compatible with magnetic resonance imaging scanners. In some of these variations, the microstimulator may be configured to minimize its movement that may result from magnetic forces created during magnetic resonance imaging or minimize heating that may occur in the components of the microstimulator. For example, in some variations, the microstimulator may be made from non-ferromagnetic or reduced-ferromagnetic materials. In other variations, the microstimulator may comprise ferromagnetic materials, but the relative amount of these components may be small enough such that forces provided on these components during magnetic resonance imaging do not substantially move the microstimulator. In other variations, the microstimulator may be configured such that magnetic resonance imaging does not cause inadvertent stimulation or other activation of the microstimulator. For example, when the microstimulator comprises a receiving circuit having a resonant frequency, the microstimulator may be configured such that the resonant frequency is outside of the frequency ranges produced during magnetic resonance imaging (e.g., the frequencies produced by the main field gradient field, and/or radio frequency fields of a magnetic resonance imaging scanner).

An electrical stimulus delivered by the microstimulators described here may include a waveform or waveforms, which may be tailored for specific treatment regimens and/or specific patients. Waveforms that may be delivered by one or more variations of the microstimulators described herein are described in more detail in U.S. patent application Ser. No. 14/809,109, filed Jul. 24, 2015, and titled "Stimulation Patterns for Treating Dry Eye," which is hereby incorporated by reference in its entirely. In variations in which the microstimulator is configured to deliver a stimulus via two or more different pathways, the same or different waveforms may be delivered for each pathway, and the waveform delivered via each pathway may be changed over time. The waveforms may be pulse-based or continuous. It should be appreciated that the waveforms described here may be delivered via a multipolar (e.g., bipolar, tripolar) configuration or a monopolar configuration. When the microstimulator is configured to deliver a continuous waveform, the waveform may be a sinusoidal, quasi-sinusoidal, square-wave, sawtooth/ramped, or triangular waveform, truncated-versions thereof (e.g., where the waveform plateaus when a certain amplitude is reached), or the like. Generally, the frequency and peak-to-peak amplitude of the waveforms may be constant, but in some variations the microstimulator may be configured to vary the frequency and/or amplitude of the waveform. This variation may occur according to a predetermined plan, or may be configured to occur randomly within given parameters. For example, in some variations the continuous waveform may be configured such that the peak-to-peak amplitude of the waveform varies over time (e.g., according to a sinusoidal function having a beat frequency). In some instances, varying the amplitude and/or frequency of a stimulation waveform over time, or pulsing the stimulus on and off (e.g., 1 second on/1 second off, 5 seconds on/5 seconds off), may help reduce patient habituation (in which the subject response to the stimulation decreases during stimulation). Additionally or alternatively, ramping the amplitude of the stimulation waveform at the beginning of stimulation may increase comfort.

When the microstimulator is configured to create a pulse-based electrical waveform, the pulses may be any suitable pulses (e.g., a square pulse, a haversine pulse, or the like). The pulses delivered by these waveforms may by biphasic, alternating monophasic, or monophasic, or the like. When a pulse is biphasic, the pulse may include a pair of single phase portions having opposite polarities (e.g., a first phase and a charge-balancing phase having an opposite polarity of the first phase). In some variations, it may be desirable to configure the biphasic pulse to be charge-balanced, so that the net charge delivered by the biphasic pulse is approximately zero. In some variations, a biphasic pulse may be symmetric, such that the first phase and the charge-balancing phase have the same pulse width and amplitude. In other variations, a biphasic pulse may be asymmetric, where the amplitude and/or pulse width of the first pulse may differ from that of the charge-balancing phase. In some variations, the aspect ratio between the amplitude and duration may change over time, either abruptly or gradually. Additionally, each phase of the biphasic pulse may be either voltage-controlled or current-controlled. In some variations, both the first phase and the charge-balancing phase of the biphasic pulse may be current-controlled. In other variations, both the first phase and the charge-balancing phase of the biphasic pulse may be voltage-controlled. In still other variations, the first phase of the biphasic pulse may be current-controlled, and the second phase of the biphasic pulse may be voltage-controlled, or vice-versa.

When an electrical pulse waveform is an alternating monophasic pulsed waveform, each pulse delivered by the microstimulator may have a single phase, and successive pulses may have alternating polarities. Generally, the alternating monophasic pulses are delivered in pairs at a given frequency (such as one or more of the frequencies listed above, such as between 30 Hz and 50 Hz), and may have an inter-pulse interval between the first and second pulse of the pair (e.g., about 1000 μs, between 500 μs and 1500 μs, between 50 μs and 150 μs or the like). Each pulse may be current-controlled or voltage-controlled, and consecutive pulses need not be both current-controlled or both voltage-controlled. In some variations where the pulse waveform is charged-balanced, the waveform may comprise a passive charge-balancing phase after delivery of a pair of monophasic pulses, which may allow the waveform to compensate for charge differences between the pulses.

When a microstimulator is configured to deliver a pulse-based waveform, the stimulation amplitude, pulse width, and frequency may be the same from pulse to pulse, or may vary over time. For example, in some variations, the amplitude of the pulses may vary over time. In some variations, the amplitude of pulses may vary according to a sinusoidal profile. In some variations, the stimulation waveform may be a modulated high frequency signal (e.g., sinusoidal), which may be modulated at a beat frequency of the ranges described above. In such variations, the carrier frequency may be between about 100 Hz and about 100 kHz. In other variations, the amplitude of pulses may increase (linearly, exponentially, etc.) from a minimum value to a maximum value, drop to the minimum value, and repeat as necessary. In some variations, the user may be able to control the stimulus during its delivery. For example, using a controller the user may increase the intensity of the stimulus. It may be desirable for the patient to increase the intensity of the stimulus until the stimulus causes paresthesia (e.g., tingling, tickling, prickling). As such, the patient may be able to self-determine the proper stimulation intensity and self-adjust the stimulus to a level effective to achieve the desired result (e.g., tear production). It may be desirable for the user to increase the intensity of the stimulus slowly in order to minimize discomfort.

In some instances, it may be desirable to configure the stimulation waveform to minimize side effects. In some instances, it may be desirable to promote stimulation of larger-diameter nerves (e.g., afferent fibers of the anterior ethmoidal nerve), which may promote a therapeutic effect, while reducing the stimulation of smaller nerves (e.g., a-delta fibers, c fibers, sympathetic and parasympathetic fibers), which may result in discomfort or mucus production. Generally, for smaller pulse-widths, the activation threshold for larger-diameter nerves may be lower than the activation threshold for the smaller nerve fibers. Conversely, for larger pulse-widths, the activation threshold for larger-diameter nerves may be higher than the activation threshold for the smaller nerve fibers. Accordingly, in some instances, it may be desirable to select a pulse width that preferably activates the larger-diameter nerves. In some variations, the pulse width may be between 30 μs and about 70 μs, or may be between about 30 μs and about 150 μs.

More specifically, the microstimulator may be configured to deliver a waveform at a frequency between about 0.1 Hz and about 200 Hz. In some of these variations, the frequency is preferably between about 10 Hz and about 60 Hz. In some of these variations, the frequency is preferably between about 25 Hz and about 35 Hz. In others of these variations, the frequency is preferably between about 50 Hz and about 90 Hz. In some of these variations, the frequency is preferably between about 65 Hz and about 75 Hz. In other variations, the frequency is preferably between about 130 Hz and about 170 Hz. between about 0.1 Hz and about 200 Hz. In some of these variations, the frequency is preferably between about 10 Hz and about 200 Hz. In some of these variations, the frequency is preferably between about 30 Hz and about 150 Hz. In others of these variations, the frequency is preferably between about 50 Hz and about 80 Hz. In others of these variations, the frequency is preferably between about 30 Hz and about 60 Hz. In some variations, the frequency may be about 1.5 Hz, about 10.25 Hz, about 70 Hz, about 150 Hz, about 25 Hz, about 27.5 Hz, about 30 Hz, about 32.5 Hz, about 35 Hz, about 37.5 Hz, about 40 Hz, about 42.5 Hz, about 45 Hz, about 47.5 Hz, about 50 Hz, about 52.5 Hz, about 55 Hz, about 57.5 Hz, about 60 Hz, about 62.5 Hz, or about 65 Hz. In some of these variations, the frequency is preferably between about 145 Hz and about 155 Hz. In some variations, high frequencies, such as those between about 145 Hz and about 155 Hz may be too high for each pulse to stimulate/activate the target nerve. As a result, the stimulation may be interpreted by the patient to have an element of randomness, which in turn may help to reduce subject habituation.

Similarly, for the treatment of dry eye, when the first phase of the biphasic pulse is current-controlled, the first phase may preferably have an amplitude between about 10 µA and 100 mA. In some of these variations, the amplitude may be preferably between about 0.1 mA and about 10 mA. In yet others of these variations, the amplitude may preferably be between about 1.0 mA and about 10 mA. Amplitudes within these ranges may be high enough to stimulate targeted tissue, but sufficiently low as to avoid any significant heating of tissue, ablation of tissue, or the like. In some variations the amplitude may be between about 1.0 mA and about 5.0 mA. In other variations, the first phase may have an amplitude of about 0.1 mA, about 0.2 mA, about 0.3 mA, about 0.4 mA, about 0.5 mA, about 0.6 mA, about 0.7 mA, about 0.8 mA, about 0.9 mA, or about 1.0 mA. In some variations, the amplitude may be variable. For example, the amplitude may vary between about 1.3 mA and about 1.5 mA, about 2.2 mA and about 2.5 mA, about 3.2 mA and about 3.7 mA, about 4.3 mA and about 5.0 mA. When the first phase of the biphasic pulse is voltage-controlled, the first phase may preferably have an amplitude between about 10 mV and about 100 V.

In some variations, the amplitude may vary over time. This may reduce patient accommodation. In some variations, the amplitude of pulses may increase (linearly, exponentially, etc.) from a minimum value to a maximum value, drop to the minimum value, and repeat as necessary. In some variations, the amplitude of the pulses may vary according to a sinusoidal profile. In some variations in which the amplitude varies over time, the amplitude may vary at a frequency suitable for reducing patient accommodation or increasing patient comfort such as between about 0.1 Hz and about 5 Hz, between about 1 Hz and about 5 Hz, between about 1 Hz and 2 Hz, between about 2 Hz and 3 Hz, between about 3 Hz and 4 Hz, or about 4 Hz and 5 Hz. In some variation, the amplitude may vary at a frequency of about 1.0 Hz, about 1.1 Hz, about 1.2 Hz, about 1.3 Hz, about 1.4 Hz, about 1.5 Hz, about 1.6 Hz, about 1.7 Hz, about 1.8 Hz, about 1.9 Hz, about 2.0 Hz, about 2.1 Hz, about 2.2 Hz, about 2.3 Hz, about 2.4 Hz, about 2.5 Hz, about 2.6 Hz, about 2.7 Hz, about 2.8 Hz, about 2.9 Hz, about 3.0 Hz, about 3.1 Hz, about 3.2 Hz, about 3.3 Hz about 3.4 Hz, about 3.5 Hz, about 3.6 Hz, about 3.7 Hz, about 3.8 Hz, about 3.9 Hz, or about 4.0 Hz.

Additionally, the first phase may preferably have a pulse width between about 1 µs and about 10 ms. In some of these variations, the pulse width may preferably be between about 10 µs and about 100 µs. In other variations, the pulse width may preferably be between about 100 µs and about 1 ms. In yet other variations, the pulse width may be between about 0 µs and about 300 µs. In yet other variations, the pulse width may be between about 0 µs and 500 µs.

In some variations, the pulse width may be constant over time. In other variations, the pulse width may vary over time. Pulse width modulation over time may increase the efficacy and/or comfort of the stimulation. In some variations, the pulse width may increase (linearly, exponentially, etc.) from a minimum value to a maximum value, drop to the minimum value, and repeat as necessary. In some variations, the pulse width may vary according to a sinusoidal profile.

In another variation, the pulse width may periodically increase from a baseline pulse width to a longer pulse width for a certain number (e.g., one, two) of pulses. In any form of pulse width modulation, the pulse width may vary at any suitable frequency. In some variations the pulse width may vary at about 0.1 Hz, about 0.2 Hz, about 0.3 Hz, about 0.4 Hz, about 0.5 Hz, about 0.6 Hz, about 0.7 Hz, about 0.8 Hz, about 0.9 Hz, about 1 Hz, about 1.1 Hz, about 1.2 Hz, about 1.3 Hz, about 1.4 Hz, or about 1.5 Hz. In some variations, modulation of the pulse width at a rate between about 0.5 Hz and 1 Hz may be desirable to increase patient comfort during stimulation. In some variations, the increase and decrease of pulse width may be defined by a function implemented by the microstimulator. For example, the pulse width may be defined by a function such that the pulse width varies exponentially. In one variation, the function defining pulse width may comprise two phases—a first phase during which the pulse width of the leading pulse increases over time according to an exponential function, and a second phase during which the pulse width of the leading pulse exponentially decays over time.

In some instances, the waveforms described herein may be delivered in a continuous fashion, while in other instances, the waveforms may be delivered in a non-continuous fashion having on periods and off periods, which may reduce patient accommodation. Exemplary on/off durations include without limitation, 1 second on/1 second off, 1 second on/2 seconds off, 2 seconds on/1 seconds off, 5 seconds on/5 seconds off, 0.2 seconds on/0.8 seconds off, less than 1 second on/less than 10 seconds off.

Implantation Tool

Generally, an implantation tool as described herein may be used to deliver a microstimulator through a nostril of a subject to a desired implantation site. The implantation tool may comprise a shaft, features that may allow the microstimulator to be releasably attached to the implantation tool, and a handle that may improve a user's control of the system. The shaft may facilitate maneuvering the microstimulator into and within a confined space, such as a portion of the nasal cavity or tissue. The shaft may have any suitable, elongate shape (e.g., cylinder, rectangular prism), such that at least a distal end of the shaft may be inserted through a nostril and into a nasal cavity of a patient. In some variations, the shaft may be shaped to reduce the risk of trauma to the nostril and nasal tissue during implantation. For example, the shaft may have a flat and thin shape, comprise rounded edges, and/or comprise a lubricious coating. In some variations, the shaft may be straight, whereas in other variations the shaft may comprise one or more curves, which may facilitate manipulation of the distal end of the implantation tool at an implantation site. In some variations, the shaft may be steerable with one or more controls. The implantation tool may have a length that is at least long enough for a proximal portion of the tool to be held and maneuvered by a user outside of a patient's nasal cavity while a distal portion of the tool is within the nasal cavity. For example, in some variations, the length of the implantation tool may be between about 15 cm and about 25 cm. In some of these variations the length may be about 17 cm. The length of the portion of the implantation tool that may be inserted into a nostril during the implantation procedure may be different for different patients, and may be less than about 7 cm (e.g., between about 2 cm and about 6 cm, about 4 cm).

In variations of the implantation tool described herein, the microstimulator may be releasably attached to a distal end of the shaft. It should be appreciated, however, that the microstimulator may be releasably attached at any suitable location on the implantation tool. The system may be configured such that the microstimulator is irreversibly detachable from the implantation tool (i.e., once the microstimulator is detached from the implantation tool, it may not be able to be reattached), or the system may be configured such that the microstimulator is reversibly detachable from the implantation tool (i.e., the microstimulator may be reattached to the implantation tool after being detached). When the microstimulator is reversibly detachable, this may facilitate, for example, repositioning or removal of the microstimulator after delivery. For example, an implantation tool may comprise a hook that releasably attaches to an eyelet on a microstimulator. To release the microstimulator, the hook may be unhooked from the eyelet. To reposition or remove the microstimulator, the hook may rehook the eyelet.

The implantation tool may hold the microstimulator in an orientation that facilitates implantation (e.g., implantation into a tissue pocket). For example, when the implantation tool is inserted in a nasal cavity, it may be advantageous for the microstimulator to be held in the correct orientation for implantation. This may minimize any repositioning that may be needed after the microstimulator is deposited, which may minimize tissue trauma and the time of the implantation procedure. In some variations, it may be advantageous for the implantation tool to have minimum contact with the microstimulator, which may in turn minimize the portion of the implantation tool that may enter tissue when the microstimulator is deposited and minimize the size of tissue pocket that may be formed.

A variation of the implantation tool (102) is illustrated in FIGS. 1A and 1B, releasably attached to a microstimulator. This implantation tool comprises a shaft (106), a handle (108), and a tension system to facilitate the releasable attachment of a microstimulator to the implantation tool. The tension system comprises a contact surface or cup (107) at a distal end of the shaft that is complimentary to the shape of the microstimulator, a tensioning element (111) that is connected to the microstimulator, and a knob (112) that secures the tensioning element to a proximal end of the implantation tool. The tensioning element may be any suitable flexible, string-like structure, such as a suture, a wire, or a chain. This embodiment comprises a retractable cover (109) that may be advanced and retracted relative to the shaft. The retractable cover may facilitate one or a number of functions during the implantation process. For example, in one position the retractable cover may cover and protect the microstimulator electrode. In some variations, the retractable cover may comprise a curved distal tip, which may facilitate tissue pocket formation or opening.

The implantation tool (102) shown in FIGS. 1A and 1B comprises a shaft (106) that may allow a user to maneuver the microstimulator into and within a confined space, such as a portion of the nasal cavity or tissue. As shown in FIG. 1A, the implantation tool may comprise a handle (108) at a proximal end of the implantation tool that may allow a user to manipulate and control the implantation tool. Generally, the handle may be sized and configured to be held by a user. In some variations, a handle may have a length between about 10 cm and about 20 cm (e.g., between about 12 cm and 15 cm). While shown in FIG. 1A as having a circular cross-sectional shape, the handle may have a cross-section having any suitable shape (e.g., rectangular, oval, irregular shape). In some variations, the handle may comprise one or more grooves and/or finger indentations that may allow a user to more easily grasp or hold the implantation tool. The handle may be integrally formed the shaft or formed separately and attached in any suitable manner.

The implantation tool may comprise features that facilitate the releasable attachment of the microstimulator to the implantation tool. The microstimulator may be attached to the implantation tool while the microstimulator is inserted through a nostril and positioned for implantation. When positioned at a desired implantation location, the microstimulator may be released from the implantation tool. A tension system is one variation that may facilitate this process, an example of which is shown in FIGS. 4A-4C. FIGS. 4A and 4B depict perspective views of a distal portion of an implantation tool, and FIG. 4C depicts a perspective view of a proximal portion of the implantation tool. The tension system may comprise a contact surface (402) at a distal end of the shaft (404), a tensioning element (406) that may be at least partially disposed in a lumen of the shaft, and a knob (408) at a proximal end of the shaft. The contact surface shape may be complimentary to the shape of a portion of the microstimulator (410), which may maintain the microstimulator in a desired orientation. The tensioning element may attach to the microstimulator (e.g., attach to a connector on the microstimulator, such as an eyelet (412), as was described in more detail with respect to FIG. 2A), and may extend within the shaft lumen between a distal opening (414) at the cup and a proximal opening (416) at the proximal end of the shaft. A knob may secure the tensioning element at the proximal opening. FIG. 4A depicts the microstimulator at a distance from the contact surface, but tension may be applied to the tensioning element, such that the microstimulator is pulled into contact with the holder, as is shown in FIG. 4B. The knob may hold the tensioning element in tension to maintain contact between the contact surface and microstimulator during portions of the implantation procedure.

The contact surface (402) may comprise any suitable shape that is complementary to a portion of the microstimulator (410). It may in some instances be desirable for the cross-sectional dimensions of the contact surface to be less than or equal to those of the microstimulator when the contact surface and microstimulator are coupled. This may reduce tissue trauma during implantation, and may limit the size of tissue pocket formation during implantation. For example, as illustrated in FIG. 4B, the contact surface (402) may have a concave shape complementary to an outer convex surface of the distal end of the microstimulator (410), allowing the contact surface to stabilize the microstimulator while having a height (411) and width (413) smaller than or equal to the dimensions of the microstimulator (410).

The contact surface may be shaped to hold the microstimulator in a desired orientation (e.g., the correct orientation for implantation). For example, in FIGS. 4A and 4B, the orientation of the contact surface holds the microstimulator such that the longitudinal axes of the microstimulator and the implantation tool shaft are parallel. In some variations, however, the contact surface may be shaped in such a way as to hold the microstimulator at an angle relative to the shaft. In FIGS. 4A and 4B, the longitudinal axis of the shaft is aligned with the longitudinal axis of the microstimulator. However, in other variations, the contact surface may hold the microstimulator in an orientation such that the longitudinal axis of the microstimulator is parallel to but displaced relative to the longitudinal axis of the shaft. In some variations, this may be advantageous because it may allow the microstimulator to be advanced along a tissue surface while the shaft is at a distance from the tissue surface.

The contact surface may be shaped to securely hold the microstimulator in a fixed orientation relative to the shaft to reduce the risk of the microstimulator being inadvertently moved or dislodged from its desired orientation during the implantation procedure. In some variations, the contact surface may contact portions of one or more sides of the microstimulator, which may reduce the risk of dislodgement. The materials of the contact surface may have stiffness and/or strength that may reduce the risk that a force applied to the microstimulator and/or contact surface may deform the contact surface and/or reposition the microstimulator. The contact surface may be integrally formed with the shaft or formed separately and attached to the shaft in any suitable manner (e.g., welded, screwed).

The tension system may comprise a tensioning element (406) to attach the microstimulator to the implantation tool. In the variation shown in FIG. 4A, the tensioning element forms a loop through an eyelet (412) on the microstimulator (410), but the tensioning element may connect to a portion of the microstimulator in any suitable way (e.g., tied, clamped). The tensioning element may extend from the connection on the microstimulator, through the distal opening (414) of the contact surface (402), and into the lumen of the implantation tool shaft (404). In some variations, a contact surface may not comprise an opening and/or the shaft may not comprise a lumen, and the tensioning element may instead be positioned outside of the shaft. While FIG. 4C shows the tensioning element exiting the shaft lumen through the proximal opening (416) at the proximal end of the shaft, it should be appreciated that the tensioning element may exit the shaft lumen at any suitable location.

The tensioning element (e.g., string, suture, wire, or the like) may comprise any suitable material or materials, one or more of which may be biocompatible. A tensioning element comprised of one or more biocompatible materials may be particularly advantageous in variations of the implantation procedure where at least a portion of the tensioning element may be implanted with the microstimulator. The tensioning element may comprise one more bioabsorbable materials (e.g. polydioxanone, polyglycolide) and/or one or more nonabsorbable materials (e.g., nylon, polypropylene). The tensioning element may optionally comprise one or more radiopaque materials in order for the tensioning element to be visible with x-ray and fluoroscopy. In some variations, the tensioning element may be elastic. In some variations, the implantation system may comprise more than one tensioning element.

The tensioning element may be releasably attached to the implantation tool in order to hold the microstimulator against the contact surface during portions of the implantation procedure. In the variation shown in FIG. 4C, the tensioning element (406) is attached to the implantation tool with a knob (408). The knob may have a spherical shape with a radius greater than the radius of the proximal opening (416) of the lumen of the implantation tool shaft (404), which may prevent the knob from entering the lumen. It should be appreciated that the knob may comprise any shape that has at least one cross-sectional dimension larger than the cross-sectional dimensions of the proximal opening. The knob may be secured to the tensioning element to hold the tensioning element taut, which may in turn secure the microstimulator to the implantation tool as described herein.

In some variations, for example, the knob may comprise a lumen (424) extending between a distal inlet and proximal outlet (422). The tensioning element may extend proximally from the proximal opening (416) of the implantation tool lumen, enter the distal inlet of the knob (408), and exit from the proximal outlet (422) of the knob. A portion of the tensioning element extending proximally from the proximal outlet (422) may be secured to maintain tension in the tensioning element. For example, a knot may be tied in the tensioning element that abuts against the proximal outlet. A cross-sectional dimension of the knot may be larger than the cross-sectional dimensions of the proximal outlet, which may reduce the risk of the knot entering the knob lumen and releasing the tension in the tensioning element. As another example, a clip having larger cross-sectional dimensions than the proximal outlet of the knob (422) may be attached to the tensioning element at the proximal outlet. Alternatively, the tension system may not comprise a knob, and a clip having larger cross-sectional dimensions than the proximal opening of the implantation tool lumen may be attached to the tensioning element at the proximal opening.

In other variations, friction may hold the tensioning element in place within the knob lumen (424). Friction between the tensioning element and knob lumen may be increased by materials of the tensioning element, materials of the knob lumen, and/or an element within the knob lumen (e.g., one-way valve). While not shown, in some variations the tensioning element may be secured between an internal surface of the knob and an external surface of the implantation tool shaft. For example, the implantation tool shaft may comprise a male component that may be inserted into the knob lumen, which may function as a female component. The tensioning element may exit through the proximal opening of the implantation tool shaft and then be positioned around the external surface of the male component. The male component and the tensioning element may be inserted into the lumen of the knob, such that the tensioning element is held between an external surface of the male component and an internal surface of the knob. In some variations, in order to attach the knob to the male component, the knob may comprise internal threads, and the male component may comprise mating external threads. In other variations, the knob may be secured to the male component with a press fit.

In variations of the implantation tool that comprise a tension system to releasably attach the microstimulator to the implantation tool, the microstimulator may be released by removing the tension. In the example described comprising a tensioning element and knob, removing the tension may comprise releasing the tensioning element from the knob. In some variations, releasing the tensioning element from the knob may comprise cutting or otherwise severing the tensioning element. In variations where the tensioning element is tied into a knot at the proximal outlet of the knob, the tensioning element may be severed at any position distal to the knot with a blade or scissors. In some variations, a knot may be untied to release the tensioning element. In variations of the knob that comprise a clip positioned on the tensioning element at the proximal outlet of the knob, the tensioning element may be released by removing the clip. In variations where the knob screws onto a portion of the shaft, the tensioning element may be released by unscrewing the knob. When the tension in the tensioning element is released, the microstimulator may no longer be held against the contact surface at the distal end of the implantation tool. Releasing the tensioning element while the microstimulator is in a tissue pocket may release the microstimulator into the tissue pocket. The implantation tool may then be withdrawn from the implantation site while the microstimulator is left in place.

In some variations, the implantation tool may comprise a retractable cover (e.g., retractable cover 109 in FIGS. 1A-1B). FIGS. 5A-5C are perspective views of a distal portion of an implantation tool (500) comprising a retractable cover (501) and an attached microstimulator (502). The retractable cover may comprise a proximal portion (504) that is at least partially disposed around the implantation tool shaft (506) and slidable relative to the shaft. The retractable cover may be slidable relative to the shaft between an advanced, distal position for implantation and a retracted, proximal position for release within a tissue pocket. FIGS. 5A and 5B show the retractable cover in an advanced, distal position, and FIG. 5C shows the retractable cover in a retracted, proximal position. Moving the retractable cover from the advanced, distal position to the retracted, proximal position may expose or uncover more of the microstimulator. While FIG. 5C shows the microstimulator still partially covered by the retractable cover, it should be appreciated that in some variations, when the retractable cover is in the retracted, proximal position, it may not cover any of the microstimulator.

The retractable cover may slidably move along the implantation tool into one or more positions in any suitable way. For example, the proximal portion of the retractable cover may be disposed around at least a portion of the shaft such that a user may advance or retract the proximal portion of the retractable cover to a desired position. In some variations, the shaft and/or retractable cover may comprise one or more locks that may indicate and/or hold the retractable cover in a desired position. For example, a lock may hold the retractable cover in an advanced position during implantation. The lock may be unlocked by a user (e.g., by applying sufficient force to the retractable cover) in order to change the position of the retractable cover.

FIG. 5A shows a first side of the retractable cover and FIG. 5B shows an opposite, second side of the retractable cover. The retractable cover may comprise a distal portion (508) that covers at least a portion of an attached microstimulator when the retractable cover is in an advanced, distal position, as will be discussed in more detail herein. The distal portion of the retractable cover may comprise a distal tip (510) that extends distal to a distal end (512) of an attached microstimulator when the retractable cover is in an advanced, distal position. In some variations, the distal tip (510) may be curved such that it wraps at least partially around the distal end of an attached microstimulator when the retractable cover is in an advanced position. In some variations, the retractable cover may comprise a channel or port for suction, irrigation, or fluid delivery (e.g., to administer a conductive fluid to an implantation site that may improve stimulation by a micro stimulator).

In the advanced, distal position, the retractable cover may facilitate one or a more steps of the implantation procedure. For example, in variations of the retractable cover that comprise a distal tip that extends distal to the microstimulator, the retractable cover may facilitate tissue pocket opening and/or formation. The distal tip may apply force to tissue to open a pocket and/or to extend a pocket as it is advanced though tissue. A distal tip may be used to open a pre-formed tissue pocket (e.g., pre-formed by a dissection tool) that may be the implantation site for the microstimulator. The thickness of the distal tip may be less than the thickness of the microstimulator, which may make it easier to insert the distal tip into an opening than it may be to insert the microstimulator without a distal tip into an opening. In some variations, one or more portions of the retractable cover (e.g., the distal tip) may comprise one or more sharp edges and/or one or more blunt edges. For example, the retractable cover may comprise a sharp edge to make an incision in tissue to start tissue pocket formation and/or one or more blunt edges to extend a tissue pocket. In some variations, as is shown in FIGS. 5A-5C, the width of the retractable cover distal tip may be tapered such that the width decreases from a proximal end of the tip to the distal end of the tip. When the tip is advanced through an opening in tissue, the increasing width of the tip may dilate the opening as the tip passes therethrough. Additionally or alternatively, a retractable cover may shield a microstimulator during insertion.

In some variations in which the retractable cover comprises a curved distal tip, the curved distal tip may be flexible, such that it may be biased to a curved configuration when unconstrained (e.g., when the distal tip is distal to the microstimulator as in FIGS. 5A and 5B), but may be straightened when a force is applied to an inner curvature of the distal tip (e.g., when the retractable cover is retracted relative to the microstimulator). FIG. 5C depicts the distal tip in a straightened configuration. When retracted, the contact between the cover and the inner curvature of the distal tip may exert a force that straightens the distal tip of the retractable cover.

In an advanced, distal position, a portion of the retractable cover may cover at least a portion of one or more electrodes. The microstimulator shown in FIGS. 5A-5C comprises one electrode (514) on a first side that is partially covered by the retractable cover when the retractable cover is in the advanced position. Coverage of an electrode by the retractable cover may protect the electrode during the implantation procedure.

The retractable cover may also facilitate testing of the microstimulator. Testing may prevent a malfunctioning implant from being implanted. As compared to testing the microstimulator with a separate device, testing with the implantation tool may decrease the operating room time required for the implantation procedure, simplify tasks and equipment that may be needed for the implantation procedure, and/or reduce the infectious risk of touching an electrode before insertion. In some variations, testing of a microstimulator's electrical stimulus is facilitated by one or more electrodes positioned on a distal portion of the implantation tool (e.g., on the retractable cover). When a microstimulator is attached to the implantation tool and the retractable cover is in an advanced position, the one or more electrodes of the implantation tool may longitudinally align with and face towards the one or more electrodes of the microstimulator. In this position, the microstimulator may be activated by a controller to generate an electrical stimulus, and the electrical stimulus may be detected by electrodes on the retractable cover. The implantation tool may comprise an indicator (e.g., a light, an audible sound) to indicate if a satisfactory stimulus has been delivered. If the microstimulator is stimulating as desired, the microstimulator may be implanted. If the microstimulator is not functioning as desired, one or more changes may be made (e.g., the microstimulator may be replaced).

In some variations, when the retractable cover is an advanced position, there may be an air gap between the one or more electrodes of the microstimulator and the one or more electrodes of the retractable cover. Before implantation, the retractable cover and microstimulator may be submerged in a conductive solution (e.g., saline), which may fill the air gap and allow the implantation tool to detect a signal produced by the microstimulator. The microstimulator may also be tested after insertion into a tissue pocket while still connected to the implantation tool. In this case, blood, other nasal fluid, and/or an injected conductive solution (e.g., saline) may fill the air gap between the microstimulator and the retractable cover to conduct a signal produced by the microstimulator to the implantation tool.

In some variations, a distal portion of the implantation tool (e.g., retractable cover) may comprise one or more electric connectors that protrude from the device towards the electrodes of an attached microstimulator. For example, a retractable cover may comprise one or more springs that may contact one or more electrodes of an attached microstimulator when the retractable cover is in an advanced position. The one or more springs may be gently biased towards the one or more electrodes of the microstimulator, such that contact is made but the electrodes are not scratched or otherwise damaged. This configuration may facilitate testing of the microstimulator's electrical stimulus without introducing a conductive fluid. For example, a microstimulator may be packaged pre-attached to an implantation tool with a retractable cover in an advanced position, and the packaging and devices may be sterile. A controller may activate the microstimulator while still packaged, and an indicator on the implantation tool may be visualized through the packaging, such that testing of the microstimulator may be performed without breaking the sterile field.

The implantation tool may comprise an indicator (e.g., a light, an audible sound) that indicates if the microstimulator is delivering an appropriate stimulus. In some variations, the indicator may comprise an LED, which may be connected to support electronics. The LED may be positioned at any suitable location on the implantation tool (e.g., the handle, the retractable cover). In some variations, an implantation tool may comprise a different indicator for each electrode on the microstimulator. In other variations, the implantation tool may comprise one or more electrodes, but may not comprise an indicator. In these variations, the implantation tool may comprise one or more leads that may be connected to another device (e.g., an oscilloscope) that may indicate if a desired electrical signal is produced by the microstimulator. In still other variations, the implantation tool may not comprise features to test the microstimulator, but the retractable cover may comprise one or more openings that may allow a device (e.g., an oscilloscope) to directly contact and test the electrodes of the microstimulator while it is attached to the implantation tool.

In some variations, the implantation tool may comprise a light (e.g., LED) that is separate from an indicator light. The light may be located at a distal end of the implantation tool and may be turned on while positioned in the nasal cavity. The light may have a sufficient power (e.g., a 3 W LED) to be seen from outside the nasal cavity through nasal tissue while it is within the nasal cavity. In some variations, an LED may be positioned on the implantation tool at a location that corresponds to the position of an attached microstimulator (e.g., at the same longitudinal position as a distal end of a micro stimulator). When the implantation tool and attached microstimulator are inserted into a nasal cavity, light from the LED may be seen from outside the nasal cavity to give a visual indication of the position of the microstimulator. In some variations, this may reduce the risk of advancing the implantation tool and microstimulator too deep into the nasal cavity. In some variations, the light may illuminate the nasal septum in order to visualize the transition point between cartilage and bone. This may facilitate implantation of the microstimulator adjacent to a desired part of the nasal septum (e.g., over the bony part).

Another variation of an implantation tool (600) is depicted in FIGS. 6A-6C. FIG. 6A shows the implantation tool (600) detached from a microstimulator (602), FIG. 6B shows the microstimulator releasably attached to the implantation tool, and FIG. 6C shows the implantation tool releasing the microstimulator. This variation of implantation tool comprises a shaft (604), a handle (606), and a friction system that may facilitate the releasable attachment of a microstimulator to the implantation tool with. The friction system may comprise a holder (608), a pusher (610), and a control slider (612). These features will be described in more detail herein.

The implantation tool embodiment shown in FIGS. 6A-6C comprises a shaft (604) that may allow a user to extend a microstimulator into a nasal cavity when the microstimulator is attached to the implantation tool. As shown, the shaft may have rounded edges, which may reduce the risk of trauma to tissue (e.g. nasal tissue) that the shaft may contact.

As shown in FIGS. 6A-6C, the implantation tool may comprise a handle (606) positioned at a proximal end of the implantation tool (600) that may allow a user to manipulate and control the implantation tool. Generally, the handle is sized and configured to be held by a user. While shown in FIGS. 6A-6C as having a rectangular cross-sectional shape, the handle may have a cross-section having any suitable shape (e.g., circle, oval, irregular shape). In some variations, the handle may comprise one or more grooves and/or finger indentations that may allow a user to more easily grasp or hold the implantation tool. The handle may be integrally formed with the shaft or may be formed separately and attached to the shaft in any suitable way.

The implantation tool shown in FIGS. 6A-6C comprises a friction system that facilitates the releasable attachment of a microstimulator (602) to the implantation tool. The friction system comprises a holder (608) that may hold the microstimulator at a distal end of the implantation tool utilizing friction between one or more portions of the holder and the microstimulator. Accordingly, the microstimulator may be released from the implantation tool when the static friction between the microstimulator and holder is overcome. In some variations, as is shown in FIGS. 6A-6C, the static friction may be overcome by a pusher (610) that is pushed against a proximal surface of the microstimulator. A user may advance a control slider (612) to advance the pusher and push the microstimulator from the holder.

Generally, a friction holder may comprise one or more elements at the distal end of the implantation tool that contact at least a portion of the microstimulator and resist its movement. The structure and/or materials of the holder and/or microstimulator may create frictional forces between the surfaces of the holder and microstimulator that are great enough to reduce the risk of the microstimulator being dislodged or inadvertently moved from its desired orientation (e.g., the correct orientation at implantation). Structures used in a friction holder may include, but are not limited to pockets or lumens, grooves, and/or clamps.

FIGS. 7A and 7B depict perspective views of distal portions of an implantation tool (700) comprising a holder (701) attached to a shaft (702). FIG. 7A depicts the holder detached from a microstimulator (706), and FIG. 7B depicts the microstimulator releasably attached to the implantation by the holder. The holder comprises a shaft attachment (708) and two grippers (710). The shaft attachment connects the grippers to the shaft and may be attached to the shaft in any suitable manner (e.g., adhesive, overmolding). When the microstimulator is releasably attached to the implantation tool, the grippers extend along the sides (711, 712) of the housing (713) of the microstimulator in order to grip the housing. The grippers may exert an inward force on the housing in order to hold the microstimulator in place. For example, the grippers may be inwardly biased, and may be deflected or displaced outwardly when a microstimulator is pushed into the holder. When deflected or displaced outwardly, the inward bias of the grippers may exert compressive forces on the microstimulator that may create a static friction between the microstimulator and the gripper surfaces. In some variations, the grippers may comprise compliant materials that may alternatively or additionally deform when a microstimulator is pushed into the holder. Deformation of the grippers may similarly exert compressive forces on the microstimulator.

The example shown in FIGS. 7A and 7B comprise two grippers configured to be located on opposing sides of a portion of a microstimulator, but a friction holder may comprise any number of grippers that may contact any number of sides of the microstimulator, including a single unitary gripper that extends around housing of a microstimulator. The inner surface of the grippers may comprise one or more suitable structures (e.g. grooves, protrusions) and/or materials (rubber, adhesive) that may increase the coefficient of friction between the surfaces of the microstimulator and the grippers.

In order to release the microstimulator from the implantation tool in variations that comprise a friction system, static friction between the microstimulator and implantation tool holder may be overcome. In the embodiment of implantation tool shown in FIGS. 6A-6C, a pusher (610) and control slider (612) may facilitate the release of the microstimulator (602) in this manner. Generally, the pusher (608) may contact and push against a proximal surface (614) of the microstimulator to overcome the static friction between the microstimulator and holder surfaces. A user may advance a control slider (612) to advance the pusher and push the microstimulator from the holder to release the microstimulator at an implantation site.

FIGS. 8A-8C show cross-sections of an implantation tool that comprises a pusher (802) and control slider (804). The pusher may be at least partially disposed in a lumen (806) of the implantation tool shaft (808). A distal end of the pusher may exit a distal opening (810) of the shaft to contact a portion of the microstimulator (812), which is shown in cross section in FIGS. 8A and 8C. As shown, the pusher is in a retracted, proximal position, and the microstimulator is held by the holder grippers (814). While the pusher is shown extending from the distal opening of the shaft in a retracted position, it should be appreciated that the distal end of the pusher may be aligned with the distal opening of the shaft or may be proximal to the distal opening of the shaft in the retracted position. In some variations, at least a portion of the microstimulator may be positioned within the shaft lumen when the pusher is in a retracted position.

The pusher (802) may be advanced or retracted relative to the shaft (808) by moving the control slider (804). The control slider may be connected to the pusher within the shaft lumen (806) and exit the shaft lumen through a side opening (816). A user may manipulate the portion of the control slider that is outside of the shaft lumen. In some variations, the side opening may limit the distance the control slider and pusher may be moved and/or may indicate when the pusher is in a retracted or advanced position. For example, as shown in FIG. 8B, the control slider is at a proximal end of the side opening (816), which prevents the control slider from moving further proximally relative to the shaft, and which may indicate that the pusher is in a fully retracted position. Advancing the control slider distally relative to the shaft to the distal end of the side opening (818) may advance the pusher and indicate that the pusher is in the fully advanced position. FIG. 6C shows a variation of the implantation tool where the control slider (612) is positioned at the distal end of the side opening (816) and the pusher (610) is in the fully advanced position. The implantation tool may comprise one or more features (e.g., a lock) that may reduce the risk of moving the control slider into an advanced position and releasing the microstimulator inadvertently.

Figure 9:
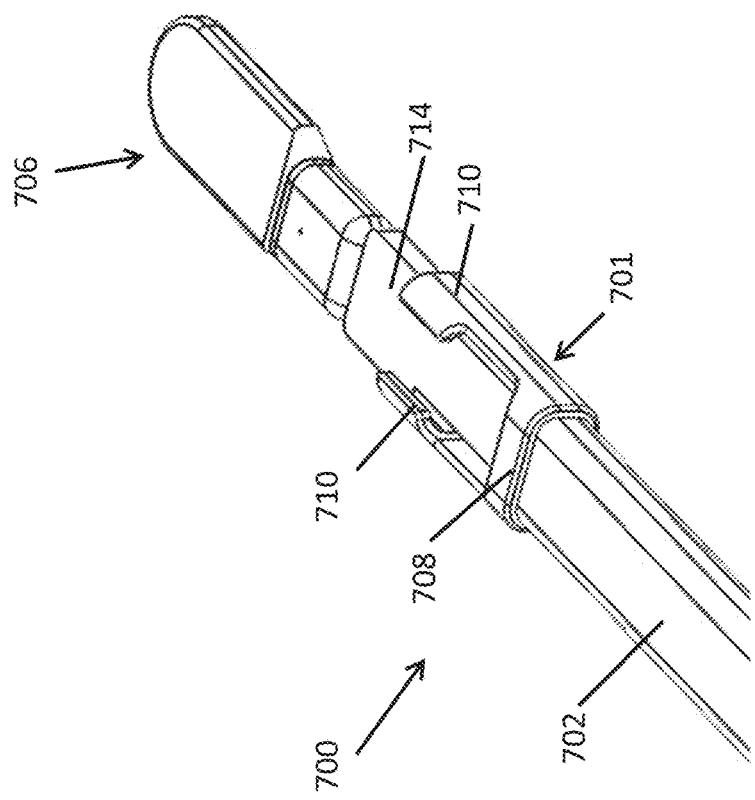
FIG. 9 shows a perspective view of a distal portion of the implantation tool and microstimulator of FIGS. 6A-6C.

FIG. 9 shows the distal portion of the implantation tool (700) of FIG. 7 comprising a holder (701) and a pusher (714). The pusher is shown in an advanced position, pushing the microstimulator (706) distally beyond the grippers (710) of the holder to release the microstimulator from the implantation tool. A pusher may comprise any suitable shape (e.g., cylindrical) and/or be moved in any suitable way (e.g., by pushing a portion of the pusher that may extend out of a proximal end of an implantation tool shaft). In some variations, a portion of the holder may be moved (e.g. the grippers retracted or opened) in order to release the friction holding the microstimulator to the implantation tool.

It should be appreciated that the features described herein with respect to the different implantation tools may be combined or rearranged as appropriate. For example, FIGS. 27A-E show another variation of an implantation tool (3000). Implantation tool (3000) comprises a shaft (3004), a retractable cover (3006), and a friction system to releasably attach a microstimulator (3002). The friction system comprises a gripper (3008) to hold the microstimulator while it is delivered to an implantation site, and a pusher (3010) to release the microstimulator at the implantation site. A portion of the pusher may be slidably disposed within a lumen of the shaft, and may be movable between a proximal, retracted position and a distal, advanced position. A portion of the pusher that extends proximal to the proximal end (3012) of the shaft may be pushed to advance the pusher relative to the shaft. In this variation of implantation tool, the retractable cover (3006) and/or gripper (3008) may be fixed to the shaft (3004), such that movement of the pusher (3010) relative to the shaft may also move the pusher relative to the retractable cover and gripper.

FIG. 27A shows the implantation tool (3000) with the pusher (3010) in a proximal, retracted position. FIG. 27C shows a magnified view of a distal portion of the implantation tool (3000) and microstimulator (3002) with the pusher in this position. In the retracted position, the inner surface of the gripper (3008) may contact a portion of the microstimulator surface to create a static friction between the surfaces. This friction may resist movement of the microstimulator away from the implantation tool and decrease the risk of the microstimulator being inadvertently dislodged from the implantation tool during implantation. The friction may be increased by one or more materials (e.g., rubber, adhesive) of the gripper and/or microstimulator surfaces that may increase the coefficient of friction between the surfaces. The gripper may be configured to exert a compressive force on the microstimulator, as was discussed in more detail with respect to FIGS. 7A and 7B, which may also increase friction between the gripper and the microstimulator.

When the pusher (3010) is in the retracted position, a portion of the retractable cover (3006) may cover a portion of the microstimulator (3002). In other words, when the pusher is in the retracted position, the retractable cover may be in an advanced position relative to the microstimulator. In this position, as was discussed in more detail with respect to FIGS. 5A and 5B, the retractable cover may cover and protect one or more electrodes (not shown) on the microstimulator. In variations where the retractable cover comprises one or more electrodes, this position may facilitate testing of the electrical stimulation delivered by the microstimulator. The retractable cover may comprise a distal tip (3014), which may extend beyond the distal end of the microstimulator and may facilitate opening and/or forming a tissue pocket. In some variations, as was discussed in more detail with respect to FIGS. 5A and 5B, the distal tip may comprise a curved portion that wraps around a portion of the distal end of the microstimulator. This configuration may further protect the microstimulator and/or facilitate tissue pocket opening and/or formation.

A proximal end (3013) of the pusher (3010) may be pushed relative to the shaft (3004) to distally slide the pusher relative to shaft, retractable cover (3006), and/or gripper (3008). FIG. 27B shows the implantation tool and microstimulator with the pusher in an advanced position (i.e., with the retractable cover in a retracted position relative to the microstimulator). FIGS. 27D and 27E show close-up views of the microstimulator and a distal portion of the implantation tool in the advanced position. When the microstimulator is held by the gripper, it may be adjacent to a distal end (3016) of the pusher, and distal advancement of the pusher may push the microstimulator distally. When the pusher is advanced, friction may be overcome between the gripper and the microstimulator, and the microstimulator may be advanced distal to the gripper to be released.

As seen in FIGS. 27A and 27B, the pusher may comprise a proximal cap (3018). The cap may comprise a dimension that is larger than the diameter of the shaft (3004) lumen, which may prevent the proximal end (3013) of the pusher (3010) from entering the lumen of the shaft. Abutment of the cap against the proximal end (3012) of the shaft may indicate that the pusher is in an advanced position. A cap may have one or more cross-sectional dimensions that are larger than corresponding cross-sectional dimensions of other portions of the pusher, which may make pushing and/or pulling of the shaft easier and/or more comfortable for a user.

The implantation tool may comprise a handle (3020), which may be at least partially disposed around a portion of the shaft. The handle may facilitate manipulation of the device by a user, for example by increasing the diameter of implantation tool. In some variations the handle may comprise one or more different materials than the shaft (e.g., silicone), which may provide a more comfortable gripping surface for a user. The handle may comprise one or more finger grooves, ridges, and/or other features to further improve gripping of the implantation tool by a user.

In some variations, a microstimulator (3002) that may be used with the implantation tool described in FIGS. 27A-27E may comprise a connector, such as an eyelet (3022). This may facilitate accessing the microstimulator after implantation for removal or repositioning. A tensioning element may connect to the connector, which may facilitate attachment of the microstimulator to one or more devices via tension, as was discussed in more detail with respect to FIGS. 5A-5C. In other variations, a tensioning element may be attached to the connector and implanted with the microstimulator such that a portion of the tensioning element remains outside of a tissue pocket. In some variations, the microstimulator may not comprise a connector and/or an attached tensioning element.

While tension and friction systems are described in detail herein, it should be appreciated that any suitable system may be used to releasably attach the microstimulator to the implantation tool. For example, the implantation tool may comprise a holding compartment that may have a closed configuration to hold the micro stimulator, and may be movable to an open configuration to release the microstimulator. In some variations, the implantation tool and microstimulator may be attached with one or more frangible connections that may be broken in order to release the microstimulator for implantation. It should also be appreciated that the implantation tool may comprise any suitable combination of elements described here to releasably attach a microstimulator. For example, while the variation shown in FIG. 4 was described as a tension system, it may also utilize friction to hold the microstimulator to the implantation tool. Inner surfaces of the extensions (420) in FIG. 4A may comprise a material or materials (e.g. adhesive material) or elements (e.g., grooves, protrusions) that may resist movement of the microstimulator relative to the contact surface.

Some variations of the implantation tool may comprise one or more elements that may facilitate the attachment of another device to the implantation tool. For example, an implantation tool may comprise one or more clips to attach an endoscope for viewing within the nasal cavity during the implantation procedure. In some variations, an implantation tool may attach to a suction catheter.

Figure 10:
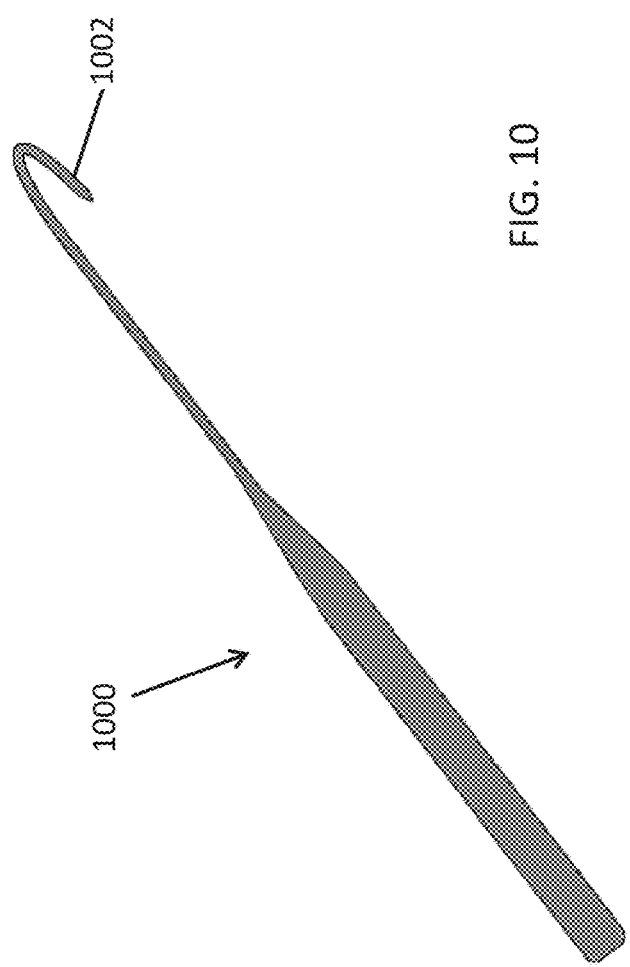
FIG. 10 shows an illustrative side view of a variation of a retrieval tool described here.

The implantation tool and microstimulator may be configured to reattach after being detached for implantation. This may allow an implantation tool to be used for repositioning or removing the microstimulator. In some variations, a separate retrieval device may be used for repositioning or removing the microstimulator. FIG. 10 shows an example of a retrieval tool (1000) that comprises a distal hook (1002) that may attach to a microstimulator connector, such as an eyelet.

The various components of the implantation tool (e.g., shaft, retractable cover, holder, handle) may be formed from any of the same, or different, suitable material or materials. These may include one or more metals (e.g., stainless steel, titanium, titanium alloys, or the like), one or more biocompatible plastics (e.g., polycarbonate, ABS, or the like), or combinations thereof and the like. One or more materials may be flexible or rigid. As discussed in more detail herein, a distal tip of a retractable cover may be flexible, but other components of the implantation tool may be flexible as well. For example, a flexible portion of the shaft may facilitate positioning of the microstimulator within a confined space (e.g., within the nasal cavity). One or more materials of the implantation tool may be electrically conductive or insulative. For example, at least a portion of the retractable cover may be electrically conductive in order to sense if the microstimulator is delivering an appropriate electrical stimulus, as described in detail herein. The implantation tool described here may be sterilizable (and in some instances, resterilizable), and may or may not be disposable.

Electrical Probe

The microstimulator may be implanted in a location that may allow an electrical stimulus from one or more microstimulator electrodes to stimulate a particular nerve, such as the anterior ethmoidal nerve. This stimulation may result in tear production. There may be variability between patients in the preferred stimulation location, for example due to variability in the anatomic location of the anterior ethmoidal nerve, and/or the position on the nerve that may produce a desired effect (e.g., maximum tear production). The desired implantation site (e.g., the site that locates the microstimulator electrode at a position to produce maximum tear production) may therefore be different for different patients. Additionally, electrical stimulation of some areas of the nasal cavity may elicit undesirable effects. For example, electrical stimulation of some nerves in the nasal cavity may produce paresthesia or discomfort. Areas that produce undesirable effects may also be different for different patients and may be avoided as implantation sites.

The nasal microstimulator implantation system may comprise a tool to help select an implantation site within nasal tissue. For example, an electrical probe may identify the desired implantation site for each patient by stimulating one or more locations in a nasal cavity while a patient response (e.g., tearing, sneezing, discomfort) is monitored. The electrical probe may comprise one or more electrodes to deliver an electrical stimulus. In some variations, the electrical probe may be configured to be used alongside a separate endoscope or other visualization tool so that the location that is stimulated by the electrical probe can be visualized. In other variations, rather than the visualization tool being separate, the electrical probe may comprise an integrated endoscope or other visualization tool. This may allow the endoscope and the electrodes to be maneuvered together. Visualizing the areas that are stimulated by the electrical probe may allow a user to determine the locations that produce undesired effects (e.g., discomfort, paresthesia) and/or desired effects (e.g., tearing, sneezing) when stimulated. The microstimulator may then be implanted in the location that elicited desired effects when stimulated, such that an electrode of the microstimulator is positioned at this specific location.

A variation of an electrical probe is shown in FIG. 11, which comprises an endoscope (1106) and an electrode (1102) attached to a distal end of a conductive shaft (1104). At least a portion of the conductive shaft may be covered by an insulation sheath (1108), which may electrically isolate the electrode and conducting elements from the other components of the electrical probe. In this variation, the endoscope comprises an endoscope shaft (1110) and an optic lens (1112) at a distal end of the endoscope. The endoscope is coupled to the insulation sheath with a clip (1114), such that the electrode (1102) is positioned distally to the optic lens of the endoscope. This configuration may facilitate visualization of the electrode and a surface (e.g., nasal tissue) that the electrode may contact. However, the endoscope and one or more electrodes may be connected in any suitable manner. In some variations, one electrode may be positioned on the electrical probe and a return electrode may be placed at a suitable location on the surface of a patient's skin (e.g., on the arm).

The electrical probe may have dimensions suitable for intranasal use. In some variations, one or more electrodes may have a spherical shape, similar to the electrode (1102) of FIG. 11. The size of an electrode may be such that it may stimulate a nasal septum without inadvertently making contact with another surface (e.g., an outside wall of the nose). In some variations, the diameter of a spherical-shaped electrode may be between about 1.5 mm and about 8 mm. In some of these variations, the diameter may be between about 3 mm and about 4 mm. The conductive shaft may have a length between about 5 cm and about 10 cm. In some of these variations, the length may be about 8 cm. The clip, or any suitable component for coupling a conductive shaft and electrode to an endoscope, may accommodate a range of endoscope sizes (e.g., between about 2.7 mm and about 10 mm in diameter, between about 2.7 mm and about 5 mm in diameter). In some variations, one clip may be flexible or otherwise configured for use with more than one endoscope size. In other variations, different clips may have different sizes for use with endoscopes of different sizes.

While one electrode (1102) is shown in FIG. 11, in some variations it may be advantageous for the electrical probe to comprise more than one electrode. This may allow more than one area of nasal tissue to be stimulated without repositioning the probe, which may reduce the time of the procedure. When the electrical probe comprises more than one electrode, the electrodes may be stimulated simultaneously or separately. The characteristics of the electrical stimulus (e.g., waveform, amplitude, frequency) may be the same or different than the characteristics of the electrical stimulus delivered by the microstimulator. In some variations, the electrical probe may not comprise a visualization element (e.g., an endoscope). In other variations, the electrical probe may comprise any suitable visualization element (e.g., endoscope, fiberscope, videoscope) to visualize the specific location in the nasal cavity that is stimulated by one or more electrodes. The distal end of the visualization element may comprise one or more features to change the field of view (e.g., flexible and controllable tip, zoom feature). This may be advantageous in variations of the electrical probe that comprise more than one electrode to allow a user to visualize the location of each electrode. Optical fibers may be contained within the endoscope shaft and may be connected proximally to one or more components (e.g., light source, eyepiece, monitor). In some variations, a light source may be positioned on the electrical probe. For example, a light source may be positioned in proximity to one or more electrodes, which may enhance visualization of the stimulated area. A light source close to an electrode may also be seen from outside the nasal cavity through tissue to give a visual indication of the position of one or more electrodes relative to external landmarks.

The electrical probe may comprise one or more channels and/or ports, which may facilitate one or more functions, such as irrigation. Irrigating an area of the nasal cavity (e.g., with saline), may improve visualization and/or improve electrical conductivity between one or more electrodes and nasal tissue.

In some variations, the electrical probe may comprise a marking element to allow a user to locate the desired implantation site after the endoscope has been withdrawn from the nasal cavity. For example, the electrical probe may comprise a surgical marking pen that may be slidably attached to the endoscope with a clip. When an implantation site is identified, the marking pen may be advanced and/or angled in order to mark the area of tissue at that site. In some variations, a marking pen may be positioned on a back side of an electrode, opposite to a contact side. After stimulation, with the electrical probe stationary, the electrode may be rotated to position the marking pen at the same location that was stimulated. In some variations, the implantation site may be marked with dye (e.g., India ink).

Dissection Tools

The nasal microstimulator implantation system may comprise one or more devices to facilitate dissection of nasal tissue in order to form a tissue pocket, within which a microstimulator may be implanted. Generally, a device may be used to incise a portion of nasal tissue to make an opening of a tissue pocket. A pocket may then be extended by inserting a portion of the incising device or a different device into the tissue opening and advancing the device between tissue layers. In some variations, the mucosal and submucosal layers may be incised and the pocket may be formed between the submucosa and the nasal septum (e.g., the cartilaginous and/or bony part of the nasal septum). It may be advantageous for the incision to be made with a sharp blade and the pocket extended with a blunt blade to decrease the risk of puncturing or otherwise damaging the nasal septum or other structures inadvertently. In some variations, one device may comprise both sharp and blunt blades, for example, a sharp blade on one end and a blunt blade on the other end. In other variations, one device may comprise a sharp blade and another device may comprise a blunt blade. A dissection tool may comprise other features to facilitate the formation of a pocket, such as a suction catheter and/or a handle, as is described in more detail herein.

FIGS. 12A and 12B show two variations of dissection tools (1200 and 1201, respectively) that may be used to open and/or extend a tissue pocket. The dissection tool (1200) in FIG. 12A comprises a sharp blade (1202) and a blunt blade (1204) on first and second ends of a shaft (1206), respectively. This dissection tool (1200) may be used to open and extend a tissue pocket. The dissection tool (1201) in FIG. 12B comprises a single blade (1208) on a distal end of a shaft (1210). As shown, the blade (1208) is a sharp blade that may be used to open a tissue pocket. However, in other variations of dissection tools having a single blade on a distal end of a shaft, the blade may have a blunt edge, which may be used to extend a tissue pocket.

The blades in FIGS. 12A and 12B have a scoop shape and may comprise a rounded edge. The thickness of the blade around its edges may be less than about 2 mm. In some variations the thickness may be less than about 1 mm, or in other variations may be less than about 0.5 mm. In some variations, the thickness may be about 0.5 mm. The variations in FIGS. 12A and 12B each comprise a handle (1214 and 1216, respectively) that may facilitate gripping and/or manipulation of the dissection tool by a user. A handle may be disposed around or otherwise attached to a portion of the shaft in any suitable way.

The scoop shape of the blade may facilitate elevating an opening of a tissue pocket and/or extending a tissue pocket safely. An open portion (1212), or lumen, of the scoop shape may face away from a nasal septum as the blade is advanced along a nasal septum to extend a tissue pocket. This orientation may reduce the risk of inadvertently damaging the nasal septum, since the edges of the blade may be parallel to or face away from the nasal septum. However, while the blades shown comprise scoop shapes, the blades may be flat or comprise any other suitable shape.

FIGS. 13A and 13B show two views of another variation of dissection tool (1300) that can provide suction to an area of the procedure. This variation comprises a blade (1302) at a distal end of a shaft (1304), a handle (1306), and a suction opening (1310) on the surface of the blade (1302). The blade may be sharp or blunt and comprise a scoop or any other suitable shape (e.g. rectangular, triangular) as described above with respect to FIGS. 12A and 12B. A tube (1308) may extend between a distal suction opening (1310) in the blade and a proximal opening at a suction port (1312). While the tube is shown positioned outside of the shaft in FIGS. 13A and 13B, in other variations the tube may be at least partially disposed within the shaft. In variations where the tube is positioned outside of the shaft, it may be secured to the shaft, blade, and/or handle in any suitable way (e.g., clips, adhesive, welding). The suction opening may be located anywhere on the blade, or the catheter may be positioned such that the distal catheter opening is adjacent to the blade.

The suction port (1312) may be attached to a suction source. Suction may decrease the amount of fluid (e.g., blood) in the nasal cavity during tissue pocket opening and/or extension, which may improve visualization of the implantation site and/or reduce the risk of a patient aspirating fluid during the procedure. The tube may be used for irrigation, such as with saline. In some variations, the same tube may be used for both suction and irrigation by connecting the port (1312) to a suction source or fluid source, respectively. In other variations, the tube may be detachable and different tubes may be used for different functions (e.g., suction, irrigation).

A dissection tool (1300) as shown in FIGS. 13A and 13B may have dimensions suitable for intranasal use. For example, the blade may have a width between about 4 mm and about 7 mm. In some variations, the blade width may be about 5 mm, which may facilitate forming a tissue pocket opening about 5 mm through which a microstimulator may be advanced. In some variations, the blade may be sharp, and may have an edge diameter less than about 0.2 mm. The inner diameter of a suction opening (1310) may be sized to accommodate a tube (1308) with an inner diameter of at least about 1.5 mm. In some variations, the inner diameter of a tube may be between about 2 mm and about 3 mm. In variations where the shaft (1304) comprises a lumen, the lumen may have a diameter between about 3 mm and about 5 mm.

While the dissection tool shown in FIGS. 13A and 13B comprises one blade, it may comprise two blades positioned at opposite ends of the shaft. One or both blades may comprise a catheter opening and the catheter may be fixed or movable for use with either blade. In some variations, the dissection tool may comprise more than one catheter for use with more than one blade or for more than one function (e.g., suction, irrigation). In some variations, a distal end of a dissection tool may comprise a light (e.g., an LED), which may facilitate visualization within a nasal cavity and/or indicate the position of the distal end of the dissection tool in the nasal cavity by viewing the light from outside the nasal cavity through nasal tissue.

In some variations, a dissection tool may be configured for use with an endoscope or may comprise a camera in order to allow a user to visualize an area around a blade of the dissection tool. This may be advantageous when the blade of the dissection tool is used in locations that are difficult to otherwise visualize, such as in natural anatomic cavities (e.g., a nasal cavity) or in artificially formed cavities (e.g., a surgically created tissue pocket). A dissection tool configured to allow visualization of an area around a blade may be particularly useful for separating nasal submucosa from septal cartilage or bone, or for separating layers of submucosa in order to form a pocket for an implantable microstimulator. Visualizing the layers of tissue that are separated as the pocket is extended may decrease the chances that the blade of the dissection tool inadvertently punctures or otherwise damages cartilage or bone of the septum. However, it should be appreciated that such dissection tools may be useful in any procedure involving incision and/or separation of tissues.

In some variations, a dissection tool may be configured to at least partially surround a shaft of an endoscope, thereby forming a sleeve for the endoscope shaft. In this way, the endoscope shaft and the dissection tool may be maneuvered together. A distal end of the endoscope shaft, which may comprise a lens, may be positioned near a blade of the dissection tool to allow visualization or an area around the blade. In some variations, the dissection tool may be configured to maintain an unobstructed field of view for the endoscope. For example, the blade may comprise an open face positioned such that the view from the endoscope is substantially through the opening. In some variations, the face of the blade may be covered to prevent tissue, blood, or other debris from entering the dissection tool and obscuring the view from the endoscope. Additionally or alternatively, the dissection tool may comprise one or more tubes or catheters, as discussed with respect to FIGS. 13A and 13B, to provide irrigation and/or suctioning to an area around the blade. In some variations, the dissection tool may releasably attach to the endoscope shaft in order to prevent inadvertent separation of the dissection tool and endoscope shaft during use.

FIGS. 30A-30C depict a variation of a dissection tool (3500) configured for use with an endoscope (3502). FIG. 30A shows the dissection tool (3500) in isolation, FIG. 30B shows the dissection tool partially surrounding an endoscope shaft (3504), and FIG. 30C is a magnified view of distal portions of the dissection tool (3500) and the endoscope shaft (3504). The dissection tool (3500) may comprise a shaft (3506), a blade (3508) at the distal end of the shaft (3506), and a lumen. The lumen may extend distally from an opening at the proximal end (3510) of the dissection tool (3500). In some variations, the lumen may extend along a portion of the length of the dissection tool (3500) and terminate proximal to the blade (3508). In other variations, the lumen may extend into or through the blade (3508). The lumen may be sized and shaped to allow the endoscope shaft (3504) to be inserted into the lumen from the proximal end (3510) of the dissection tool (3500). The lumen may also be sized and shaped to allow the endoscope shaft (3504) to be advanced or slid distally inside of the lumen to position a distal tip (3512) of the endoscope shaft (3504) in proximity to the dissection tool blade (3508).

The dissection tool (3500) may comprise a proximal section (3514) and a distal section (3516), which may include the blade (3508). In some variations, the proximal section (3514) may be configured to remain substantially outside of a cavity (e.g., an anatomic cavity, a surgically created cavity) during use, whereas at least a portion of the distal section (3516) may be configured to be inserted into the cavity. The proximal section (3514) may comprise one or more features to facilitate holding and maneuvering of the dissection tool (3500). For example, the proximal section (3514) may comprise ridges (3518) or other protrusions, which may improve a user's grip on the dissection tool (3500). As will be described in detail herein, the proximal section (3514) may be configured to releasably attach the dissection tool (3500) to the endoscope shaft (3504).

In some variations, the distal section (3516) of the dissection tool (3500) may be narrower (i.e., have a smaller maximum cross-sectional area) than the proximal section (3514) in order to facilitate insertion into a cavity. The distal section (3516) of the shaft (3506) comprises a tube, but may have other shapes. For example, FIG. 31 shows a variation of a dissection tool (3600) comprising a shaft (3602) with an incomplete circular cross-sectional shape, which may require less material for manufacture. Compared to a complete circle, the incomplete circle may have a smaller cross-sectional area, which may allow the dissection tool (3600) to be inserted into smaller cavities. As shown, a gap (3604) in the shaft (3602) may also allow a user to see a position of a distal tip (3608) of an endoscope shaft (3606) relative to a blade (3610) of the dissection tool (3600). This may allow a user to position the endoscope shaft (3606) within a lumen of the dissection tool (3600) at a location that will produce the desired field of view.

Returning to FIG. 30C, the distal section (3516) of the dissection tool (3500) may comprise the blade (3508). The blade (3508) may comprise an edge (3520) and a face (3522) enclosed by the edge (3520). The blade (3508) may comprise any of the blade features (e.g., size, shape) discussed with respect to any of the blades (1202, 1204, 1208, or 1302) of FIGS. 12A-13B. For example, the edge (3520) may be sharp or dull and/or the blade (3508) may have a scoop shape. In some variations, the face (3522) may comprise an opening, whereas in other variations, at least a portion of the face (3522) may be covered or closed. In variations where the face (3522) comprises an opening, the opening may be fluidly connected to the lumen of the dissection tool (3500).

In some variations, the blade (3508) may be configured so that a view from the endoscope shaft (3504) is substantially through the face (3522). For example, the face (3522) may have a size and a position that allows an optical axis of the endoscope to intersect the face (3522) when the endoscope shaft (3504) is positioned in the lumen of the dissection tool (3500). In some variations, the dissection tool (3500) may be configured for use with an endoscope that has an optical axis aligned with a longitudinal axis of the endoscope shaft (3504) (i.e., a zero degree endoscope). In these variations, at least a portion of the face (3522) may be centrally located relative to a longitudinal axis of the dissection tool shaft (3506). Additionally or alternatively, the dissection tool (3500) may be configured for use with an endoscope that has an optical axis obliquely oriented relative to the longitudinal axis of the endoscope shaft (3504) (e.g., a 30 degree endoscope, a 45 degree endoscope). In these variations, at least a portion of the face (3522) may be obliquely oriented relative to the longitudinal axis of the dissection tool shaft (3506).

In some variations, as shown in FIG. 31, a blade (3608) may be integral with a shaft (3610) of a dissection tool (3600). In other variations, as shown in FIGS. 32A and 32B, a blade (3702) and a shaft (3704) of a dissection tool (3700) may be separate elements that are attached. FIG. 32A shows the blade (3702) detached from the shaft (3704), as they may appear before assembly, and FIG. 32B shows the blade (3702) attached to the shaft (3704).

FIG. 33 shows a distal portion of a variation of a dissection tool (3800) comprising a blade (3802) that is configured to maintain a clear field of view for an endoscope (3804). As shown, at least a portion of the blade (3802) may be transparent. For example, at least a portion of the blade (3802) may be formed from a transparent plastic, glass, crystal (e.g. sapphire), or any other suitable transparent material. This may allow visualization through a solid portion the blade (3802) using the endoscope (3804). The blade (3802) may also be configured to prevent tissue, blood, and/or other debris from entering the dissection tool (3800) and obstructing the field of view of the endoscope (3804). For example, a face (3806) of the blade (3802) may be a solid surface that is integral with an edge (3808) of the blade (3802). Thus, the blade (3802) may not comprise any external openings or otherwise provide a connection between an environment outside of the dissection tool (3800) and a lumen inside of the dissection tool (3800) where the endoscope (3804) may be positioned. In some variations, the blade (3802) may be a single piece of solid, transparent material that is formed in a scoop shape.

FIG. 34 shows a distal portion of a variation of a dissection tool (3900) that comprises a blade (3902) with a window (3904). The window (3904) may be sealed against at least a portion of an edge (3906) of the blade (3902) in order to prevent material from entering the blade (3902) through an open face (3908). The window (3904) may be formed from a transparent material (e.g., plastic, glass, crystal, or the like) in order to allow visualization with an endoscope through the window (3904). In other variations, a dissection tool may comprise a cap or a sleeve, which may cover more of a blade than just the face. For example, the sleeve may be tubular with an open end and a closed end, and in some variations it may be elastic to fit tightly around a portion of the dissection tool. In some variations, at least a portion of the sleeve may have a similar shape and size as at least a portion of the blade so that the sleeve may fit tightly around the blade. The closed end of the sleeve may be positioned around at least the face of the blade in order to prevent material from entering the blade. In some variations, at least a portion of the sleeve may be transparent in order to allow visualization from the endoscope through the sleeve.

In some variations, instead of a sleeve or a window covering the outside of an open face of a blade, a dissection tool may comprise a barrier positioned at least partially within a lumen of the dissection tool (e.g., within a distal portion of the lumen, within a portion of the lumen inside of the blade, within a portion of the lumen inside of a shaft of the dissection tool, combinations thereof). The barrier may be configured to prevent tissue, blood, and/or other debris from obstructing a view of an endoscope by eliminating any connections that may allow debris to move between the open face of the blade and a portion of the dissection tool lumen where an endoscope shaft may be positioned. The barrier may be formed from a solid, gel, foam, or the like. In some variations, the barrier may be a liquid polymer that solidifies after it is delivered into the dissection tool. It may be advantageous for the barrier to conform to a shape of the dissection tool lumen because this may allow the barrier to form a fluid-tight seal between the face of the blade and the portion of the lumen where the endoscope shaft may be positioned. In some variations, the barrier may be transparent in order to allow visualization from the endoscope through the barrier. For example, the barrier may comprise an optically clear epoxy, resin, or the like (e.g., a Master Bond® epoxy such as EP30P epoxy, a Hapco, Inc. resin such as Ultraclear™ 480 Series resin, or the like).

In some variations, the barrier may be positioned at least partially within the dissection tool after an endoscope shaft has been positioned in the lumen of the dissection tool. This may result in a proximal portion of the barrier abutting against a distal tip of the endoscope shaft, which may allow the barrier to occupy an entire space between the endoscope shaft and the face of the blade. For example, a liquid polymer may be poured into the blade face, and the polymer may flow through the lumen of the dissection tool until it is stopped at the distal tip of the endoscope shaft. The liquid polymer may at least partially fill the lumen distal to the endoscope shaft, and in some variations the liquid polymer may fill the lumen until it forms a surface at the face of the blade. The polymer may then solidify, thereby forming a barrier between the face and the portion of the lumen where the distal tip of the endoscope is positioned. In other variations, the barrier may be positioned at least partially within the dissection tool before the endoscope shaft is inserted into the dissection tool.

Figure 35C:
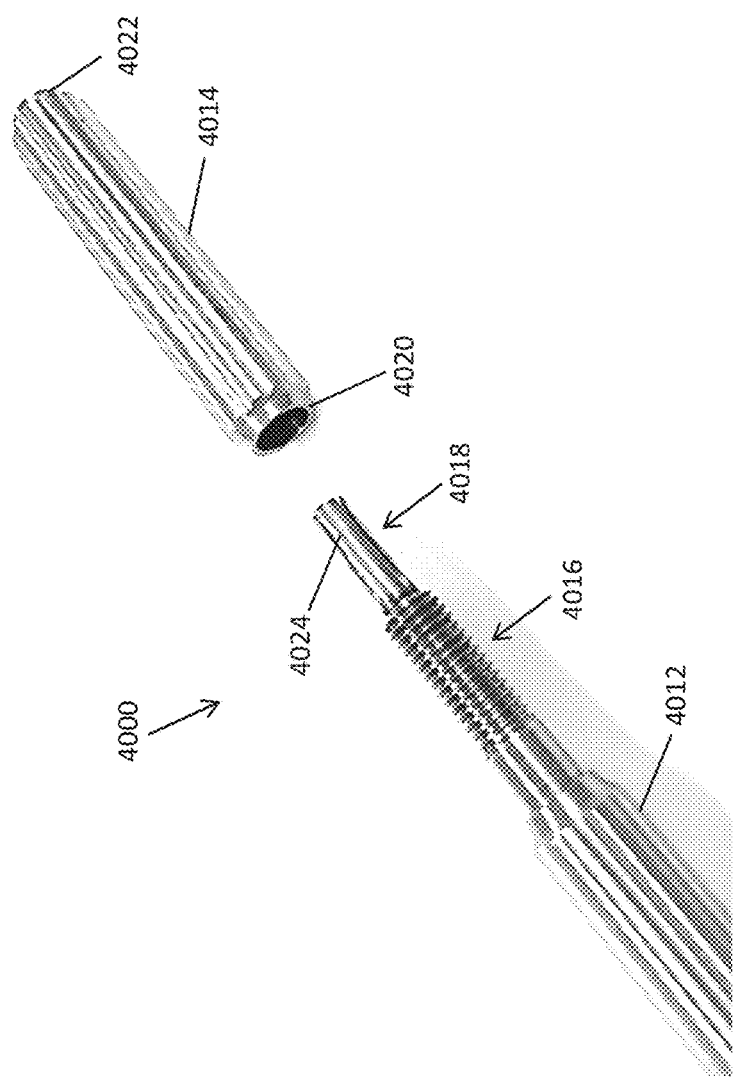
FIG. 35C shows a magnified view of an attachment mechanism of the dissection tool of FIGS. 35A and 35B.

In some variations, a dissection tool may releasably attach to an endoscope shaft, thereby preventing the dissection tool and endoscope from inadvertently separating during use. A secure connection between the dissection tool and the endoscope shaft may also improve a user's control of the endoscope and the dissection tool while maneuvering the devices. FIGS. 35A-35C show an example of an attachment mechanism for securing a variation of a dissection tool (4000) to an endoscope (4002). FIGS. 35A and 35B show the dissection tool (4000) partially surrounding an endoscope shaft (4004), and FIG. 35C is magnified view of a proximal portion of the dissection tool (4000). The dissection tool (4000) may comprise a distal section (4006) with a blade (4008), and a proximal section (4010) with a screw portion (4012) and a nut portion (4014). The screw portion (4012) may comprise external threads (4016), and the nut portion (4014) may comprise mating internal threads, thereby allowing the nut portion (4014) to be screwed onto the screw portion (4012). FIG. 35A shows the screw portion (4012) and the nut portion (4014) screwed together, whereas FIGS. 35B and 35C show them unscrewed.

The screw portion (4012) may comprise a compressible splayed section (4018) at its proximal end, adjacent to the external threads (4016). The nut portion (4014) may have an internal diameter that tapers from a first end (4020) to a second end (4022). When the nut portion (4014) is screwed onto the screw portion (4012), the splayed section (4018) may be inserted into the first end (4020). As the nut portion (4014) is screwed farther onto the screw portion (4012), the splayed section (4018) may move towards the second end (4022) of the nut portion (4014), which has a smaller internal diameter. The nut portion (4014) may be configured such that its internal surface increasingly impinges on the splayed section (4018) as the nut portion (4014) and screw portion (4012) are screwed together.

The splayed section (4018) may comprise one or more wings (4024), and pressure from the internal surface of the nut portion (4014) on the wings (4024) may cause them to deflect into a lumen of the screw portion (4012). In this way, screwing the screw portion (4012) and the nut portion (4014) together may decrease a diameter of a lumen of the dissection tool (4000). When the endoscope shaft (4004) is positioned in the lumen of the dissection tool (4000), the wings (4024) of the splayed section (4018) may press against the endoscope shaft (4004) as the nut portion (4014) is screwed onto the screw portion (4012). Friction between the wings (4024) and the endoscope shaft (4004) may releasably attach the dissection tool (4000) to the endoscope (4002). To release the dissection tool (4000) from the endoscope shaft (4004), the nut portion (4014) may be at least partially unscrewed from the screw portion (4012) (i.e., screwing the nut portion (4014) and the screw portion (4012) apart may increase the diameter of the lumen).

While the screw portion (4012) and nut portion (4014) are shown completely separated in FIGS. 35B and 35C, it should be appreciated in some variations, when the screw portion (4012) and nut portion (4014) are maximally unscrewed, they may remain connected. As shown, the proximal section (4010) of the dissection tool (4000) may comprise the attachment mechanism, but it should be appreciated that any portion of a dissection tool may comprise a mechanism for releasably attaching to an endoscope. In addition, while the attachment mechanism shown in FIGS. 35A-35C comprises a compressible portion to tighten around an endoscope shaft, a dissection tool may be configured to releasably attach to an endoscope in any suitable way (e.g., with friction from a non-compressible internal surface, with one or more clips, clamps, hooks, tethers, or the like).

In some variations, rather than being configured for use with an endoscope, a dissection tool may comprise a digital camera. Such a dissection tool may comprise a shaft with a blade positioned at its distal end. The blade may comprise any of the features discussed with respect to any of the blades (3508, 3608, 3702, 3802, or 3902) of FIGS. 30A-34. The dissection tool may comprise one or more lumens or compartments to house one or more elements of the camera. In some variations, the camera may comprise a maximum diameter of about 2 mm to about 2.5 mm. The camera may be configured to be connected to a display, such as an LCD display. A lens may be positioned near a distal portion of the dissection tool in order to provide visualization of an area surrounding a blade of the dissection tool. In some variations, the dissection tool may also comprise a light source. Some variations of dissection tools comprising a camera may be configured to be disposable, whereas others may be configured to be reused.

In some variations, a dissection tool may also comprise one or more of the features described above with respect to an electrical probe, which may allow the dissection tool to electrically stimulate nasal tissue. In this way, the combination dissection tool and electrical probe may be used to both identify an implantation site for a microstimulator and to form a tissue pocket for the microstimulator. For example, the dissection tool may comprise a conductive portion, which may be at least a portion of a blade and/or a portion of a shaft of the dissection tool. The conductive portion may be at least partially insulated, such as with an insulation sheath, as was discussed with respect to the electrical probe (1100) of FIG. 11. In some variations, at least a portion of the blade (e.g., a distalmost portion of the blade, a scoop of the blade, a convex portion of the blade) may be configured to deliver an electrical stimulus to nasal tissue. For example, a conductive portion of the blade may not be insulated, which may allow this conductive portion to deliver an electrical stimulus. In some variations, one or more electrodes may be positioned on the blade and/or on other portions of the dissection tool to deliver the electrical stimulus. In some variations, it may be advantageous for a dissection tool that is configured to be used with an endoscope, such as the dissection tools described with respect to FIGS. 30A-35C, to function as an electrical probe because this may allow the locations that are electrically stimulated to be visualized.

It may be desirable to have a depth stop on one or more of the devices configured to enter a nasal cavity, including the implantation tool, dissection tool, and electrical probe described herein. A depth stop may reduce the risk of advancing a device too far into a nasal cavity, which may cause the device to inadvertently damage nasal structures (e.g., the cribriform plate). A depth stop may indicate a distance relative to an inserted end of a device. In some variations, this distance may indicate a maximum distance that the device may be inserted into a nasal cavity. In some variations, a depth stop may be positioned on a device used for extending a tissue pocket, and the depth stop may indicate the desired length of a tissue pocket. The position of a depth stop may be compared to the position of a portion of a patient (e.g. the nostril, the inferior edge of the nasal septum). In some variations, a depth stop may be a marker, which may be visually compared to a portion of a patient. In some variations, a depth stop may physically resist over-insertion of a device by protruding from the device such that it may contact a portion of a patient if the device is advanced a sufficient distance. Depth stops may be positioned between about 25 mm and about 100 mm from a distal, inserted end of a device. In some variations, depth markers may be positioned every millimeter or centimeter from a distal end of a device to indicate a distance of insertion.

For example, a retractable cover of an implantation tool may comprise one or more markings that indicate a distance from the distal tip of the retractable cover. When the retractable cover and a microstimulator are inserted into a tissue pocket opening and the implantation tool is advanced, the position of the one or more markings on the retractable cover may be compared to the tissue pocket opening. This may allow a user to advance the implantation tool a desired distance, such that the microstimulator and retractable cover are inserted a desired distance into a tissue pocket. In some variations, this may be advantageous to reduce the risk of forming a tissue pocket that is too long and/or contacting structures (e.g., the cribriform plate) that may be inadvertently damaged.

Other variations of depth stops are shown in FIGS. 14A and 14B. In this example, the depth stops comprise one or more movable pins that may be inserted into one or more corresponding holes in a device. FIG. 14A shows a dissection tool (1402) that comprises a depth stop pin (1404) and two holes (1406) in the dissection tool shaft (1408) that the pin may be partially disposed in. As shown, the depth stop pin has been removed from the device. FIG. 14B shows a distal portion of an implantation tool (1410) that similarly comprises a depth stop pin (1412) and three holes (1414) in the implantation tool. As shown, the pin is partially disposed in the most distal hole and extends through the width of the implantation tool shaft (not shown) and retractable cover (1416), such that portions of the pin are exposed on opposite sides of the implantation tool. In this variation, the depth stop pin may be removed prior to retracting the retractable cover and releasing the microstimulator (1418). These holes may indicate maximum insertion distances from a distal tip of a device. The holes may be positioned at different distances from the distal tip, such that a user may select the best placement of the depth stop pin for the particular procedure and subject. For example, the holes may be positioned with one hole at about 25 mm, one at about 35 mm, and one at about 45 mm. Generally, it may be desirable for holes to be positioned between about 20 mm and about 50 mm. In some variations, different holes may be used to indicate maximum insertion distances for different nasal cavities sizes. A pin may be placed in a desired hole (e.g., the hole that corresponds to a maximum insertion distance for a specific patient) such that the pin protrudes from one or both sides of the dissection tool shaft. As the distal tip of the dissection tool is advanced into a nasal cavity, the pin may contact a portion of the patient (e.g., ala, inferior edge of the nasal septum) to resist further advancement. This may indicate that a maximum insertion distance has been reached. In some variations, a pin and/or hole may comprise a spring and/or other feature to prevent the pin from becoming unintentionally dislodged from the hole during the dissection procedure.

Another variation of depth stop comprises a ring and one or more protrusions. The ring may be disposed around a distal portion of a device that enters a nasal cavity (e.g., dissection tool, implantation tool, electrical probe) and may be positioned at a maximum insertion distance from a distal tip of the device, as was described in more detail herein. The ring may have a smooth inner surface to contact a device shaft. An outer surface of the ring may comprise one or more protrusions that may extend radially away from the center of the ring. Advancement of a device comprising a ring into a nasal cavity may result in one or more protrusions contacting a portion of the patient (e.g., ala, inferior edge of the nasal septum) to resist further advancement. In some variations, the ring may be flexible and may be sized such that it may be stretched to be positioned around a shaft of a device at different maximum insertion distances for different patients, and then relaxed to form a tight fit around the shaft. In some variations, the ring may be removable and may be used with different devices. In some variations, the one or more protrusions may be integrally formed with the ring, and in other variations the protrusions may be formed separately. Any of the devices that enter a nasal cavity may comprise depth stops configured in any suitable manner to provide a visual and/or tactile indication of the distance a device has been inserted into a nasal cavity.

Controller

Figure 24:
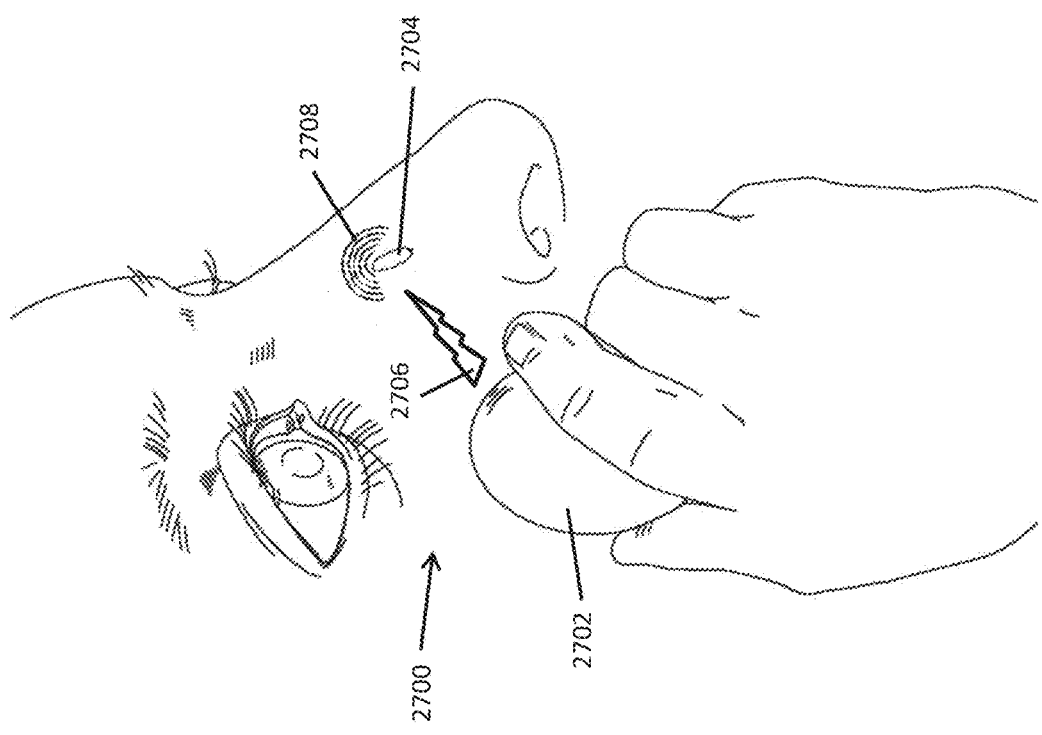
FIG. 24 shows a variation of a controller described here.

The nasal microstimulator implantation system described here may comprise a controller, which may communicate with the stimulation devices described here to transmit and/or receive power, information, or the like. The controller may remain external to the body and communicate wirelessly with the microstimulator. FIG. 24 depicts an exemplary external controller for use with the nasal microstimulator implantation systems described here. As shown there, a stimulation system (2700) includes a controller (2702) comprising a hand-held device. The controller may be brought to the vicinity of an implanted microstimulator (2704), and may produce an output signal (2706) received by the implanted microstimulator (2704). The implanted microstimulator may in turn generate a stimulation signal (2708) used to stimulate an anatomical target, as described in more detail herein. While the controller shown in FIG. 24 comprises a hand-held device, it should be appreciated that the controller may comprise any suitable form. For example, the controller may comprise a wearable device (e.g., glasses, wristwatch), a key fob, or be a component of a pillow configured to stimulate nasal tissue during sleep.

The controller may be configured to transmit one or more signals to an implanted microstimulator. In some variations, the output signal produced by the controller may provide power to the microstimulator. For example, in variations in which a nasal microstimulator implantation system comprises a microstimulator having a passive stimulation circuit (or a stimulation circuit that does not otherwise include a battery or internal power supply), the controller signal may power the stimulation device. In variations in which a microstimulator of a stimulation system comprises a power source, the signal of the controller may temporarily provide power to the microstimulator to assist in microstimulator operation and/or to recharge the power supply of the microstimulator.

In some variations, one or more of the signals produced by the controller may transmit information to one or more portions of the nasal microstimulator implantation system. For example, in variations where a nasal microstimulator implantation system comprises a microstimulator having an implantable pulse generator, the controller may provide programming instructions (e.g., stimulation parameters, stimulation times, etc.) to the implantable pulse generator. In variations where a microstimulator comprises an adjustable component, one or more output signals of the controller may be used to adjust the adjustable component.

FIG. 25 depicts a schematic diagram of one variation of a controller (2800) circuit suitable for use with the nasal microstimulator implantation systems described here. As shown there, the controller (2800) may include a power source (2802), an input module (2804), a controller (2806), and a transmission component (2808). The power source (2802) may provide a voltage or current to the controller (2806). The supplied power may be a constant voltage or current or an alternating voltage or current.

An input module (2804) may provide one or more input signals to a controller (2806) based on input received from a user such as a patient, a health professional, or other external source. For example, the user input may be a depressed button, an input along a slide bar, or some other input that indicates whether to apply stimulation to one or more anatomical targets (such as an anterior ethmoidal nerve within the nasal cavity), what type of stimulation to apply, and/or what stimulation parameters to apply. The input signals may also be generated from logic inside the input module (2804). For example, an input module (2804) may include logic to apply stimulation to nasal tissue periodically, in a ramped fashion, continuously, in a patterned fashion, in response to detecting a condition of low or decreased tear production, or some other condition. In some variations the stimulation may be ramped to prevent activation of pain sensation.

A controller (2806) may receive power from a power source (2802) and input signals from an input module (2804) to generate an output signal. The output signal may be a voltage signal or a current signal applied to a transmission element (2808). The output signal may vary in frequency, amplitude, period and/or phase based on the input received from an input module (2804) and power received from a controller (2802). The transmission element (2808) may be any element suitable for conveying energy and/or information to a microstimulator (not shown), such as one or more coils, ultrasound generators, optical energy generators, or the like. When the output signal is applied to a transmission element (2808) including a coil, the coil may generate a magnetic wave having a radio frequency and amplitude based on the output signal and coil. In some variations, the controller (2806) may detect one or more operating parameters of the microstimulator.

While the controller (2806) is shown in FIG. 25 as having an input portion, it should be appreciated that the controller need not have an input portion. FIG. 26 depicts a block diagram of another variation of controller circuit (2900) comprising a power source (2902), a controller (2904), and a transmission portion (2906). The power source (2902) may provide power to the controller (2904). The controller (2904) may be programmed or otherwise configured to produce one or more output signals, which may be transmitted to a microstimulator via a transmission portion (2906).

In some variations, it may be desirable to allow for a patient to alter the intensity of stimulation by increasing or decreasing the output strength of the controller. In some variations, a controller may comprise one or more buttons, sliders, levers, knobs, or other mechanisms a patient may manipulate to alter the output strength of the controller. In other variations, a nasal microstimulator implantation system may comprise one or more external programmers which may be used to alter the output of the controller. For example, the hand-held controller (2702) described with respect to FIG. 24 may be configured to communicate with and provide programming instructions to one or more other controllers.

In some variations, a controller may comprise one or more safety elements. For example, in some variations a controller may comprise a temperature sensor which measures the temperature inside the controller. In these variations, the controller may be configured to shut down when the temperature inside the controller exceeds a certain threshold. This may prevent the controller from reaching a temperature which may injure a patient (e.g., when the patient is holding the controller).

In some variations, a stimulation set may comprise a plurality of controllers, wherein each controller is configured to produce a different output signal. Other variations of controllers that may be suitable for use with a nasal microstimulator implantation system are described in more detail in U.S. patent application Ser. No. 13/441,806, filed Apr. 6, 2012, and titled "Stimulation Devices and Methods," which was previously incorporated by reference in its entirety.

Methods

Generally, the methods described herein comprise locating a desired micro stimulator implant site within a nasal cavity, implanting the microstimulator, and activating the microstimulator to generate lacrimation. Locating the desired microstimulator implant site within a nasal cavity may comprise using an electrical probe to stimulate areas adjacent to the nasal septum and visualize the area that produces a desired patient response (e.g., sneezing, tearing). The microstimulator may then be implanted in this area. Implanting the microstimulator may comprise forming a tissue pocket between the nasal septum and submucosa with devices that may include one or more dissection tools and/or an implantation tool. An implantation tool may then be used to insert a microstimulator into the tissue pocket. In some variations of the implantation methods, the ability of the microstimulator to produce an electrical stimulus may be assessed, and the microstimulator repositioned or otherwise adjusted if desired. After release of the microstimulator into a nasal tissue pocket of a patient, the area of implantation may be allowed to heal. The implanted microstimulator may then be activated to stimulate nasal tissue and increase tear production. Increasing tear production in this manner may be an effective treatment for patients with dry eye disease (DED).

Identification of Implantation Site

Figure 15:
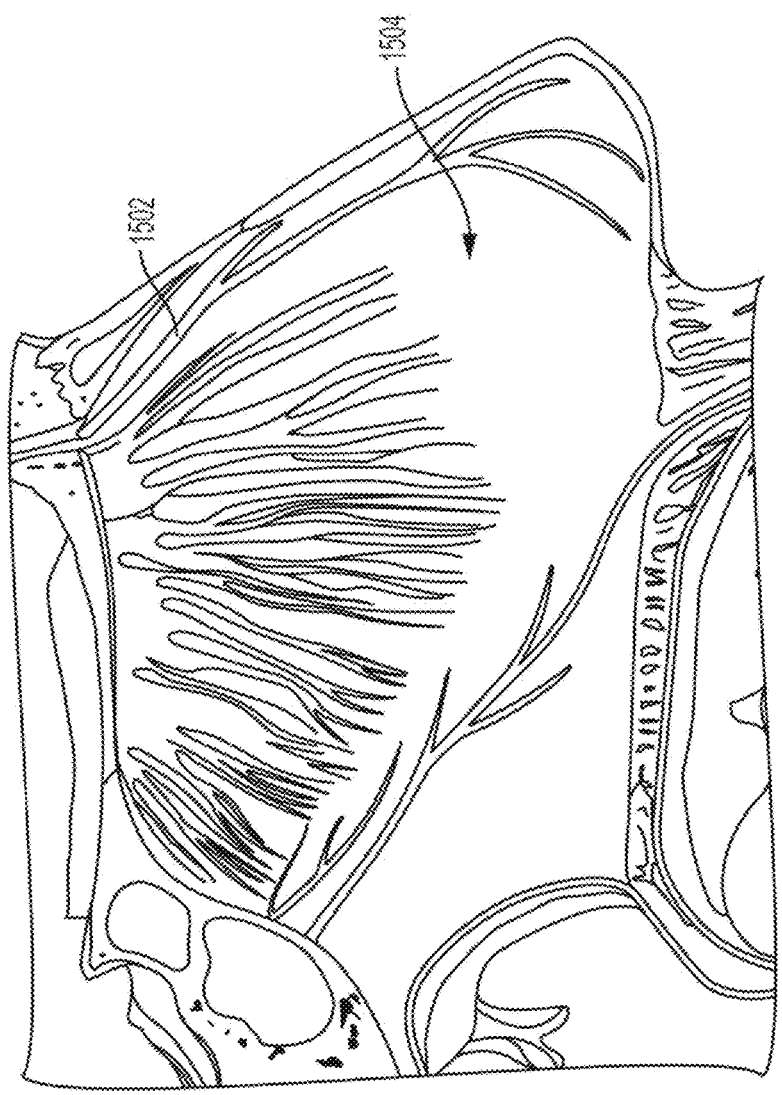
FIG. 15 shows a cutaway view of a nasal cavity.

Electrical stimulation of certain areas within the nasal cavity may increase tear production. As seen in the cutaway view of the nasal cavity in FIG. 15, one such area may be in proximity to the anterior ethmoidal nerve (1502). An anterior ethmoidal nerve, sometimes referred to as the nasociliary nerve, is generally located in an anterior and superior area within the nasal cavity on both sides of the nasal septum (1504). The exact location of this nerve in an individual may vary, as may the area of this nerve that may produce a desired patient response (e.g., sneezing, tearing) when stimulated. Identifying the desired microstimulator implantation site may comprise identifying the area adjacent to the nasal septum that produces the desired patient response. An electrical probe comprising one or more electrodes may be used to stimulate one or more areas adjacent to the nasal septum or at other locations in the nasal cavity while monitoring for a desired patient response to the stimulation. An endoscope, which may or may not be integrated into or attached to the electrical probe, may allow a user to visualize the area that produces the desired patient response and identify that area as the desired implantation site.

In some variations of identifying an implantation site, a patient may be partially or fully sedated. An electrical probe, such as the one described herein with respect to FIG. 11, may be inserted into a nostril of a patient and areas adjacent to the nasal septum may be electrically stimulated by the electrical probe's one or more electrodes. A patient response (e.g., sneezing, tearing, movement of nasal muscles) may be monitored while one or more areas are stimulated. In some variations of the electrical probe comprising two electrodes, the electrodes may deliver a stimulus simultaneously or separately before the electrical probe may be moved to a new position. In variations of the electrical probe comprising one electrode, the electrical probe may be moved to a new position after the electrode delivers a stimulus. The implantation site may be determined by the locating the area that produces a desired patient response or the greatest patient response when stimulated. In some variations, a test to measure tear output, such as a Schirmer test or measurement of tear meniscus height, may be performed during stimulation at one or more locations to help identify a desired implantation site.

One or both sides of the nasal septum may be stimulated. In variations of the methods comprising an implantation of one microstimulator, stimulation of both sides of the nasal septum may be advantageous, since in some patients, stimulation on one side may be more effective than on the other side. In variations of the methods comprising implantation of two microstimulators, stimulating both sides of the nasal septum with the electrical probe may identify a desired implantation site on each side of the nasal septum.

In some variations of the methods, a microstimulator may be implanted adjacent to a cartilaginous portion of the nasal septum. In other variations, a microstimulator may be implanted adjacent to a bony portion of the nasal septum. The bony portion of the nasal septum has its own blood supply, and therefore disruption of the submucosal layer to form a tissue pocket may not disrupt the blood supply of this portion of the septum. Nasal fractures may also occur more frequently at the transition points between the bony and cartilaginous parts of the septum, and implantation adjacent to the bony part may prevent a fracture from damaging and/or dislodging the microstimulator. In order to identify the bony and cartilaginous portions of the septum, a distal portion of the electrical probe or another device may be pushed laterally against the septum. The bony portion of the nasal septum may be less flexible than the cartilaginous portion of the nasal septum. Alternatively or additionally, a light source (e.g., a light source on the electrical probe, a light source on another device) may be used to identify the bony and cartilaginous parts of the septum. For example, a light source may be turned on within a nasal cavity, and the transition point between the cartilaginous and the bony part of the nasal bridge may be visualized from outside the nasal cavity, as the cartilaginous part allows more light to be transmitted. The transition point between the cartilaginous and bony parts of the nasal bridge may correspond in part with the transition point between the cartilaginous and bony parts of the nasal septum. In some variations, a light source may be turned on while located on one side of the nasal septum, and a detector (e.g., photodiode) may be placed on the other side of the septum to assess changes in light absorption, which may indicate the transition point from cartilage to bone.

An electrical probe may use similar electrical settings (e.g., amplitude, frequency, waveform) as the microstimulator in order to increase the likelihood that an implanted microstimulator will produce a similar response as the electrical probe. Different electrical waveforms may be tested using the electrical probe in order to identify an implantation site and/or to determine a stimulus waveform. For example, waveforms tested may include a constant on waveform having a frequency between 20 Hz and 150 Hz (e.g., about 30 Hz, about 70 Hz), an on/off waveform of similar frequency, and/or waveforms having modulated amplitude, frequency, and/or pulse widths may be tested.

Once the desired implantation site is determined, it may be marked for subsequent tissue pocket formation. For example, the relationship between the implantation site and one or more anatomic landmarks (e.g., nostril, nasal turbinate) may be visualized by a user. In other variations, the distance the electrical probe is inserted into the nasal cavity may be observed (e.g., by visualizing one or more depth stops on the electrical probe in relation to a nostril). In other variations, the desired implantation site may be physically marked, such as with a surgical marking pen or temporary surgical clip.

It should be appreciated that some variations of the methods may not comprise the use of an electrical probe. In these variations, anatomic landmarks may determine a desired implantation site. For example, a desired implantation site may be in the superior and anterior portion of the nasal cavity and/or a specific distance from an anatomic structure (e.g., a nostril, a nasal turbinate).

Tissue Pocket Formation

A tissue pocket for microstimulator implantation may be formed at a desired implantation site. Forming the tissue pocket may comprise incising nasal tissue to create a tissue pocket opening and extending the tissue pocket from the opening. Prior to the surgical procedure, the nasal cavity may be flushed with one or more antibacterial and/or cleansing agents (e.g., chlorhexidine). A medication that may produce local anesthesia and/or vasoconstriction (e.g., cocaine, lidocaine, epinephrine) may be administered to the area of implantation. A device, such as a dissection tool described herein, may then be used to form the tissue pocket opening by making an incision through nasal tissue. In some variations, the incision may be made in the nasal cavity through a portion of nasal mucosa and submucosa adjacent to the nasal septum. In other variations, the incision may be made at the columella, lateral to the nasal septum. The same device that was used to make the incision, or a different device, such as a different dissection tool or an implantation tool described herein, may then be advanced through the tissue pocket opening to extend the tissue pocket a desired length. The tissue pocket may be extended parallel to the nasal septum, between the mucosal layer and the nasal septum, either through the submucosal layer or between the submucosal layer and the nasal septum. One or more of these steps may be visualized with a visualization tool (e.g., an endoscope used alongside a dissection tool, an endoscope releasably attached to a dissection tool, an endoscope positioned within a lumen of a dissection tool, a camera incorporated into a dissection tool, as described herein).

Figure 16:
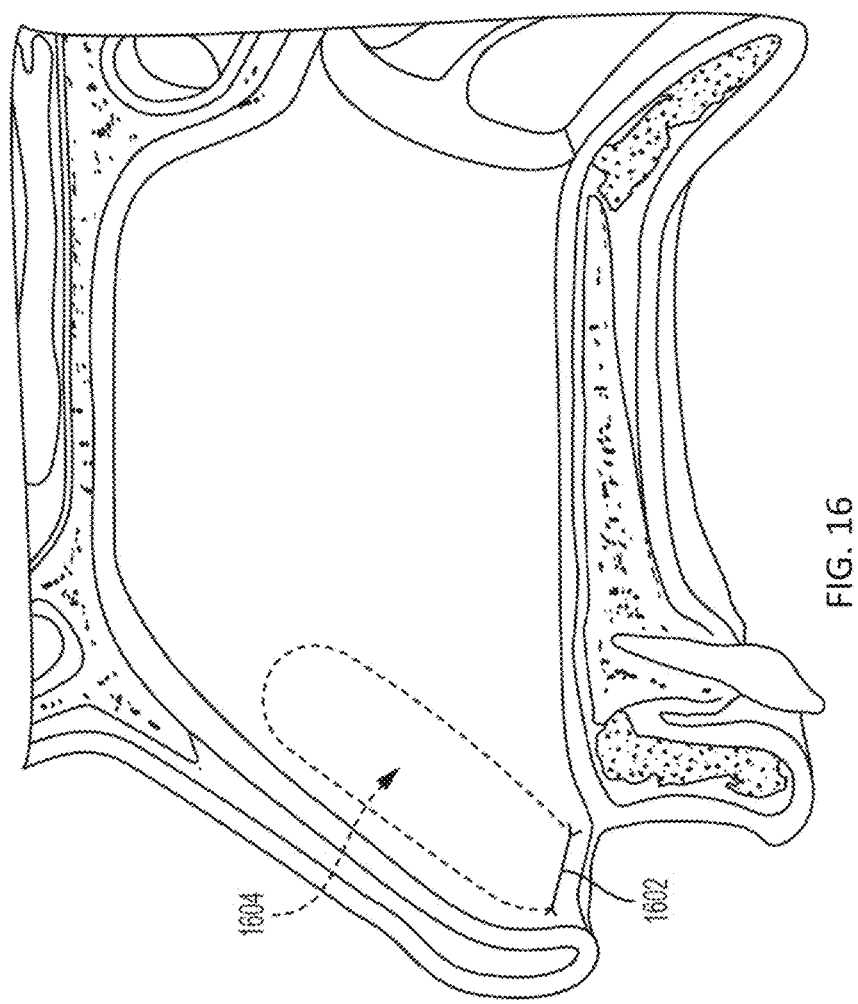
FIG. 16 shows a cutaway view of a nasal cavity and a variation of a tissue pocket described here.

FIG. 16 shows a cutaway view of a nasal cavity with an incision (1602) that may be the opening of a tissue pocket (1604). Any sharp edge may incise a portion of nasal mucosa and submucosa to form a tissue pocket opening. For example, any of the dissection tools described with respect to FIGS. 12A-13B and 30A-35C may comprise a curved, sharp blade to incise nasal tissue. In other variations, a flat blade may be used. The length of the incision may be at least as long as a dimension of the microstimulator that is parallel to the incision, but need not be. For example, the opening may be dilated as the microstimulator is inserted through the opening, or the opening may be dilated by a portion of a device. For example, in variations of the implantation tool that comprise a retractable cover with a distal tip, as shown in FIGS. 5A-5C, the distal tip (510) may have a tapered width such that a narrow portion may enter a tissue pocket opening first. As the implantation tool is advanced, the portion of the retractable cover at the tissue pocket opening may become wider, and the opening may be dilated.

After an incision has been made in nasal tissue, the amount of bleeding may be monitored and/or controlled. Significant bleeding may make visualization of the implant site difficult, which may increase the risk of a user inadvertently damaging nasal structures (e.g., the nasal septum, the cribriform plate) and/or extending the tissue pocket in an undesirable orientation. If significant bleeding occurs, a vasoconstrictive agent (e.g., cocaine, epinephrine) may be administered, the area irrigated, and/or the patient repositioned. A dissection tool (e.g., the dissection tool shown in FIGS. 13A, 13B, 30A-30C, 31) may additionally or alternatively be used to clear blood and/or other fluid from the implantation site. In some variations, bleeding may be controlled with electrocautery, which may be a capability of a dissection tool or another device.

After an incision has been made in nasal tissue to form an opening of a tissue pocket, the pocket may be extended. Generally, this may be accomplished by advancing at least a portion of a device into the tissue pocket opening and separating and/or elevating the submucosa from the nasal septum (e.g., the cartilaginous and/or bony portions of the nasal septum). Alternatively, the tissue pocket may be extended between layers of submucosa, and a thin layer of submucosa may remain covering the nasal septum. In some variations, extending a tissue pocket between layers of submucosa may be advantageous to preserve blood flow to the nasal septum and/or to decrease the risk of inadvertently damaging the nasal septum. Extending the tissue pocket may be done with the sharp edge used to incise the tissue, but using a blunt edge may reduce the risk of inadvertently damaging the nasal septum and/or other tissue. In some variations of the methods, the same device (e.g., dissection tool) may be used to make the tissue pocket opening and to extend the tissue pocket. For example, a dissection tool may comprise both a sharp blade and a blunt blade, as described in more detail with respect to FIG. 12A. The sharp blade (1212) may be used to form the tissue pocket opening, and the blunt blade (1204) may be used to extend the pocket. In other variations, different devices may be used to extend the tissue pocket and incise the tissue. For example, any of the variations of dissection tools shown in FIGS. 12A-13B and 30A-35C may comprise a blunt blade that may be used to separate and/or elevate the submucosa from nasal septum.

In some variations, the implantation tool may be used to extend the tissue pocket. For example, the implantation tool shown in FIGS. 5A-5C comprises a retractable cover (501) with a distal tip (510). In variations in which the distal tip (510) of the retractable cover (501) extends beyond the distal end (512) of the releasably attached microstimulator (502), the distal tip may be the most distal portion of the implantation system as it is advanced into a tissue pocket opening. When the retractable cover is in a distal, advanced position, as seen in FIGS. 5A and 5B, the curve of the distal tip may cover and/or shield the microstimulator from the forces involved in extending the tissue pocket. As described in more detail here, this configuration may reduce the risk of the microstimulator becoming dislodged from the implantation tool during tissue pocket extension. In other variations, when releasably attached to an implantation tool, a microstimulator may be used to extend the tissue pocket. For example, FIG. 6B shows a variation of implantation tool with a microstimulator (602) releasably attached to a distal end. The microstimulator may be advanced into a tissue pocket opening by the implantation tool and the distal end of the microstimulator may separate the submucosa from the nasal septum.

In some variations, the length of the formed tissue pocket may be at least the length of the microstimulator. For example, a microstimulator may comprise a length between about 15 mm and about 20 mm, and the tissue pocket may be about 2 mm to about 10 mm longer than this (that is, in this example, the tissue pocket may be about 17 mm to about 30 mm in length). In some of these variations, the length of the microstimulator may be approximately 17 mm, and the length of the tissue pocket may be approximately 2 mm. In some variations the length of the tissue pocket may be indicated and/or regulated by one or more depth stops or markings on the device being used to extend the tissue pocket (e.g., dissection tool, implantation tool). The relative position of one or more length markings may be compared to a portion of the patient (e.g., the ala) to indicate the length of the portion of the device that has been inserted into the nasal cavity. Similarly, the one or more length markings may be compared to the opening of the tissue pocket to indicate the length of a portion of the device that is within the tissue pocket, which may indicate the length of the tissue pocket. In some variations, a device may comprise protrusions that contact a portion of the patient (e.g., the nostril, inferior edge of the nasal septum) to limit further advancement of the device. These protrusions or depth stops may be positioned at a maximum insertion distance from a distal end of a device and reduce the risk of the device being advanced beyond this maximum insertion distance. This may reduce the risk a tissue pocket being extended farther than desired and inadvertently damaging tissue or a structure (e.g., cribriform plate). In some variations, as shown in FIG. 14, one or more depth stops on a dissection tool (1402) may comprise a movable pin (1404) that may be positioned in different holes (1406) on the device. Prior to extension of the tissue pocket, the pin may be positioned in a desired hole that may correspond to a desired maximum insertion distance from the pin to the distal end of the dissection tool. The maximum insertion distance may be estimated for a specific patient by one or more characteristics of the patient, such as nose size or height.

Figure 17:
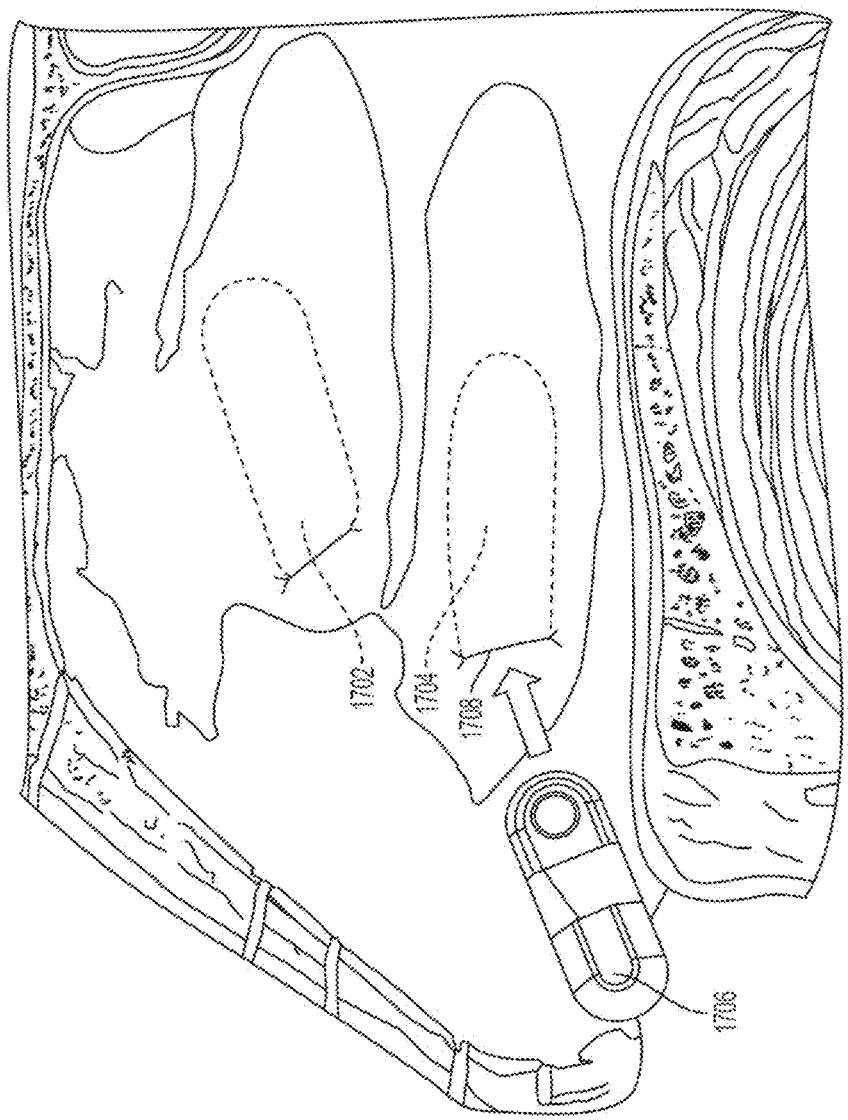
FIG. 17 shows a cutaway view of a nasal cavity and variations of tissue pockets and a microstimulator described here.
Figure 18:
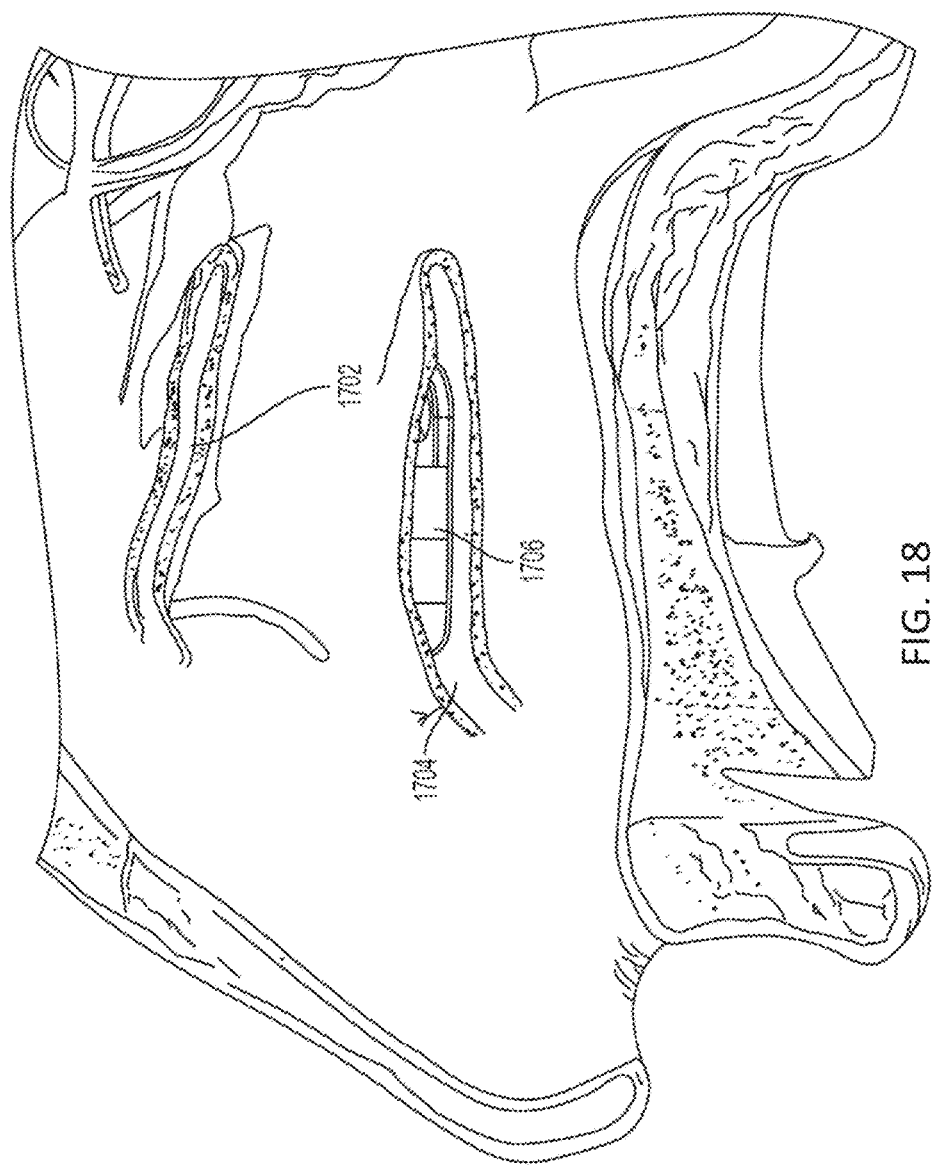
FIG. 18 shows a cutaway view of a nasal cavity and cut-away views of variations of tissue pockets described here.

The tissue pocket may be extended from the pocket opening to orient the pocket such that an electrode of an implanted microstimulator may stimulate a desired area of tissue. For example, when the target nerve is the anterior ethmoidal nerve, the desired area of tissue stimulation may be located in a superior and anterior portion of a nasal cavity, and a tissue pocket may be extended towards that position. In some variations it may be desirable to stimulate other areas in the nasal cavity, and a tissue pocket may be formed at those areas. For example, FIG. 17 shows a cutaway view of a nasal cavity illustrating two alternative tissue pocket locations. The first location (1702) is over the middle turbinate, and the second location (1704) is over the inferior turbinate. A microstimulator (1706) is shown being advanced towards an opening (1708) of the tissue pocket over the inferior turbinate. FIG. 18 shows a cutaway view of a nasal cavity with portions of the pockets (1702 and 1704) of FIG. 17 cut-away. A microstimulator (1706) is shown positioned in a pocket (1704) over the inferior turbinate, as it may appear after implantation.

Implantation

Figure 19:
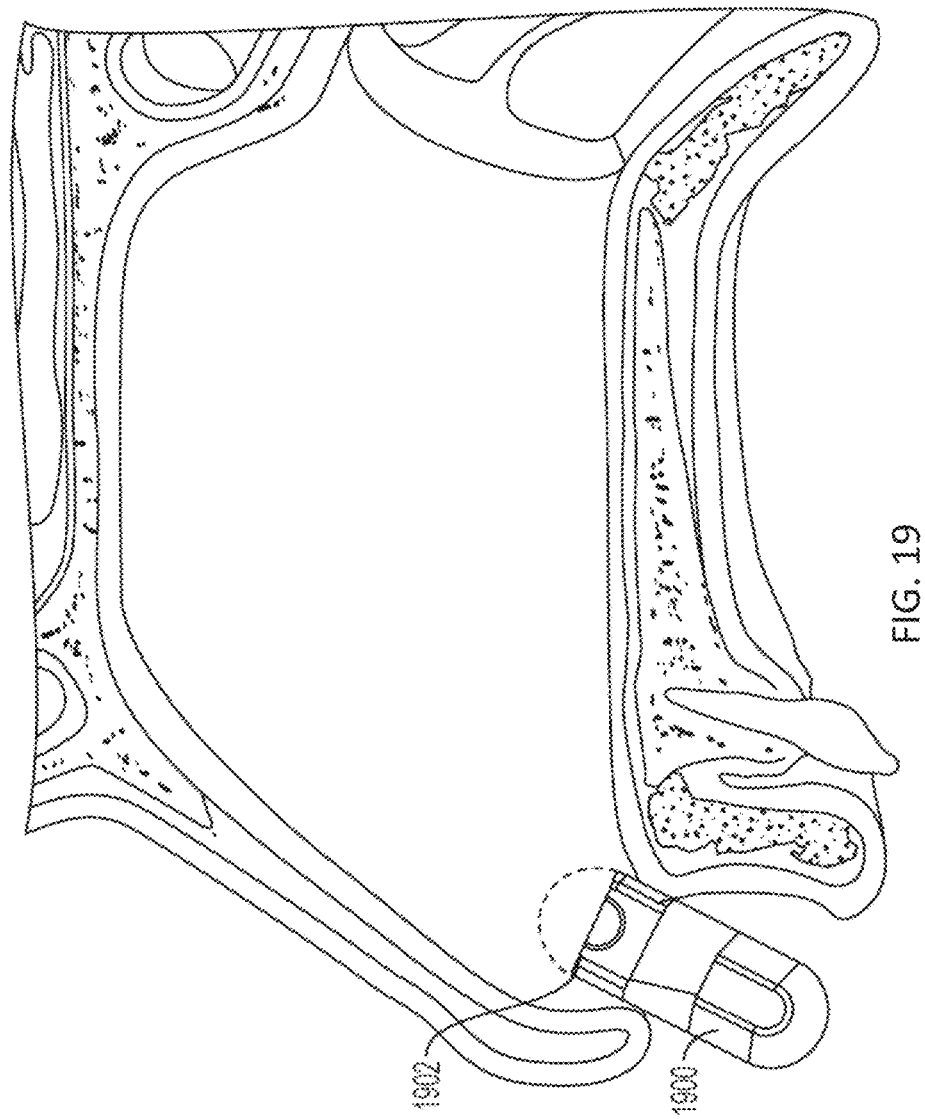
FIG. 19 shows a cutaway view of a nasal cavity and a variation of a tissue pocket opening and microstimulator described here.

After a tissue pocket has been formed, a microstimulator may be implanted into the tissue pocket. Generally, this comprises inserting a microstimulator into an opening of a tissue pocket and advancing it into the tissue pocket. FIG. 19 shows a cutaway view of a nasal cavity with a microstimulator (1900) partially advanced through a tissue pocket opening (1902). An implantation tool such as those described herein may be used to insert a releasably attached microstimulator into a tissue pocket. In some variations, the microstimulator and/or a portion of the implantation tool (e.g., a distal tip of a retractable cover) may be used to elevate the submucosa and mucosa of the tissue pocket to allow the microstimulator to be advanced into the tissue pocket. In other variations, a different tool may be used to separate the layers of the tissue pocket opening to allow the microstimulator to enter the tissue pocket.

Once a microstimulator is positioned a desired distance into a tissue pocket, the microstimulator may be released from the implantation tool. This process is shown in FIGS. 28A and 28B, which are fluoroscopic images taken during implantation of a microstimulator (3100) in a goat using a variation of implantation tool (3102) described herein. In FIG. 28A, the microstimulator is releasably attached to the implantation tool, and in FIG. 28B, the microstimulator has been released from the implantation tool. The method of release may be different for different embodiments of implantation tool and/or microstimulator. For example, in variations of the implantation tool that comprise a retractable cover, the retractable cover may be moved into a proximal, retracted position to expose the microstimulator, as seen in FIG. 5C, in preparation for release.

In variations of the implantation tool that comprise a tension system to releasably attach a microstimulator, the tension may be released in order to detach the microstimulator. For example, FIGS. 4A-4C illustrate a tension system for releasably attaching a microstimulator (410) to an implantation tool shaft (404). As is described in more detail herein, a tensioning element (406) may be looped through a microstimulator eyelet (412), travel through a lumen of the implantation tool shaft (404), and be secured at a proximal end of the shaft using a knob (408). Tension in the tensioning element may hold the microstimulator against the implantation tool at a contact surface (402). In some variations, the tension in the tensioning element may be released by cutting the tensioning element with a blade or scissors at a location between the knob of the implantation tool and the eyelet of the microstimulator. For example, the tensioning element may be cut close to the microstimulator eyelet, between the knob and proximal end of the shaft, or at a distal end of the knob. In some variations, the tensioning element may be secured between the knob and a portion of the shaft (e.g. between threaded portions of the knob and shaft that are screwed together). In these variations, the knob may be detached or loosened from the shaft in order to release the tensioning element.

After releasing the tension in the tensioning element (406) connecting the microstimulator (410) to the implantation tool, the tensioning element may remain looped through the eyelet (412) of the microstimulator as the implantation tool is withdrawn over the tensioning element. In some variations, leaving at least a portion of the tensioning element looped through the microstimulator eyelet may facilitate removal or repositioning of the device if needed. In some variations, the tensioning element may be pulled out of the microstimulator eyelet after the implantation tool is withdrawn over the tensioning element. In some variations, after releasing the tensioning element from the knob, the implantation tool may remain positioned near the microstimulator and the tensioning element may be withdrawn from the proximal opening (416) of the implantation tool lumen. This may pull the tensioning element out of the microstimulator eyelet. This variation of the release method may reduce the risk of inadvertently moving the microstimulator from its implantation site while the tensioning element is removed. This release method may be facilitated by positioning a tensioning element such that it has a short end and a long end extending proximal to the implantation tool when the tensioning element is secured at the knob. After releasing tension in the tensioning element, the long end may be easily accessed and pulled through the microstimulator connector and implantation tool lumen to withdraw the tensioning element.

In variations of an implantation tool that comprise a friction system for releasably attaching a microstimulator, the friction between the implantation tool and microstimulator may be overcome to release the microstimulator into a tissue pocket. FIGS. 6A-6C illustrate a nasal implant stimulation system that comprises a friction system. As shown, friction between the holder (608) of the implantation tool and the microstimulator may hold the microstimulator at the distal end of the implantation tool. A pusher (610) may be at least partially disposed in a lumen of the implantation tool shaft (604) and may be pushed against the microstimulator in order to overcome the friction holding the microstimulator to the implantation tool. A control slider (612) may be connected to the pusher (610) within the shaft lumen, and distal advancement of the control slider may distally advance the pusher. As shown in FIG. 6C, advancement of the pusher (610) may push the microstimulator (602) distally beyond the holder. When at least a portion of the microstimulator is in a tissue pocket, this may release the microstimulator from the implantation tool and deposit the microstimulator in the tissue pocket. The implantation tool may then be withdrawn through the nostril.

While the methods described here use an implantation tool to insert a microstimulator, it should be appreciated that in some variations, the microstimulator may be delivered to the tissue pocket in other suitable ways, such as with tweezers or forceps. In variations where release of a microstimulator from the implantation tool does not result in the microstimulator being completely within the tissue pocket, the microstimulator may be advanced farther so that it is completely within the pocket. This may be done by pushing a side of the microstimulator that is out of the tissue pocket with a distal end of the implantation tool or another device. In some variations, it may be advantageous for the microstimulator to be advanced into a tissue pocket such that there is at least about 5 mm between the microstimulator and the tissue pocket opening. This may increase the likelihood of proper closure and/or healing of the tissue pocket opening. In some variations, the layers of tissue surrounding a microstimulator may hold the microstimulator stationary within a tissue pocket via friction. In some variations, the microstimulator may be sutured or glued to increase the likelihood that the microstimulator remains stationary after implantation.

Figure 20:
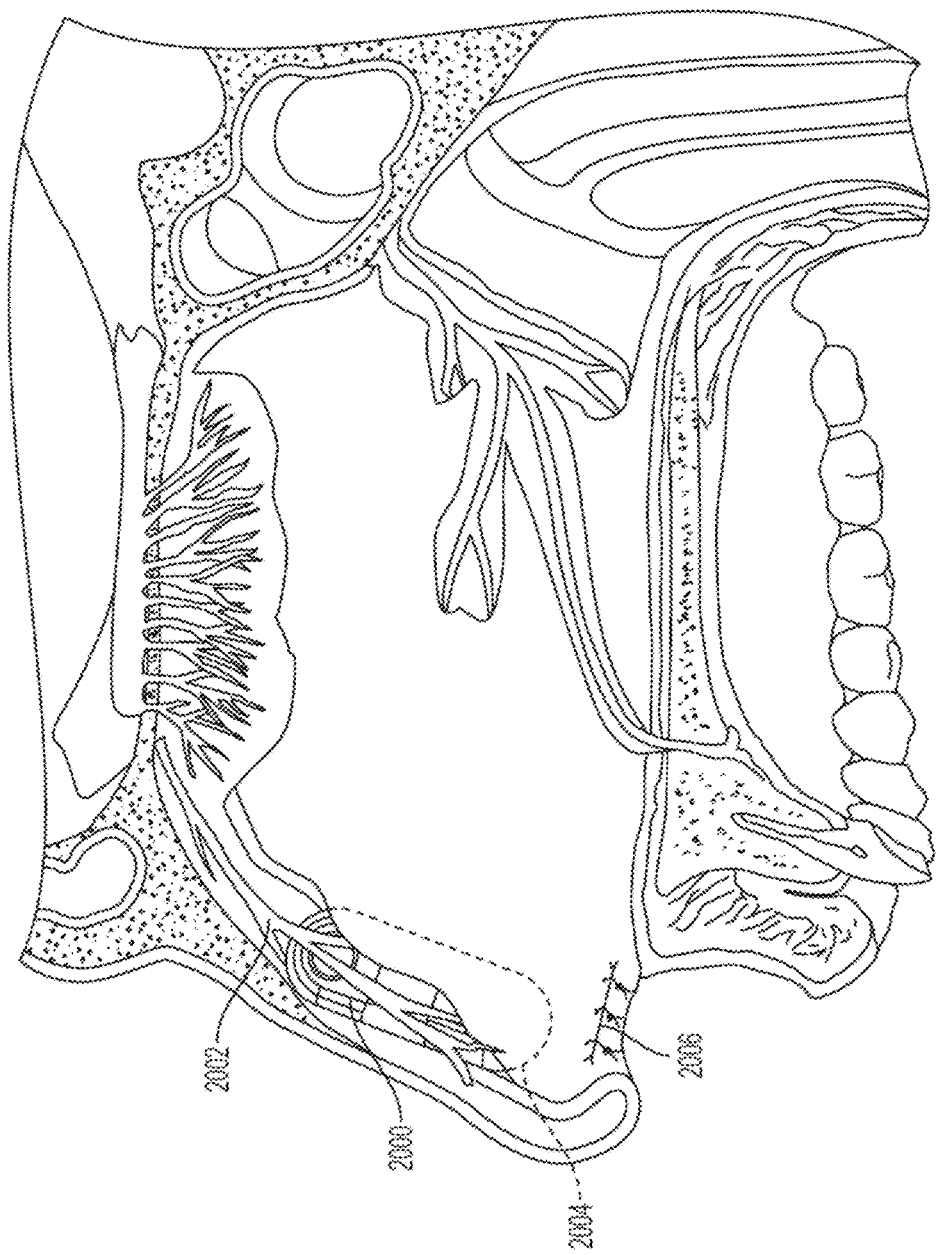
FIG. 20 shows a cutaway view of a nasal cavity and a variation of an implanted microstimulator.

The tissue pocket may be closed in any suitable manner. For example, the tissue pocket opening may be closed with sutures and/or with tissue glue. FIG. 20 shows a cutaway view of a nasal cavity with the submucosa and mucosa partially cut-away to reveal a microstimulator (2000) in an implanted position adjacent to the anterior ethmoidal nerve (2002). The microstimulator is within a tissue pocket (2004) that has been closed with sutures (2006). In some variations, packing the nasal cavity with an absorbent material (e.g., gauze) may exert pressure on the tissue pocket opening to facilitate closure. In some variations, the duration of the procedure from incision to closure may be about 5 minutes.

Stimulation Testing

The ability of a microstimulator to produce a desired electrical stimulus may be confirmed before, during, and/or after implantation of the microstimulator in a tissue pocket. In some variations, the electrical stimulus produced by a microstimulator in response to a signal from a controller may be tested prior to implantation. In some variations, a portion of the implantation tool may be used to test the electrical stimulus of the microstimulator. As was described in more detail with respect to FIGS. 5A and 5B, an implantation tool may comprise a retractable cover (504) that may be slidable over a portion of a shaft between a proximal retracted position and a distal advanced position. In the advanced position, as shown in FIGS. 5A and 5B, the retractable cover may cover at least a portion of one or more electrodes (514) of the microstimulator, which may facilitate sensing an electrical stimulus produced by the one or more electrodes. The implantation tool maybe configured to sense an electrical stimulus by comprising one or more electrodes. Before implantation, the retractable cover and microstimulator may be submerged in a conductive solution (e.g., saline), and a controller may be used to activate the microstimulator. If the microstimulator is functioning properly, it may generate an electrical signal, which may be detected by the one or more electrodes of the retractable cover. In some variations, a similarly configured implantation tool may test the electrical stimulus generated by the microstimulator during implantation. A controller may activate the microstimulator while it is attached to the implantation tool in a tissue pocket, and the implantation tool may detect whether the microstimulator produces the expected electrical stimulus.

After implantation, effectiveness of the microstimulator's electrical stimulus may be tested by monitoring a patient's response to stimulation. For example, after a patient has at least partially recovered from anesthesia, a controller may be used to activate the implanted microstimulator. A patient's response (e.g., tearing, sneezing, sensing paresthesia in the nasal cavity) may indicate that the microstimulator is providing an appropriate electrical stimulus to a desired location. In some variations, a Schirmer test or other suitable method for measuring tear production may be performed and compared to results of a Schirmer test done prior to implantation to determine if stimulation increases tear production. If the desired response is not observed, one or more settings on the controller may be adjusted and stimulation repeated. Alternatively or additionally, the implantation site may be confirmed, such as by using an electrical probe, as was previously described. The electrical probe may be used to deliver an electrical stimulus to the implantation site area, and a patient's response may be monitored. If a less than desired patient response is observed with stimulus to the implantation site area, other areas of the nasal cavity may be tested. If another area is found to generate a more robust patient response, the microstimulator may be repositioned to that area. If stimulation of the implantation site by the electrical probe produces a desired patient response (e.g., tearing, sneezing), the implantation site may be correct, but the microstimulator may not be delivering an appropriate electrical stimulus. In this case, the microstimulator may be removed.

Repositioning/Removal

A microstimulator may be removed from a nasal cavity or repositioned within a nasal cavity. To remove a microstimulator, at least a portion of the microstimulator may be exposed, which may comprise incising tissue overlying or in proximity to the microstimulator. In some variations, a tissue pocket opening may be reopened, such as by cutting sutures on the opening, to expose a portion of the microstimulator. The exposed portion of the microstimulator may be accessed to withdraw the microstimulator from the tissue pocket. In some variations, the exposed portion of the microstimulator may comprise a connector, which may have been used to attach the microstimulator to an implantation tool during insertion. An implantation tool or a separate device may connect to the connector to withdraw the microstimulator from the tissue pocket. For example, the microstimulator (200) shown in FIG. 2A comprises a connector in the form of an eyelet (204). A retrieval tool, such as is seen in FIG. 10, may hook onto the connector of the microstimulator in order to withdraw the microstimulator from the tissue pocket. In some variations, a portion of the tensioning element that was used to attach the microstimulator connector to the implantation tool may still be connected to the connector. Pulling the tensioning element may remove the device through an incised opening in tissue.

In order to reposition a microstimulator, it may be removed and implanted in a different location using the methods described previously for implantation. In other variations, the microstimulator may be repositioned without completely removing the microstimulator. For example, a portion of the device may be accessed through the tissue pocket opening or an incision in the nasal tissue overlying or adjacent to the microstimulator. This exposed portion of the microstimulator may be manipulated (e.g., pushed in a particular direction) to reposition the microstimulator. For example, the microstimulator may be advanced farther into a tissue pocket.

Treatment

A patient may use a controller to activate an implanted microstimulator, such that the microstimulator delivers an electrical stimulus according to one or more treatment regimens. For example, to treat dry eye disease, stimulation may be delivered as-needed and/or according to a predetermined regimen. In some variations, a patient may use a controller to activate an implanted microstimulator to deliver a round of stimulation when the patient experiences dry eye symptoms. A round of stimulation may have any suitable duration (e.g., between 1 second and 10 minutes).

In other instances, stimulation may be delivered on a scheduled basis. A patient may use a controller to activate a microstimulator according to a schedule or a microstimulator and/or controller may be configured to automatically deliver a stimulus according to a schedule. In some variations the microstimulators described here may be used to provide a round of stimulation at least once daily, at least once weekly, or the like. In some variations, the microstimulators may be used to deliver multiple rounds of stimulation each day (e.g., at least two treatments daily, at least three treatments daily, at least four treatments daily, at least five treatments daily, at least six treatments daily, at least seven treatments daily, at least eight treatments daily, between two and ten times daily, between four and eight times daily, or the like). In some variations, the stimulation may be delivered at certain times of day.

When the microstimulator is used to provide stimulation on a scheduled basis, in some variations each round of stimulation may be the same length (e.g., about 30 seconds, about 1 minute, about 2 minutes, about 3 minutes, about 4 minutes, about 5 minutes, about 10 minutes, or longer than 10 minutes). In other variations, some rounds of stimulation may have different predetermined lengths. In yet other variations, the patient may choose the length of the round of stimulation. In some of these variations, the patient may be given a minimum stimulation time (e.g., about 5 seconds, about 10 seconds, about 30 seconds, about 1 minute, about 2 minutes, about 3 minutes, about 5 minutes, or the like) and/or a maximum stimulation time (e.g., about 1 minute, about 2 minutes, about 3 minutes, about 5 minutes, about 10 minutes, about 20 minutes, or the like). In some instances, the delivery schedule or stimulation parameters may be changed based on the time of day (e.g., daytime use vs. nighttime use). In some instances, stimulation may be delivered on a continuous basis.

In some variations, the treatment regimens of providing the stimuli described herein may cause periodic or regular activation of the nasolacrimal reflex, which may in turn treat dry eye and/or improve ocular health. Further details regarding the mechanisms by which nasal stimulation may improve ocular health and treatment regimens may be found in U.S. patent application Ser. No. 14/256,915, filed Apr. 18, 2014, and titled "Nasal Stimulation Devices and Methods," which is hereby incorporated by reference in its entirety.

Example #1

Two goats were implanted under sterile conditions with a microstimulator and stimulated at least once weekly for 33 days while collecting Schirmer score data to quantify tear production. A Schirmer score recorded in millimeters was determined by using Schirmer test strips, with a greater distance corresponding to greater tear production. The microstimulator implanted was similar to the microstimulator (200) of FIGS. 2A and 2B. The microstimulator was composed primarily of medical grade silicone, titanium (CP Grade 2), and titanium nitride-coated titanium. The microstimulator dimensions were approximately 17 mm×5 mm×2 mm (L×W×H) and the approximate total surface area was 190 mm$^2$. The microstimulator was placed into the left nasal cavity in both animals, below the submucosa of the nasal septum, in one animal on the cartilage and in the other animal on the bony part of the septum.

Using an electrical probe similar to the electrical probe (1100) of FIG. 11, the desired implantation location was identified as a position where electric stimulation of the anterior ethmoidal nerve caused the goat to sneeze. To do so, prior to the implantation surgery, the septal mucosa was electrically stimulated, confirming the medial side inside the nasal cavity as the best location, approximately 7 cm to 10 cm cranially measured from the nostril. Animals showed movement of some nasal musculature at the nostril and one animal sneezed when stimulated electrically; both animals produced large amounts of nasal mucous and saliva with electrical stimulation. This effect had been previously determined not to occur with mechanical stimulation alone.

Figure 21:
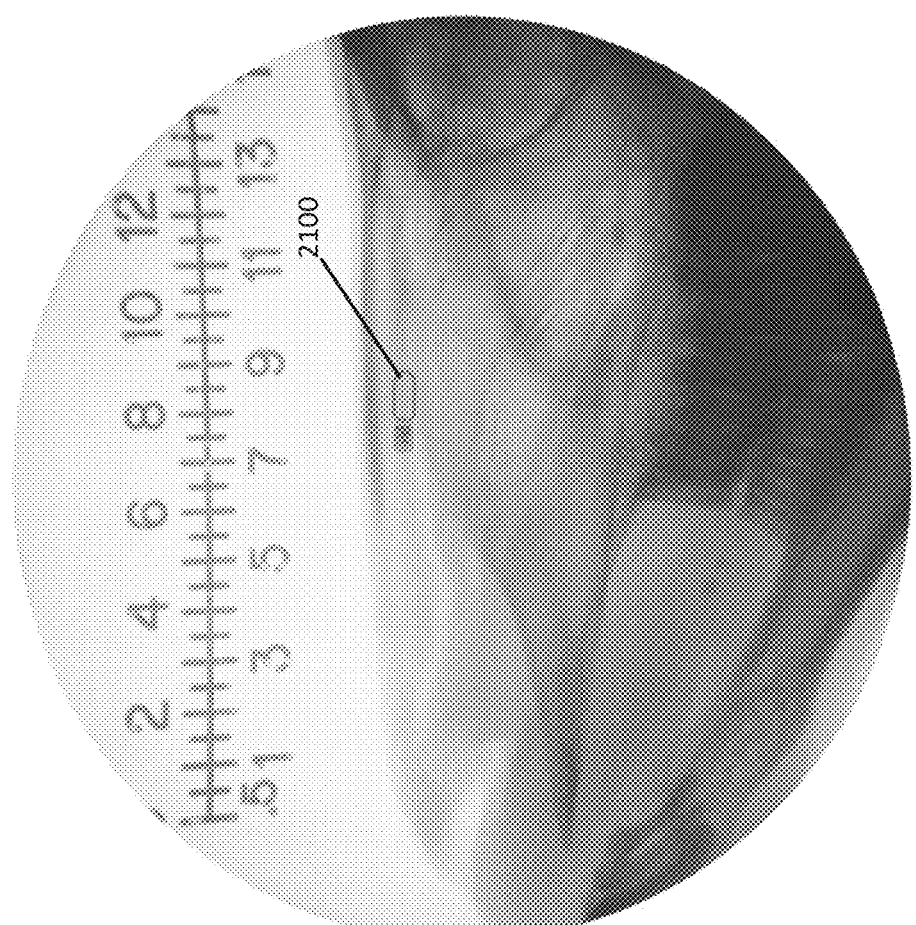
FIG. 21 shows a fluoroscopic image of a portion of a goat skull and a variation of a microstimulator described here.

The procedure was done under endoscopic visualization, and videos and photos were recorded. A pocket was created below the submucosa, approximately 5 cm to 7 cm from the nostril and extended to a depth of about 4 cm. A sterile microstimulator (rated up to 2.4 mA) was placed (coil-first) into the pocket below the submucosa of the nasal septum, approximately 9 cm from the nostril opening of the goat. The pocket was closed, in one animal by packing the nostril with sterile gauze for twenty minutes, in a second animal by pressing the pocket wall to adhere to the septum (no packing). FIG. 21 is a fluoroscopic image of a goat skull with an implanted microstimulator (2100).

The surgery was performed under partial sedation. Each time electric stimulation was applied, animals were only lightly sedated to preserve reflexes. The depth of anesthesia was assessed by testing for various reflexes (blinking of the eye in response to noise, and tickle of the periorbital skin, withdrawal of the head, and ear-wiggle responding to tickle).

Three hours after the successful implant procedure, each animal responded with repeated sneezing to stimulation using a controller similar to controller (2702) described with respect to FIG. 24. One day post implant, each animal was stimulated repeatedly using the controllers to collect Schirmer score data. Schirmer tests were first collected as basal Schirmer (no stimulation), followed by repeated Schirmer tests using electric stimulation. Average Schirmer score test results are reported below. Subsequent Schirmer tests were collected on days 3, 5, 6, 12, 21, 27, and 33 of the study.

Figure 22:
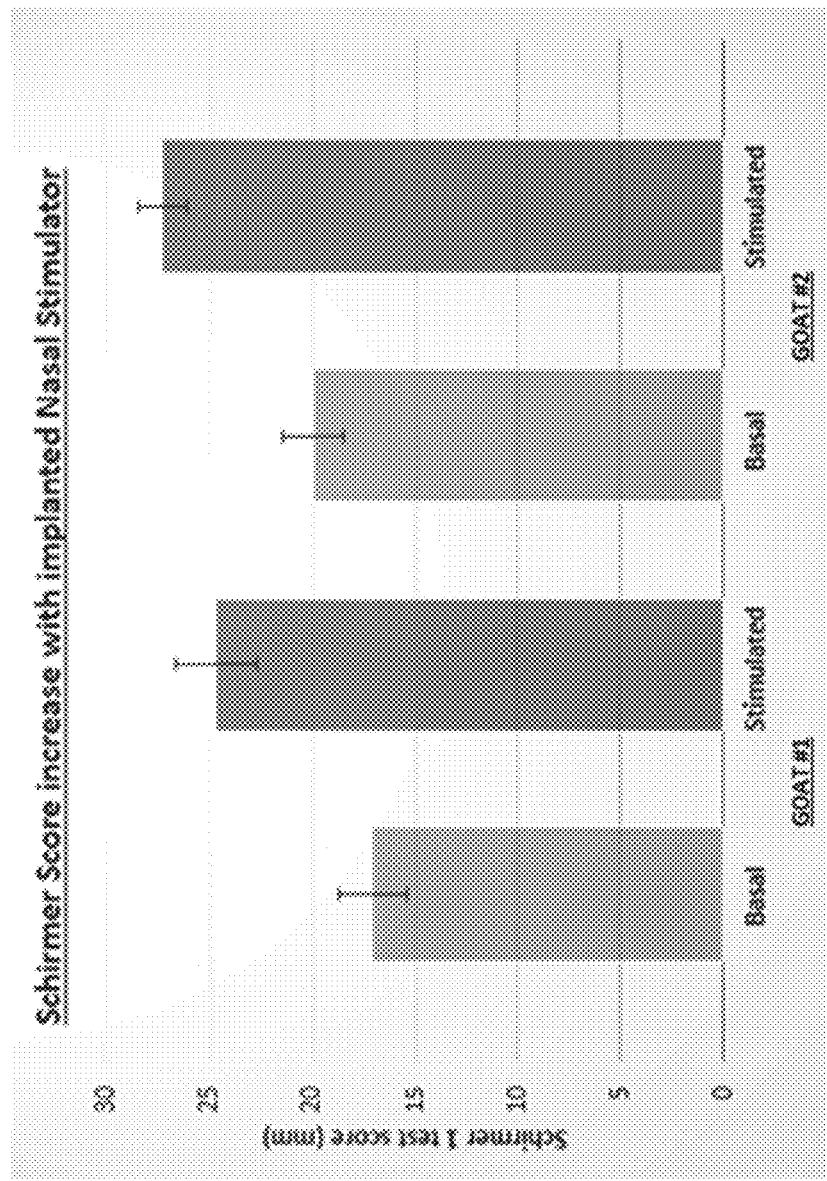
FIG. 22 shows a bar graph depicting tear production in goats implanted with a variation of a microstimulator described here.

Unilateral electric nasal stimulation using the implanted microstimulators lead to a bilateral increase in Schirmer test scores. Schirmer scores recorded with electric stimulation ("acute" Schirmer scores) showed an increase in tear output in comparison to basal Schirmer scores (without stimulation). FIG. 22 is a bar graph showing the average tear output from both eyes (left eye tear output+right eye tear output/2) for each goat with and without stimulation, reported by Schirmer score. Across both goats, the acute Schirmer scores (during stimulation) were about 40% higher than basal Schirmer scores on average. For the first goat, tear output increased by an average of 44.5%, from 17.1±1.7 mm (mean±SEM) to 24.7±2.0 mm. For the second goat, tear output increased by an average of 36.4%, from 20.0±1.5 mm to 27.3±1.2 mm.

The table below shows the basal and acute (stimulation) Schirmer scores averaged from both eyes for each goat during multiple stimulation sessions. As seen, the effectiveness of stimulation did not diminish over time.

TABLE 1

Basal and acute (stimulation) Schirmer scores, average for both eyes.

| Test Date | Schirmer Score (mm) (average of both eyes) | | Stim/Basal Ratio |
|---|---|---|---|
| | Basal | Stim | |
| Goat 1 | | | |
| 18 Jul. 2014 | 15.3 | — | — |
| 21 Jul. 2014 | 9.0 | 13.3 | 1.5 |
| 23 Jul. 2014 | 17.5 | 25.7 | 1.5 |
| 24 Jul. 2014 | 24.5 | 25.2 | 1.0 |
| 30 Jul. 2014 | 16.0 | 26.3 | 1.6 |
| 8 Aug. 2014 | 19.0 | 29.3 | 1.5 |
| 14 Aug. 2014 | 20.0 | 25.2 | 1.3 |
| 20 Aug. 2014 | 15.5 | 28.0 | 1.8 |
| | | | Change in Schirmer |
| Mean | 17.1 | 24.7 | 7.6 |
| (percent) | 100.0 | 144.5 | |
| StDev | 4.5 | 5.3 | |
| SEM | 1.7 | 2.0 | |
| Goat 2 | | | |
| 18 Jul. 2014 | 15.0 | — | — |
| 21 Jul. 2014 | 25.5 | 30.3 | 1.2 |
| 23 Jul. 2014 | 16.5 | 26.3 | 1.6 |
| 24 Jul. 2014 | 20.5 | 22.7 | 1.1 |
| 30 Jul. 2014 | 22.0 | 29.3 | 1.3 |
| 8 Aug. 2014 | 19.5 | 26.2 | 1.3 |
| 15 Aug. 2014 | 24.5 | 31.7 | 1.3 |
| 20 Aug. 2014 | 16.5 | 24.7 | 1.5 |

TABLE 1-continued

Basal and acute (stimulation) Schirmer scores, average for both eyes.

| Test Date | Schirmer Score (mm) (average of both eyes) | | Stim/Basal Ratio |
|---|---|---|---|
| | Basal | Stim | |
| | | | Change in Schirmer |
| Mean | 20.0 | 27.3 | 7.3 |
| (percent) | 100.0 | 136.4 | |
| StDev | 3.9 | 3.2 | |
| SEM | 1.5 | 1.2 | |

Summary:
7.4 Improvement in Schirmer score (mm) with stimulation
40.5 % Improvement in Schirmer score with stimulation Average ipsilateral increases in tear output were also analyzed. In the eye on the implanted (left) side, the acute Schirmer score was about 45% greater than the basal Schirmer score in each animal. In the eye on the contralateral (right) side, the acute Schirmer score was about 56% greater than the basal Schirmer score in the first animal and 33% greater than the basal Schirmer score in the second animal. It is hypothesized that anesthesia might have affected more reflex pathways in the second animal. The table below shows the average basal and acute (stimulation) Schirmer scores for the left and right eyes of each goat.

TABLE 2

Basal and acute (stimulation) Schirmer scores for each eye.

| | Left (implanted) | | | Right | | |
|---|---|---|---|---|---|---|
| Animal | Basal Schirmer Score | Acute Schirmer Score | Ratio of Acute to Basal Schirmer Score | Basal Schirmer Score | Acute Schirmer Score | Ratio of Acute to Basal Schirmer Score |
| 1 | 17.7 | 25.4 | 1.44 | 16.0 | 25.2 | 1.56 |
| 2 | 19.0 | 27.9 | 1.47 | 20.0 | 26.5 | 1.33 |

The mechanical and electrical probing of the nasal cavity prior to implantation surgery revealed that there was no preference for either the left or the right side from an efficacy standpoint: electric stimulation on either side caused the animal to sneeze and increased the production of nasal (then rather liquid) mucous, as well as saliva output.

Example #2

Four goats were each implanted with one functional microstimulator and four non-functional replica implants, all of which remained in place for a 49-day study period. An objective of the study was to determine the efficacy of electrical stimulation using a microstimulator operating at 1.2 mA. In addition, surgical tools and techniques for implantation and explantation were evaluated. The microstimulator implanted was similar to the microstimulator (200) of FIGS. 2A and 2B. The microstimulator was composed primarily of medical grade silicone, titanium (CP Grade 2), and titanium nitride-coated titanium. The microstimulator dimensions were approximately 17 mm×5 mm×2 mm (L×W×H) and the approximate total surface area was 190 mm². The replica implants had approximately the same dimensions and surface area as the microstimulator, but they were composed entirely of silicone.

For each goat, the implantation site for the microstimulator was determined using an electrical probe, similar to the electrical probe (1100) of FIG. 11, to identify an area that produced a desired response (e.g., sneezing) when stimulated. Under sterile conditions, an incision was made in this area through the nasal mucosa and submucosa, adjacent to the nasal septum. Using a blunt dissection tool with suction, a tissue pocket was extended from the incision with visualization provided by an endoscope. A microstimulator was then delivered to the pocket with its electrode facing laterally using an implantation tool similar to the implantation tool (3000) of FIGS. 27A-27E. The implantation procedure was similar for the replica implants, but the implantation sites were determined based on anatomic landmarks and the positions of other implants, not the results of stimulation with an electrical probe.

On the final day of the study, additional surgical tools and techniques were evaluated through the successful implantation and immediate explantation of three microstimulators in one goat. During this procedure, the dissection tool used to extend the tissue pocket (i.e., separate the submucosa from the septal cartilage) was a blunt dissection tool that formed a sleeve around an endoscope shaft, similar to the dissection tool (3500) of FIGS. 30A-30C.

In order to determine the efficacy of the 1.2 mA microstimulator, each goat underwent electrical stimulation with the implanted microstimulator on the day of implantation (the first day of the study) and 14, 21, 27, 35, and 45 days after implantation. For each goat and on each day of stimulation, the minimum intensity of stimulation that resulted in the goat sneezing was determined. Over the course of the study, the average stimulation intensity required to produce sneezing was different for each goat. However, none of the goats required stimulation at the maximum intensity that the 1.2 mA microstimulator was capable of producing. All of the implanted microstimulators remained functional (i.e., capable of producing an electrical stimulus that led to sneezing) between implantation and the final day of electrical stimulation, 45 days after implantation.

Example #3

A human cadaver study was performed to evaluate surgical tools and techniques for implanting a microstimulator similar to the microstimulator (200) of FIGS. 2A and 2B. This study indicated that an implantation procedure similar to those described with respect to Examples #1 and #2 could be successfully performed on human anatomy. For example, a tissue pocket was formed adjacent to the nasal septum and the microstimulator was implanted using an implantation tool similar to the implantation tool (3000) of FIGS. 27A-27E. FIGS. 29A-29C are fluoroscopic images obtained during this procedure. FIG. 29A depicts the formation of a tissue pocket in the nasal cavity using a dissection tool with a blunt blade (3400). FIG. 29B shows a microstimulator (3402) attached to the distal end of an implantation tool (3404) as the microstimulator (3402) is inserted into the tissue pocket. FIG. 29C depicts the microstimulator (3402) implanted in the nasal tissue pocket after the implantation tool has been withdrawn.

The invention claimed is:

1. A method of implanting a microstimulator into nasal tissue of a nasal cavity to increase tear production in a patient having dry eye, comprising:
   identifying an implantation site along a nasal cavity in the patient, the identifying comprising:
   delivering, via a locator probe, a test electrical stimulus to nasal tissue of a nasal cavity; and
   detecting a response to the test electrical stimulus, the response comprising tear production in the patient;
   implanting the microstimulator at the identified implantation site, the microstimulator comprising a stimulation electrode; and
   delivering an electrical current from the stimulation electrode to stimulate an anterior ethmoidal nerve in the nasal tissue to increase tear production in the patient.

2. The method of claim 1, wherein the electrical current comprises a pulsed electrical stimulus.

3. The method of claim 2, wherein the pulsed electrical stimulus comprises a biphasic symmetric pulse waveform.

4. The method of claim 3, wherein a frequency of the biphasic pulse waveform is between 20 Hz and 80 Hz.

5. The method of claim 2, wherein the pulsed electrical stimulus has a waveform with a varying pulse width.

6. The method of claim 2, wherein the pulsed electrical stimulus has a waveform with a varying frequency.

7. The method of claim 2, wherein the pulsed electrical stimulus has a waveform with a varying amplitude.

8. The method of claim 1, wherein implanting the microstimulator comprises:
   forming a pocket at the identified implantation site; and
   inserting the microstimulator into the pocket.

9. The method of claim 8, wherein at least a portion of the pocket is located adjacent to the anterior ethmoidal nerve.

10. The method of claim 8, wherein the delivering the test electrical stimulus comprises electrically stimulating at least two different locations along nasal tissue located within the nasal cavity.

11. The method of claim 8, wherein the pocket is substantially between a mucosal layer and the nasal septum.

12. The method of claim 8, wherein forming the pocket comprises incising the nasal tissue to create a pocket opening and extending the pocket from the pocket opening.

13. The method of claim 12, wherein the pocket is extended using a dissection tool comprising a shaft, a blade at a first end of the shaft, and a suction opening extending through a portion of the blade.

14. The method of claim 12, wherein the pocket is extended using a dissection tool, comprising:
   a shaft comprising a distal end and a proximal end;
   a blade positioned at the distal end of the shaft; and
   a lumen, wherein the lumen extends distally from an opening at the proximal end of the shaft, and wherein the lumen is configured to receive an endoscope shaft therewithin.

15. The method of claim 14, wherein the dissection tool further comprises a compressible section configured to change a diameter of the lumen in order to releasably attach the dissection tool to the endoscope shaft.

16. The method of claim 8, wherein the microstimulator is implanted into the pocket using an implantation tool comprising a retractable cover.

17. The method of claim 8, further comprising testing the microstimulator before implanting the microstimulator into the pocket, wherein the testing comprises detecting an electrical signal generated by the microstimulator after submerging the microstimulator in a conductive solution.

18. The method of claim 1, wherein the locator probe comprises an endoscope and an electrode, the electrode being coupled to the endoscope and configured to deliver the test electrical stimulus to nasal tissue.

19. The method of claim 1, wherein the response further comprises one or more of sneezing and paresthesia.

20. The method of claim 1, wherein the identifying further comprises:
   indicating, using a depth stop, a distance the locator probe is inserted into the nasal cavity.

21. The method of claim 1, wherein the test electrical stimulus is delivered to a surface of the nasal tissue located within the nasal cavity.

22. The method of claim 1, wherein the pocket is formed at the implantation site through a surface of the nasal tissue located within the nasal cavity.

23. The method of claim 1, wherein the implantation site is positioned adjacent a bony portion of the nasal septum.

\* \* \* \* \*